(12) United States Patent
Li et al.

(10) Patent No.: US 11,608,511 B2
(45) Date of Patent: *Mar. 21, 2023

(54) METHODS FOR MODIFYING GENOMIC DNA

(71) Applicant: MaxCyte, Inc., Gaithersburg, MD (US)

(72) Inventors: Linhong Li, North Potomac, MD (US); Madhusudan Peshwa, Boyds, MD (US)

(73) Assignee: MaxCyte, Inc., Gaithersburg, MD (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/566,320

(22) PCT Filed: Apr. 13, 2016

(86) PCT No.: PCT/US2016/027253
§ 371 (c)(1),
(2) Date: Oct. 13, 2017

(87) PCT Pub. No.: WO2016/168275
PCT Pub. Date: Oct. 20, 2016

(65) Prior Publication Data
US 2018/0112235 A1    Apr. 26, 2018

Related U.S. Application Data

(60) Provisional application No. 62/146,618, filed on Apr. 13, 2015.

(51) Int. Cl.

| | | |
|---|---|---|
| *C12N 15/90* | (2006.01) | |
| *A61K 48/00* | (2006.01) | |
| *C12N 5/0783* | (2010.01) | |
| *A61P 35/00* | (2006.01) | |
| *A61K 35/17* | (2015.01) | |
| *A61K 35/33* | (2015.01) | |
| *C12N 5/077* | (2010.01) | |
| *C12N 9/22* | (2006.01) | |
| *C12N 9/96* | (2006.01) | |
| *C12N 15/11* | (2006.01) | |

(52) U.S. Cl.
CPC ............ *C12N 15/907* (2013.01); *A61K 35/17* (2013.01); *A61K 35/33* (2013.01); *A61K 48/00* (2013.01); *A61P 35/00* (2018.01); *C12N 5/0636* (2013.01); *C12N 5/0646* (2013.01); *C12N 5/0652* (2013.01); *C12N 9/22* (2013.01); *C12N 9/96* (2013.01); *C12N 15/11* (2013.01); *C12N 15/902* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | 530/324 |
| 5,475,096 A | 12/1995 | Gold et al. | 536/23.1 |
| 5,570,163 A | 10/1996 | Yamauchi | 399/170 |
| 5,612,207 A | 3/1997 | Nicolau et al. | 435/173.6 |
| 5,720,921 A | 2/1998 | Meserol | 422/44 |
| 6,074,605 A | 6/2000 | Meserol et al. | 422/33 |
| 6,090,617 A | 6/2000 | Meserol | 435/285.2 |
| 6,485,961 B1 | 11/2002 | Meserol | 435/285.2 |
| 6,617,154 B1 | 9/2003 | Meserol | 435/285.2 |
| 6,773,669 B1 | 8/2004 | Holaday et al. | 422/44 |
| 7,029,916 B2 | 4/2006 | Dzekunov et al. | 435/461 |
| 7,141,425 B2 | 11/2006 | Dzekunov et al. | 435/461 |
| 7,186,559 B2 | 3/2007 | Dzekunov et al. | 435/461 |
| 7,771,984 B2 | 8/2010 | Dzekunov et al. | 435/285.2 |
| 9,855,297 B2 * | 1/2018 | Duchateau | A61K 35/17 |
| 2003/0032175 A1 | 2/2003 | Siebel et al. | 435/320.1 |
| 2004/0087025 A1 * | 5/2004 | June | C12N 15/87 |
| | | | 435/455 |
| 2004/0115784 A1 | 6/2004 | Dzekunov | 435/173.6 |
| 2004/0214333 A1 | 10/2004 | Liu et al. | 435/459 |
| 2005/0019311 A1 | 1/2005 | Holaday et al. | 424/93.7 |
| 2005/0282200 A1 | 12/2005 | Dzekunov et al. | 435/6.12 |
| 2006/0110793 A1 | 5/2006 | Goldenberg et al. | 435/69.1 |
| 2007/0059833 A1 | 3/2007 | Li et al. | |
| 2008/0138877 A1 * | 6/2008 | Dzekunov | A61N 1/327 |
| | | | 435/173.6 |
| 2008/0311095 A1 | 12/2008 | Holmes et al. | |
| 2011/0065171 A1 | 3/2011 | Dzekunov et al. | 435/285.2 |
| 2013/0122591 A1 | 5/2013 | Cost et al. | |
| 2013/0326645 A1 * | 12/2013 | Cost | C12N 15/8213 |
| | | | 800/14 |
| 2014/0065616 A1 | 3/2014 | Xu | 435/6.11 |
| 2014/0120622 A1 * | 5/2014 | Gregory | A61K 35/26 |
| | | | 435/462 |

(Continued)

FOREIGN PATENT DOCUMENTS

| | | |
|---|---|---|
| JP | 2007-007430 | 1/2007 |
| JP | 2008-507300 | 3/2008 |

(Continued)

OTHER PUBLICATIONS

Genovese et al Nature 235-240 (Year: 2014).*

(Continued)

*Primary Examiner* — Anoop K Singh
(74) *Attorney, Agent, or Firm* — Norton Rose Fulbright US LLP

(57) ABSTRACT

Compositions and methods concern the sequence modification of an endogenous genomic DNA region. Certain aspects relate to a method for site-specific sequence modification of a target genomic DNA region in cells comprising: contacting the cells with an activating composition; transfecting the cells with a transfection composition comprising (a) donor DNA and (b) a DNA digesting agent; wherein the donor DNA comprises: (i) a homologous region comprising nucleic acid sequence homologous to the target genomic DNA region; and (ii) a sequence modification region; and wherein the genomic DNA sequence is modified specifically at the target genomic DNA region.

7 Claims, 22 Drawing Sheets

Specification includes a Sequence Listing.

(56) References Cited

U.S. PATENT DOCUMENTS

| | | | |
|---|---|---|---|
| 2016/0053283 A1 | 2/2016 | Wang et al. | 435/7.4 |
| 2016/0153006 A1 | 6/2016 | Zhang et al. | |

FOREIGN PATENT DOCUMENTS

| | | | | |
|---|---|---|---|---|
| JP | 2008-509653 | 4/2008 | | |
| WO | WO 1998/37757 | 9/1998 | | |
| WO | WO 2002/026966 | 4/2002 | | |
| WO | WO 2003/018751 | 3/2003 | | |
| WO | WO 2004/031353 | 4/2004 | | |
| WO | WO 2007/118208 | 10/2007 | | |
| WO | WO 2012/001073 | 1/2012 | | |
| WO | WO 2012/012738 | 1/2012 | | |
| WO | WO-2012012738 A1 * | 1/2012 | | C12N 15/85 |
| WO | WO 2013/139994 | 9/2013 | | |
| WO | WO 2013/188522 | 12/2013 | | |
| WO | WO 2014/059173 | 4/2014 | | |
| WO | WO 2014/144237 | 9/2014 | | |
| WO | WO 2014/191128 | 12/2014 | | |
| WO | WO 2015/160683 | 10/2015 | | |
| WO | WO 2016/036754 | 3/2016 | | |

OTHER PUBLICATIONS

Kim et al Genome Res. 24, 1012-1019, (Year: 2014).*
Novak et al.Molecular and Cellular Biology,1515-1527 (Year: 1992).*
Zhao et al.Vet Immunology and Immunopathology, 179-186 (Year: 2011).*
Genovese et al Nature, 510, 235-240 (Year: 2014).*
Ramos et al Expert Opin. Biol. Ther. 11(7), 855-873 (Year: 2011).*
Fields et al PLOS One, 8, 6, e68201, 1-9 (Year: 2013).*
Kim et al Genome Research, 1012-1019 (Year: 2014).*
Hsu et al. Nat Biotechnology. Sep;31(9):827-32 (Year: 2013).*
Lee et al., Drug Discovery Today: Disease Models, vol. 20, 13-20 (Year: 2016).*
Kosicki et al. Nature Biotechnology, 36, 765-771 (Year: 2018).*
Cox et al , Nature Medicine 21(2), 121-131 (Year: 2015).*
Li et al Biomaterials. July ; 171: 207-218 (Year: 2018).*
Hamar et al (Nature Portfolio, 11, 7854, 1-17 (Year: 2021).*
Singh et al PLos One, e64138, 1-11 (Year: 2013).*
De Ravin et al., "Targeted gene addition in human CD34+ hematopoietic cells for correction of X-linked chronic granulomatous disease," Nature Biotechnology, 34(4):424-429, (2016).
Field et al., "Comparison of lentiviral and sleeping beauty mediated [alpha] [beta] T cell receptor gene transfer" PLoS One, 8(6):e68201, (2013).
Field et al., "Engineered T cell therapies," Expert Reviews in Molecular Medicine, 17(4), (2015).
Genovese et al., "Targeted genome editing in human repopulating haematopoietic stem cells" Nature, 510(7504):235-240, (2014).
Hashimoto et al., "Electroporation of Cas9 proteins/sgRNA into early pronuclear zygotes generates non-mosaic mutants in the mouse," Developmental Biology, 418(1): 1-9, (2016).
International Search Report and Written Opinion issued in International Patent Application No. PCT/IB 17/54446, dated Jan. 4, 2018.
International Search Report and Written Opinion issued in International Patent Application No. PCT/US2016/027253, dated Jun. 16, 2016.
International Search Report and Written Opinion issued in International Patent Application No. PCT/US2014/028561, dated Aug. 1, 2014.
Lin et al., "Enhanced homology-directed human genome engineering by controlled timing of CRISPR/Cas9 delivery," eLife, 3:e04766, (2014).
Ma et al., "Effect of sodium Butyrate and Propionate on Cell Growth, Metabolism and Expression of the chimeric Antibody," China Biotechnology, 2005, 25(10): 12-16. (English Abstract).
Novak et al., "In vitro transfection of fresh thymocytes and T cells shows subset-specific expression of viral promoters" Molecular and Cellular Biology, 12(4): 1515-1527, (1992).

Office Action issued in Chinese Patent Application No. 201480021503. 5, dated Apr. 20, 2018.
Office Action issued in Japanese Patent Application No. 2016/502834, dated Feb. 28, 2018.
Osborn et al., "Evaluation of TCR gene editing achieved by TALENs CRISPR/Cas9, and megaTAL nucleases" Molecular Therapy, 24(3):570-581, (2016).
Palin et al., "Human neonatal naive Cd4+ T cells have enhanced activation-dependent signaling regulated by the MicroRNA miR-181a" The Journal of Immunology, 190(6):2682-2691, (2013).
Ramos et al., "Chimeric antigen receptor (CAR)-engineered lymphocytes for cancer therapy" Expert Opinion on Biological Therapy, 11(7):855-873, (2011).
Rong et al., "Homologous recombination in human embryonic stem cells using CRISPR/Cas9 nickase and a long DNA donor template," Protein Cell, 5(4):258-260, (2014).
Schumann et al., "Generation of knock-in primary human T cells using Cas9 ribonucleoproteins," Proceedings of the National Academy of Science, 112(33):10437-10442, (2015).
Wang et al., "Establishment of leukocyte-associated immunoglobulin like-receptor 2 (CD306) eukaryotic expression vector and purification and identification of fusion protein," Journal of Clinical Rehabilitative Tissue Engineering Research, 2009, 13(50): 12-10. (English Abstract).
Wang et al., "Highly efficient homology-driven genome editing in human T cells by combining zinc-ginger nuclease mRNA and AAV6 donor delivery" Nucleic Acids Research, 44(3):e30-e30, (2015).
Wurm et al., "Production of recombinant protein therapeutics in cultivated mammalian cells," Nature Biotechnology, 2004, 22(11):1393-1398.
Yang et al., "Construction of Anti-VEGFR-2 scFv-Fc Fusion Antibody and Stable Expression in CHO-k Cells," Pharmaceutical Biotechnology, 2011, 18(3): 206-210. (English Abstract).
Zhang et al., "Biallelic targeting of expressed genes in mouse embryonic stem cells using the Cas9 system," Methods, 69(2):171-178, (2014).
Zhao et al., "High transfection efficiency of porcine peripheral blood T cells via nucleofection" Veterinary Immunology and Immunopathology, 144(3):179-186, (2011).
Derouazi et al.: "Serum-free large-scale transient transfection of CHO cells", Biotechnology and Bioengineering, 87(4), (2004), pp. 537-545.
Edmonds et al.: "Development of Transfection and High-Producer Screening Protocols for the CHOK1SV Cell System", Molecular Biology, 34(2), (2006), pp. 179-190.
Fan et al.: "Improving the efficiency of CHO cell line generation using glutamine synthetase gene knockout cells", Biotechnology and Bioengineering, 109(4), (2012), pp. 1007-1015.
Florea et al.: "Polyethyleneimine in Differentiated Calu-3 and Non-differentiated COS-1 Cell Cultures", AAPS Pharm Sci., 4(3) Article 12, (2002), pp. 1-11.
International Search Report and Written Opinion issued in Application No. PCT/US2015/025523, dated Jul. 21, 2015.
International Search Report and Written Opinion issued in PCT/US2014/028561, dated Aug. 1, 2014.
Johansson et al.: "Yellow Fluorescent Protein-Based Assay to Measure GABAA Channel Activation and Allosteric Modulation in CHO-K1 Cells", PLoS ONE, 8(3): e59429, (2013), pp. 1-7.
Li et al., "Genomic Editing of Human Hematopoietic Stem Cells Using Non-Viral, Clinical Scale, cGMP Platform and Messenger RNA (mRNA) Encoding Nucleases," Molecular Therapy, 22(1): 2014, S278.
Musunuru, "Genome editing of human pluripotent stem cells to generate human cellular disease models," Disease Models & Mechanisms, 6(4): 2013, 896-904.
Nair et al.: "Effect of different UCOE-promoter combinations in creation of engineered cell lines for the production of Factor VIII", BMC Research Notes, 4:178, (2011), pp. 1-8.
Ran et al., "Genome engineering using the CRISPR-Cas9 system," Nature Protocols, 8(11): 2013, 2281-2308.

(56) References Cited

OTHER PUBLICATIONS

Reisinger et al.: "Serum-free transfection of CHO cells with chemically defined transfection systems and investigation of their potential for transient and stable transfection", Cytotechnology, 60(1-3), (2009), pp. 115-123.

Steger et al., "CHO-S Antibody Titers >1 Gram/Liter Using Flow Electroporation-Mediated Transient Gene Expression followed by Rapid Migration to High-Yield Stable Cell Lines," *Journal of Biomolecular Screening* 2015; 20(4): pp. 545-551.

Tait et al.: "Transient production of recombinant proteins by Chinese hamster ovary cells using polyethylenimine/DNA complexes in combination with microtubule disrupting anti-mitotic agents", Biotechnology and Bioengineering, 88(6):707-21, (2004), pp. 1-15.

Auer et al., "CRISPR/Cas9 and TALEN-mediated knock-in approaches in zebrafish," *Methods*, 69:142-150, (2014).

Kim et al., "Highly efficient RNA-guided genome editing in human cells via delivery of purified Cas9 ribonucleoproteins," *Genome Research*, 24:1012-1019, (2014).

Berdien et al., "TALEN-mediated editing of endogenous T-cell receptors facilitates efficient reprogramming of T lymphocytes by lentiviral gene transfer" *Gene Therapy*, 2014, 21:539-548.

Li et al., "CGMP-Compliant, Clinical Scale, Non-Viral Platform For Efficient Gene Editing Using CRISPR/CAS9" 20th Annual ISCT Meeting, p. S37, 2014.

Li et al., "Genomic Editing of Human Hematopoietic Stem Cells Using Non-Viral, Clinical Scale, cGMP Platform and Messenger RNA (mRNA) Encoding Nucleases" *Molecular Therapy*, 2014, 22(Supp 1):S278.

Li et al., "Highly Efficient, Large Volume Flow Electroporation" *Technology in Cancer Research & Treatment*, 2002, 1(5):341-349.

Li et al., "Large Volume Flow Electroporation of mRNA Clinical Scale Process" *Methods in Molecular Biology*, 2013, 969:127-138.

Mali et al., "RNA-Guided Human Genome Engineering via Cas9" *Science*, 2013, 339:823-826.

Office Action issued in Corresponding Japanese Patent Application No. 2016-562503, dated May 16, 2019 (English Translation).

Wang et al., "One-Step Generation of Mice Carrying Mutations in Multiple Genes by CRIPR/Cas-Mediated Genome Engineering" *Cell*, 2013, 153:910-918.

Watanabe et al., "Knockout of exogenous EGFP gene in porcine somatic cells using zinc-finger nucleases" *Biochemical and Biophysical Research Communications*, 2010, 402:14-18.

Zhao et al., "High-Efficiency Transfection of Primary Human and Mouse T Lymphocytes Using RNA Electroporation" *Molecular Therapy*, 2006, 13(1):151-159.

Cannon, et al., "Electroporation of ZFN mRNA Enables Efficient CCR5 Gene Disruption in Mobilized Blood Hematopoietic Stem Cells at Clinical Scale," Molecular Therapy, 21(Suppl. 1): S71-S72, 2013.

Extended European Search Report Issued in Corresponding European Patent Application No. 17830593.4, dated Feb. 13, 2020.

Yang, et al., "Optimization of Scarless Human Stem Cell Genome Editing," Nucleic Acids Research, 41(19): 9049-9061, 2013.

Maier, et al., "Efficient Clinical Scale Gene Modification Via Zinc Finger Nuclease-Targeted Disruption of the HIV Co-Receptor CCR5," Human Gene Therapy, 24: 245-258, 2013.

Office Action Issued in Corresponding European Patent Application No. 16718143.7, dated Jan. 28, 2020.

Singh, et al., "Manufacture of Clinical-Grade CD19-Specific T Cells Stably Expressing Chimeric Antigen Receptor Using Sleeping Beauty System and Artificial Antigen Presenting Cells," PLOS One, 8(5): e64138, 2013.

Jinek et al., "A programmable dual—RNA—guided DNA endonuclease in adaptive bacterial immunity", Science, 337(6096):816-821, 2012.

Hsu et al., "Development and Applications of CRISPR-Cas9 for Genome Engineering", *Cell*, 157, Jun. 5, 2014:1262-1278.

Hashimoto and Takemoto, "Electroporation enables the efficient mRNA delivery into the mouse zygotes and facilitates CRISPR/Cas9-based genome editing", *Sci Rep.*, 5:11315, 2015.

De Ravin, "CRISPR-Cas9 Gene Repair of Hematopoietic Stem Cells From Patients with x-Linked Chronic Granulomatous Disease," *Science Translational Medicine*, 9(372): eaah3480 pp. 1-10, 2017.

Flynn, CRISPR-Mediated Genotypic and Phenotypic Correction of a Chronic Granulomatous Disease Mutation in Human iPS Cells, *Experimental Hematology*, 43(10): 838-848, 2015.

Li, et al., "Therapeutic Level CRISPR-Oligomer-Mediated Correction of X-CGD Patient Hematopoietic Stem Cells Using Non-Viral, cGMP Compliant, Scalable, and Closed System," *Molecular Therapy*, 24(Suppl. 1): S18, 2016.

Office Action Issued in Corresponding Singapore Patent Application No. 11201900447S, dated Apr. 7, 2020.

Cox et al., "Therapeutic genome editing: prospects and challenges", Nat Med., 21(2):121-131, 2015.

Dever et al., "CRISPR/Cas9 p-globlin Gene Targeting in Human Hematopoietic Stem Cells" Nature, 2016, 539(7629):384-389.

Hamar and Kultz, "An Efficient vector-based CRISPR/Cas9 system in an Oreochromis mossambicus cell line using endogenous promoters", Sci Rep, 11:7854, 2021.

Hendel et al., "Chemically modified guide RNAs enhanced CRISPR-Cas Genome editing in human primary cells" Nat. Biotechnol., 2015, 33(9):985-989.

Hsu et al., "DNA targeting specific of RNA—guided Cas9 nucleases", Nat Biotechnol, 31(9):827-832, 2013.

Jensen et al., "An update on targeted gene repair in mammalian cells: methods and mechanisms" Journal of Biomedical Science, 2011, 18(10), 14 pages.

Kosicki et al., "Repair of double-strand breaks induced by CRISPR Cas9 leads to large deletions and complex rearrangements", Nat Biotechnol, 36(8):765-771, 2018.

Lee et al., "Developing genetically engineered mouse models using engineered nucleases: Current status, challenges, and the way forward", Drug Discovery Today: Disease Models, 20:13-20, 2016.

Li et al., "Non-viral delivery systems for CRISPR/Cas9-based genome editing: Challenges and opportunities", Biomaterials, 171:207-218, 2018.

Zhao et al., "A Flow-Through Cell Electroporation Device for Rapidly and Efficiently Transfecting Massive Amounts of Cells in vitro and ex vivo" Sci. Rep. 6, 18469, doi:10.1038/srep18469 (2016).

Trickett & Kwan "T cell stimulation and expansion using anti-CD3/CD28 beads" *Journal of Immunological Methods* 275 (2003) 251-255.

Tendeloo et al., "High-level transgene expression in primary human T lymphocytes and adult bone marrow CD34+ cells via electroporation-mediated gene delivery", *Gene Therapy*, 7:1431-1437, 2000.

Goffinet and Keppler, "Efficient nonviral gene delivery into primary lymphocytes from rats and mice", *FASEB J.*, 20 (3):500-2, 2006.

\* cited by examiner

Donor DNA:
atggtgcatctgactcctgTAGtggagaagtctgccgttact

Target genomic DNA:
atggtgcatctgactcctgtggagaagtctgccgttact taccacgtagactgaggacacctcttcagacggcaatga

FIG. 10A

Donor DNA:
atggtgcatctgactcctgAggagaagtctgccgttact

Target genomic DNA:
atggtgcatctgactcctgtggagaagtctgccgttact taccacgtagactgaggacacctcttcagacggcaatga

FIG. 10B

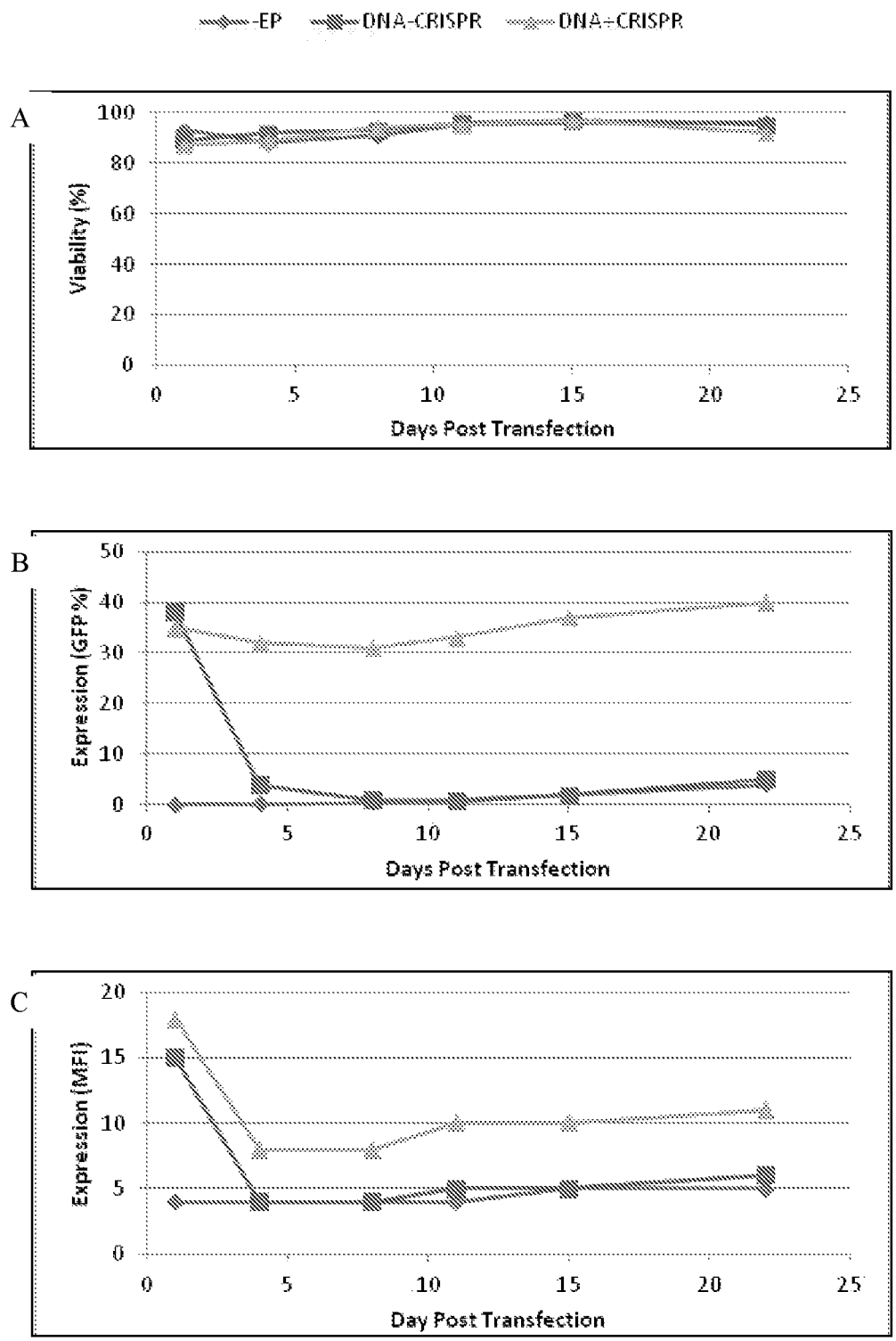
FIG. 13A-C

SEQUENCE LISTING

<160> NUMBER OF SEQ ID NOS: 20

<210> SEQ ID NO 1
<211> LENGTH: 11
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(8)
<223> OTHER INFORMATION: n is a, c, g, or t

<400> SEQUENCE: 1
gacnnnnngt c                                                                11

<210> SEQ ID NO 2
<211> LENGTH: 13
<212> TYPE: DNA
<213> ORGANISM: Artificial Sequence
<220> FEATURE:
<223> OTHER INFORMATION: Synthetic Primer

```
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (11)..(11)
<223> OTHER INFORMATION: Y is C or T
<220> FEATURE:
<221> NAME/KEY: misc_feature
<222> LOCATION: (13)..(13)
<223> OTHER INFORMATION: n is a, c, g, or t

<400> SEQUENCE: 2
nacnnnngta ycn                                                              13

<210> SEQ ID NO 3
<211> LENGTH: 12
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(9)
<223> OTHER INFORMATION: n is a, c, g, or t

<400> SEQUENCE: 3
cgannnnnnt gc                                                               12

<210> SEQ ID NO 4
<211> LENGTH: 11
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(8)
<223> OTHER INFORMATION: n is a, c, g, or t

<400> SEQUENCE: 4
gccnnnnngg c                                                                11

<210> SEQ ID NO 5
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(7)
<223> OTHER INFORMATION: n is a, c, g, or t

<400> SEQUENCE: 5 gatnnnnatc                                                                  10

<210> SEQ ID NO 6
<211> LENGTH: 11
<212> TYPE: DNA
<213> ORGANISM: Artificial Sequence
<220> FEATURE:
<223> OTHER INFORMATION: Synthetic Primer
```

```
<220> FEATURE:
<221> NAME/KEY: misc_feature
<222> LOCATION: (3)..(9)
<223> OTHER INFORMATION: n is a, c, g, or t

<400> SEQUENCE: 6
ccnnnnnnng g                                                              11

<210> SEQ ID NO 7
<211> LENGTH: 11
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(8)
<223> OTHER INFORMATION: n is a, c, g, or t

<400> SEQUENCE: 7 gcannnntg c                                                               11

<210> SEQ ID NO 8
<211> LENGTH: 12
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(9)
<223> OTHER INFORMATION: n is a, c, g, or t

<400> SEQUENCE: 8
ccannnnnnt gg                                                             12

<210> SEQ ID NO 9
<211> LENGTH: 12
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(9)
<223> OTHER INFORMATION: n is a, c, g, or t

<400> SEQUENCE: 9
gacnnnnnng tc                                                             12

<210> SEQ ID NO 10
<211> LENGTH: 11
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(8)
<223> OTHER INFORMATION: n is a, c, g, or t

<400> SEQUENCE: 10
cctnnnnnag g                                                              11

<210> SEQ ID NO 11
<211> LENGTH: 10
<212> TYPE: DNA
<213> ORGANISM: Artificial Sequence
```

```
<220> FEATURE:
<223> OTHER INFORMATION: Synthetic Primer
<220> FEATURE:
<221> NAME/KEY: misc_feature
<222> LOCATION: (6)..(10)
<223> OTHER INFORMATION: n is a, c, g, or t

<400> SEQUENCE: 11 gagtcnnnnn                                                                          10

<210> SEQ ID NO 12
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(3)
<223> OTHER INFORMATION: Y is C or T
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (8)..(8)
<223> OTHER INFORMATION: R is A or G

<400> SEQUENCE: 12 caynnnnrtg                                                                          10

<210> SEQ ID NO 13
<211> LENGTH: 11
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (3)..(9)
<223> OTHER INFORMATION: n is a, c, g, or t

<400> SEQUENCE: 13
gcnnnnnnng c                                                                        11

<210> SEQ ID NO 14
<211> LENGTH: 11
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(8)
<223> OTHER INFORMATION: n is a, c, g, or t

<400> SEQUENCE: 14
ccannnnntg g                                                                        11

<210> SEQ ID NO 15
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(7)
<223> OTHER INFORMATION: n is a, c, g, or t
```

```
<400> SEQUENCE: 15 gacnnnngtc                                                          10

<210> SEQ ID NO 16
<211> LENGTH: 13
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (5)..(9)
<223> OTHER INFORMATION: n is a, c, g, or t

<400> SEQUENCE: 16
ggccnnnnng gcc                                                      13

<210> SEQ ID NO 17
<211> LENGTH: 15
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(12)
<223> OTHER INFORMATION: n is a, c, g, or t

<400> SEQUENCE: 17
ccannnnnnn nntgg                                                    15

<210> SEQ ID NO 18
<211> LENGTH: 10
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(7)
<223> OTHER INFORMATION: n is a, c, g, or t

<400> SEQUENCE: 18 gaannnnttc                                                          10

<210> SEQ ID NO 19
<211> LENGTH: 38
<212> TYPE: DNA
<213> ORGANISM: Artificial Sequence
<220> FEATURE:
<223> OTHER INFORMATION: Synthetic Primer

<400> SEQUENCE: 19
ttaatacgac tcactatagg ggccactagg gacaggat                           38

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
aaaagcaccg actcggtgcc                                               20
```

METHODS FOR MODIFYING GENOMIC DNA

CROSS-REFERENCE TO RELATED APPLICATIONS

This application is a U.S. National Phase Application under 35 U.S.C. § 371 of PCT Application No. PCT/US2016/027253, filed Apr. 13, 2016, which claims the benefit of U.S. Provisional Application No. 62/146,618, filed Apr. 13, 2015, the entire contents of which applications are incorporated herein by reference.

BACKGROUND OF THE INVENTION

1. Field of the Invention

The present invention relates generally to the field of biotechnology. More particularly, it concerns novel methods and compositions for modifying genomic DNA.

2. Description of Related Art

Targeted genomic modification has tremendous potential for treating disease. Modifying DNA at a targeted site or site-specific transgene integration may provide for more effective gene therapy approaches. However, current genome engineering approaches provide very low efficiency of repair or editing and have the potential to introduce harmful or undesired DNA sequences and outcomes.

Current therapeutic approaches to gene therapy employ the use of viral vectors for gene transfer. However, gene therapeutic methods involving viral vectors have the disadvantage of introducing viral sequences into a human host, which may trigger host immunogenicity. Non-viral methods exist for gene therapy, but their use in a clinical setting is hindered because of either their low efficiency, toxicity, or lack of specificity.

More efficient approaches for genome engineering will also provide advances in ex vivo therapy, since one could isolate cells from a patient, modify the genome to correct a mutation or site-specifically integrate a transgene, and transplant the patient's own cells back in to achieve a therapeutic effect. Current methods are either too inefficient or too toxic to achieve these results. There is need in the field for a technology that allows for site-directed genomic DNA modification that is efficient, non-toxic, and stable.

SUMMARY OF THE INVENTION

Compositions and methods concern the sequence modification of an endogenous target genomic DNA sequence. Certain aspects relate to a method for site-specific sequence modification of a target genomic DNA region in cells comprising: contacting the cells with an activating composition; transfecting the cells with a transfection composition comprising (a) donor DNA and (b) a DNA digesting agent. The donor DNA comprises two regions. One region is a homologous region comprising nucleic acid sequence homologous to the target genomic DNA region and the other region is a sequence modification region. In the above-described method, the genomic DNA sequence is modified specifically at the target genomic DNA region.

The term "sequence modification" is a change to the DNA sequence and can include an addition, a change, or a deletion to or of the endogenous genomic DNA sequence. In terms of addition, the sequence modification may be the integration of a transgene into a target genomic site. For example, for a target genomic sequence, the donor DNA comprises a sequence complementary, identical, or homologous to the target genomic sequence and a sequence modification region. The a sequence modification region is typically located between the homologous ends. The sequence modification is not complementary to the target genomic sequence and contains an alteration of the target genomic sequence.

The donor DNA described herein comprises a sequence homologous, identical, or complimentary to the target genomic DNA sequence and a sequence modification of the target genomic DNA sequence.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand.

"Homology" or "identity" or "similarity" refers to sequence similarity between two peptides or between two nucleic acid molecules. The term "homologous region" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology.

The term "transfecting" refers to a methods for introducing bio-active materials, such as nucleic acids, proteins, enzymes, or small molecules, into a cell. The nucleic acids may be DNA, delivered as plasmid or oligomer, and/or RNA or combinations thereof.

The term "electroporation" refers to a method of transfection in which an externally applied electrical field is applied to the cell. In certain embodiments, the electroporation method used is static electroporation.

In certain embodiments, the transfection method used is electroporation. In a further embodiment, the electroporation method is flow electroporation. Flow electroporation, which refers to a process, comprising: transferring a suspension of cells and loading molecules into an apparatus comprised of a fluid chamber or fluid flow path; the said fluid chamber or fluid flow path being comprised of electrodes disposed along sides of the fluid chamber or fluid flow path and configured to subject biological particles within the fluid chamber fluid flow path to an electric field suitable for electroporation; and transferring the electroporated cell suspension out of the apparatus. This method is particularly effective for large scale volume of cells. Static electroporation, by contrast, involves electroporation of a set and limited volume of cells due to constraints associated with moving electricity across liquid and the distance between opposing electrodes.

In certain aspects, transfecting the expression construct into cells comprises flowing a suspension of the cells through an electric field in a flow chamber, the electric field being produced by opposing oppositely charged electrodes at least partially defining the flow chamber, wherein thermal resistance of the flow chamber is less than approximately 10° C. per Watt. In other certain aspects transfecting the cells comprises employing a flow electroporation device comprising a chamber for containing a suspension of cells to be electroporated; the chamber being at least partially defined by opposing oppositely chargeable electrodes; and wherein the thermal resistance of the chamber is less than approximately 10° C. per Watt.

In certain aspects, transfecting the expression construct into cells comprises electroporating or exposing a suspension of the cells to an electric field in a chamber, the electric field being produced by opposing oppositely charged electrodes at least partially defining the chamber, wherein thermal resistance of the chamber is less than approximately 10° C. per Watt. In other certain aspects transfecting the cells comprises employing an electroporation device comprising a chamber for containing a suspension of cells to be electroporated; the chamber being at least partially defined by opposing oppositely chargeable electrodes; and wherein the thermal resistance of the chamber is less than approximately 10° C. per Watt.

In certain aspects, the thermal resistance of the chamber is approximately 0.1° C. per Watt to 10° C. per Watt. For example, the thermal resistance of the chamber may be approximately 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C. per Watt, or any thermal resistance derivable therein.

The opposing oppositely chargeable electrodes may be spaced from each other at least 1 mm, at least 2 mm, at least 3 mm, or any distance or range derivable therein. In any of the disclosed embodiments, the chamber may have a ratio of combined electrode surface in contact with buffer to the distance between the electrodes of approximately 1 to 100 cm. For example, the ratio may be approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value or range derivable therein. In certain aspects, the chamber has a ratio of combined electrode surface in contact with buffer to the distance between the electrodes of approximately 1 to 100 cm, and the opposing oppositely chargeable electrodes are spaced from each other at least 1 mm. In other aspects, the chamber has a ratio of combined electrode surface in contact with buffer to the distance between the electrodes of approximately 1 to 100 cm, and the opposing oppositely chargeable electrodes are spaced from each other at least 3 mm. In even further aspects, the chamber has a ratio of combined electrode surface in contact with buffer to the distance between the electrodes of approximately 1 to 100 cm, and the opposing oppositely chargeable electrodes are spaced from each other approximately 3 mm to approximately 2 cm. For example, the opposing oppositely chargeable electrodes may be spaced from each other approximately 3, 4, 5, 6, 7, 8, 9, or 10 mm, or any distance derivable therein, or the opposing oppositely chargeable electrodes may be spaced from each other approximately 1.0, 1.1, 1.2, 1.3, 1.4, 1.5, 1.6, 1.7, 1.8, 1.9, or 2.0 cm, or any distance derivable therein. In some aspects of these embodiments, the cells electroporated are not substantially thermally degraded thereby.

In any of the disclosed embodiments, the chamber may have a ratio of combined electrode surface in contact with buffer to the distance between the electrodes of approximately 1 to 100 cm. For example, the ratio may be approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value or range derivable therein. In certain aspects, the chamber has a ratio of combined electrode surface in contact with buffer to the distance between the electrodes of approximately 1 to 100 cm, and the opposing oppositely chargeable electrodes are spaced from each other at least 1 mm. In other aspects, the chamber has a ratio of combined electrode surface in contact with buffer to the distance between the electrodes of approximately 1 to 100 cm, and the opposing oppositely chargeable electrodes are spaced from each other at least 3 mm. In even further aspects, the chamber has a ratio of combined electrode surface in contact with buffer to the distance between the electrodes of approximately 1 to 100 cm, and the opposing oppositely chargeable electrodes are spaced from each other approximately 3 mm to approximately 2 cm. For example, the opposing oppositely chargeable electrodes may be spaced from each other approximately 3, 4, 5, 6, 7, 8, 9, or 10 mm, or any distance derivable therein, or the opposing oppositely chargeable electrodes may be spaced from each other approximately 1.0, 1.1, 1.2, 1.3, 1.4, 1.5, 1.6, 1.7, 1.8, 1.9, or 2.0 cm, or any distance derivable therein. In some aspects of these embodiments, the cells electroporated are not substantially thermally degraded thereby.

In any of the disclosed embodiments, the device may further comprise a cooling element to dissipate heat. For example, the cooling element may comprise a thermoelectric cooling element. As another example, the cooling element may comprise a cooling fluid flowing in contact with the electrode. As yet another example, the cooling element may comprise a heat sink operatively associated with the electrode. The heat resistance of the chamber may be less than approximately 3° C. per Watt. In some embodiments, the heat resistance of the chamber is between approximately 0.5° C. per Watt and 4° C. per Watt, or the heat resistance of the chamber is between approximately 1° C. per Watt and 3°

C. per Watt. For example, the heat resistance of the chamber may be approximately 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0° C. per Watt, or any value derivable therein.

In certain methods involving transfecting cells by electroporation, the method involves exposing a suspension of cells to an electric field having a strength of greater than 0.5 kV/cm. For example, the electric field may have a strength of greater than approximately 3.5 kV/cm. In certain aspects the electric field has a strength of greater than approximately 0.5, 1.0, 1.5, 2.0, 2.5, 3.0, or 3.5 kV/cm, or any value derivable therein.

In some embodiments, transfecting the cells comprises employing a flow electroporation device comprising: walls defining a flow channel having an electroporation zone configured to receive and to transiently contain a continuous flow of a suspension of cells to be electroporated; an inlet flow portal in fluid communication with the flow channel, whereby the suspension can be introduced into the flow channel through the inlet flow portal; an outlet flow portal in fluid communication with the flow channel, whereby the suspension can be withdrawn from the flow channel through the outlet portal; the walls defining the flow channel within the electroporation zone comprising a first electrode forming a substantial portion of a first wall of the flow channel and a second electrode forming a substantial portion of a second wall of the flow channel opposite the first wall, the first and second electrodes being such that when placed in electrical communication with a source of electrical energy an electric field is formed therebetween through which the suspension can flow; and wherein the thermal resistance of the flow channel is less than approximately 10° C. per Watt.

In certain such embodiments, the first and second electrodes or opposing oppositely chargeable electrodes are spaced from each other at least 1 mm. Moreover, the chamber may have a ratio of combined electrode surface in contact with buffer to the distance between the electrodes of approximately 1 to 100 cm. In particular embodiments, the chamber may have a ratio of combined electrode surface in contact with buffer to the distance between the electrodes of approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value or range derivable therein. In certain embodiments, the cells electroporated by the electroporation methods described herein are not substantially thermally degraded thereby. In certain embodiments described herein, the chamber is a flow chamber.

In some aspects, the electroporation device comprises a chamber for containing a suspension of cells to be electroporated; the chamber being at least partially defined by opposing oppositely chargeable electrodes; and wherein the chamber has a ratio of combined electrode surface in contact with buffer to the distance between the electrodes of approximately 1 to 100 cm. In particular aspects, the ratio is approximately 1 to 70 cm. In other particular aspects, the ratio is approximately 1 to 50 cm. For example, the ratio may be approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value derivable therein. In certain embodiments described herein, the chamber is a flow chamber.

In some embodiments, the flow electroporation device comprises walls defining a flow channel configured to receive and to transiently contain a continuous flow of a suspension of cells to be electroporated; an inlet flow portal in fluid communication with the flow channel, whereby the suspension can be introduced into the flow channel through the inlet flow portal; an outlet flow portal in fluid communication with the flow channel, whereby the suspension can be withdrawn from the flow channel through the outlet portal; the walls defining the flow channel comprising a first electrode forming at least a portion of a first wall of the flow channel and a second electrode forming at least a portion of a second wall of the flow channel opposite the first wall, the first and second electrodes being such that when placed in electrical communication with a source of electrical energy an electric field is formed therebetween through which the suspension can flow; and wherein the thermal resistance of the flow channel is less than approximately 10° C. per Watt. In certain aspects, the thermal resistance of the flow channel is approximately 0.1° C. per Watt to 10° C. per Watt. For example, the thermal resistance of the flow channel may be approximately 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C. per Watt, or any thermal resistance derivable therein. The first and second electrodes may be spaced from each other at least 1 mm, at least 2 mm, at least 3 mm, or any distance or range derivable therein. In any of the disclosed embodiments, the flow chamber may have a ratio of combined electrode surface in contact with buffer to the distance between the electrodes of approximately 1 to 100 cm. For example, the ratio may be approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value or range derivable therein. In certain aspects, the flow chamber has a ratio of combined electrode surface in contact with buffer to the distance between the electrodes of approximately 1 to 100 cm, and the first and second electrodes are spaced from each other at least 1 mm. In other aspects, the flow chamber has a ratio of combined electrode surface in contact with buffer to the distance between the electrodes of approximately 1 to 100 cm, and the first and second electrodes are spaced from each other at least 3 mm. In even further aspects, the flow chamber has a ratio of combined electrode surface in contact with buffer to the distance between the electrodes of approximately 1 to 100 cm, and the first and second electrodes are spaced from each other approximately 3 mm to approximately 2 cm. For example, the first and second electrodes may be spaced from each other approximately 3, 4, 5, 6, 7, 8, 9, or 10 mm, or any distance derivable therein, or the first and second electrodes may be spaced from each other approximately 1.0, 1.1, 1.2, 1.3, 1.4, 1.5, 1.6, 1.7, 1.8, 1.9, or 2.0 cm, or any distance derivable therein. In some aspects of these embodiments, the cells electroporated in the flow channel are not substantially thermally degraded thereby.

In certain disclosed methods and devices, the thermal resistance of the chamber is approximately 0.1° C. per Watt to approximately 4° C. per Watt. In some aspects, the thermal resistance of the chamber is approximately 1.5° C. per Watt to approximately 2.5° C. per Watt. For example, the thermal resistance of the chamber may be approximately 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0° C. per Watt, or any resistance derivable therein.

In certain disclosed methods and devices, the flow electroporation device comprises: walls defining a flow channel configured to receive and to transiently contain a continuous flow of a suspension comprising particles; an inlet flow portal in fluid communication with the flow channel, whereby the suspension can be introduced into the flow channel through the inlet flow portal; an outlet flow portal in fluid communication with the flow channel, whereby the suspension can be withdrawn from the flow channel through the outlet flow portal; the walls defining the flow channel comprising a first electrode plate forming a first wall of the flow channel and a second electrode plate forming a second wall of the flow channel opposite the first wall; wherein the area of the electrodes contact with the suspension, and the distance between the electrodes is chosen so that the thermal resistance of the flow channel is less than approximately 4° C. per Watt; the paired electrodes placed in electrical communication with a source of electrical energy, whereby an electrical field is formed between the electrodes; whereby the suspension of the particles flowing through the flow channel can be subjected to an electrical field formed between the electrodes. In certain aspects, the electrode plates defining the flow channel further comprise a gasket formed from an electrically non-conductive material and disposed between the first and second electrode plates to maintain the electrode plates in spaced-apart relation, the gasket defining a channel therein forming opposed side walls of the flow channel. The gasket may, for example, form a seal with each of the first and second electrode plates. In some embodiments, the device comprises a plurality of flow channels, and the gasket comprises a plurality of channels forming opposed side walls of each of the plurality of channels. In some aspects, one of the inlet flow portal and the outlet flow portal comprises a bore formed in one of the electrode plates and in fluid communication with the flow channel. The other of the inlet flow portal and the outlet flow portal may comprise a bore formed in the one of the electrode plates and in fluid communication with the flow channel. In certain aspects, the inlet flow portal and the outlet flow portal comprise a bore formed in the other of the electrode plates and in fluid communication with the flow channel. In any of the disclosed embodiments, the device may further comprise a cooling element operatively associated with the flow channel to dissipate heat. For example, the cooling element may comprise a thermoelectric cooling element. As another example, the cooling element may comprise a cooling fluid flowing in contact with the electrode. As yet another example, the cooling element may comprise a heat sink operatively associated with the electrode. The heat resistance of the flow channel may be less than approximately 3° C. per Watt. In some embodiments, the heat resistance of the flow channel is between approximately 0.5° C. per Watt and 4° C. per Watt, or the heat resistance of the flow channel is between approximately 1° C. per Watt and 3° C. per Watt. For example, the heat resistance of the flow channel may be approximately 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0° C. per Watt, or any value derivable therein.

In certain disclosed methods and devices, the first electrode may comprise an elongated, electrically conductive structure, wherein the second electrode comprises a tubular, electrically conductive structure; wherein the electrodes are concentrically arranged such that the second, tubular electrode surrounds the first electrode in spaced-apart relation thereto; and wherein the flow channel is disposed within an annular space defined between the first and second electrodes. The electrodes may form at least a portion of the walls defining the flow channel. In some embodiments, concentric annular spacers for maintaining the first and second electrodes are in spaced-apart, concentric relation. In certain aspects, the device is arranged in series or in parallel with a second, like device.

In certain methods involving transfecting cells by flow electroporation, the flow channel has a thermal resistance of less than approximately 10° C. per Watt. In some methods involving transfecting the cells by flow electroporation, the method involves flowing a suspension of cells to be electroporated through a flow channel and exposing the suspension of to an electric field while flowing through the flow channel, the electric field having a strength of greater than 0.5 kV/cm. For example, the electric field may have a strength of greater than approximately 3.5 kV/cm. In certain aspects the electric field has a strength of greater than approximately 0.5, 1.0, 1.5, 2.0, 2.5, 3.0, or 3.5 kV/cm, or any value derivable therein.

In the disclosed embodiments regarding the flow electroporation device, it is specifically contemplated that parameters and parameter ranges described for flow electroporation are applicable to static electroporation devices used in the methods described herein. In specific embodiments, flow electroporation is used and static electroporation or non-flow electroporation is excluded. In a further specific embodiment, static electroporation is used and flow electroporation is excluded.

The methods described herein also encompass the use of other transfection methods known in the art such as chemical-based and non-chemical based transfection methods. Chemical-based transfection methods include, for example, calcium phosphate, dendrimers, lipofection, and cationic polymers such as DEAE-dextran or polyethylenimine. Non-chemical methods include cell squeezing, sonoporation, optical transfection, impalefection, and hydrodynamic delivery. Also included are particle-based methods such as the use of a gene gun, magnetofections (i.e. magnet-assisted transfection), and particle bombardment.

The methods described herein employ a cell-activating step. In some embodiments, this cell activating step is prior to the transfection of the cells. In some embodiments, the cells are transfected at a time period of less than seven days after contacting the cells with the activating composition. In some embodiments, the cells are transfected at a time period of less than 3 days after contacting the cells with the activating composition. In some embodiments, the cells are transfected at a time period of 2 days or less after contacting the cells with the activating composition. In some embodiments, the cells are transfected two days after contacting the cells with the activating composition. In some embodiments, the cells are transfected at a time period of less than 14, 13, 12, 11, 10, 9, 8, 7, 6, 5, 4, or 3 days after contacting the cells with the activating composition. In some embodiments, the cells are transfected at a time period of 10, 9, 8, 7, 6, 5, 4, 3, 2, or 1 days after contacting the cells with the activating composition.

In some embodiments, the DNA digesting agent is selected from a TALEN, transposase, integrase and nuclease. In some embodiments, the DNA digesting agent is encoded on one or more RNAs. In some embodiments, the DNA digesting agent is a nuclease. In some embodiments, the DNA digesting agent is Cas9. In some embodiments, the transfection composition further comprises CRISPR RNA. In some embodiments, the transfection composition further comprises a guide RNA. In some embodiments, the nuclease is a site-specific nuclease.

In some embodiments, the donor DNA is a plasmid. In some embodiments, the donor DNA is an oligo. In some embodiments, the donor DNA is a single-stranded oligo. The concentration of the donor DNA in the transfection composition may be from about 10 to about 1000 µg/mL or from about 10 to about 900, 800, 700, 600, 500, 400, 300, 200, 100, or 50 µg/mL or any derivable range therein.

Any of the disclosed methods may include a step employing limiting dilution of the transfected cells to obtain single cell colonies. As used herein, the term "limiting dilution" refers to the process of significantly diluting a cell culture, with the goal of achieving a single cell in each culture. When such an isolated, single cell reproduces, the resulting culture will contain only clones of the original cell. For example, a multi-well plate may be used to obtain single cell cultures or colonies. For example, limiting dilution may be employed for a patient cell derived iPS study (e.g. for repair of sickle cell patients). iPS cells, using limited dilution approach, can be modified to a corrected hemoglobin-expressing cell, isolated, and expanded for administration to the patient.

In any of the disclosed methods, a step may be employed comprising expanding a clonal isolated and selected cell to produce clonal cells with a particular genomic DNA sequence modification.

In disclosed methods involving the expansion of a clonal isolated cell, the expansion may be for large scale manufacturing. For example, the cells may be expanded in a volume of greater than 1 L, or the cells may be expanded in a volume of greater than 3 L. In certain aspects, the cells are expanded in a volume of greater than 1.0, 1.5, 2.0, 2.5, or 3.0 L, or any value derivable therein.

In any of the disclosed methods, a further step may be employed comprising freezing transfected and selected or screened cells. An even further step may also be employed, wherein previously frozen transfected and selected/screened cells are expanded.

In the disclosed methods, the cell culture may include any additional ingredients known to those of ordinary skill in the art, as would be readily selected by those of ordinary skill in the art based on the type of cell that is cultured. For example, the cells may be cultured in sodium butyrate or comparable salt. In some embodiments, the cells are cultured in serum-free media.

In the disclosed methods, a further step may be employed comprising expanding a clonal isolated and selected or screened cell to produce clonal cells having a genomic DNA sequence modification.

Further aspects relate to a method for producing a stable cell line comprising a genomic DNA sequence modification of a target genomic DNA sequence, the method comprising: contacting the cells with an activating composition; transfecting the cells with a transfection composition comprising (a) donor DNA and (b) a DNA digesting agent; wherein the donor DNA comprises: (i) a homologous region comprising nucleic acid sequence homologous to the target genomic DNA region; and (ii) a sequence modification region; and screening transfected cells for the genomic DNA sequence modification at the target genomic DNA region; isolating screened transfected cells by limiting dilution to obtain clonal cells; expanding isolated transfected cells to produce a stable cell line comprising the genomic DNA sequence modification.

The disclosure also provides for a cell line or transfected cell produced by the methods described herein.

A further aspect relates to a method of treating a subject having or suspected of having a disease or condition by administering an effective amount of a cell line or of transfected cells produced by the methods described herein.

Another aspect relates to a clinical research method comprising administering an effective amount of a cell line or of transfected cells produced by the methods described herein.

It is specifically contemplated that embodiments described herein may be excluded. It is further contemplated that, when a range is described, certain ranges may be excluded.

Further aspects relate to a method of treating a cancer in a subject in need thereof comprising contacting cells with an activating composition; transfecting the cells with a transfection composition comprising (a) donor DNA and (b) a DNA digesting agent; wherein the donor DNA comprises: (i) a homologous region comprising nucleic acid sequence homologous to the target genomic DNA region; and (ii) a chimeric antigen receptor (CAR); and wherein the genomic DNA sequence is modified specifically at the target genomic DNA region to integrate the CAR; and administering the cells to the patient. In some embodiments, the transfection composition is non-viral.

In some embodiments, the cells are autologous. In some embodiments, the cells are T cells or NK cells. Alternatively, the cells may be a host cell as defined throughout the application. In some embodiments, the cancer is a B-cell malignancy. In some embodiments, the cancer is leukemia. In some embodiments, the cancer is acute lymphoblastic leukemia. In some embodiments, the cells are isolated from the blood of the patient. In some embodiments, the cells are isolated from a genetically-matched donor. In some embodiments, the cells are donor cells. In some embodiments, the cells are isolated by apheresis. In some embodiments, the method further comprises isolating the cells from the patient.

Further aspects relate to a method for site-specific sequence modification of a target genomic DNA region in cells comprising: contacting the cells with an activating composition; transfecting the cells with a non-viral transfection composition comprising (a) donor DNA and (b) a DNA digesting agent; wherein the donor DNA comprises: (i) a homologous region comprising nucleic acid sequence homologous to the target genomic DNA region; and (ii) a sequence modification region; and wherein the genomic DNA sequence is modified specifically at the target genomic DNA region. In some embodiments, the cells are immune cells. In some embodiments, the immune cells are T cells. In some embodiments, the T cells are primary T cells. In some embodiments, the activating composition comprises anti-CD3 and anti-CD28 antibodies. In some embodiments, the transfection of the cells comprises flow electroporation of the cells.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

As used herein the specification, "a" or "an" may mean one or more. As used herein in the claim(s), when used in conjunction with the word "comprising", the words "a" or "an" may mean one or more than one.

The methods of the disclosure are described herein as comprising the recited elements or steps, but may also consist of the recited elements or steps. When the methods consist of the recited elements or steps, the methods exclude non-recited elements or steps. The methods of the disclosure may also "consist essentially of" the recited elements or steps. When the methods "consist essentially of" the recited elements or steps, the methods exclude elements or active ingredients that change the nature of the composition or steps that alter the outcome of the method.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the percentage of cells expressing GFP (R2) 1, 5, and 12 days post transfection by electroporation (or control no electroporation (−EP)) with plasmid GFP DNA (DNA-CRISPR) or with plasmid GFP DNA and the gRNA/Cas9 CRISPR complex targeting integration into the AAVS1 site (DNA+CRISPR). As shown in FIG. 1, 37% of cells transfected with the DNA+CRISPR maintained expression of GFP 12 days post transfection while only 0.8% of cells transfected with DNA-CRISPR maintained expression of GFP 12 days post transfection.

FIG. 2A-C demonstrates that the transfection of plasmid DNA induces cytotoxicity in expanded T cells.

FIG. 7 shows the percentage of cells expressing GFP (R2) 1, 4, and 11 days post transfection by electroporation (or control no electroporation (−EP)) with plasmid GFP DNA (DNA-CRISPR) or with plasmid GFP DNA and the gRNA/Cas9 CRISPR complex targeting integration into the AAVS1 site (DNA+CRISPR). As shown in FIG. 7, 4% of cells transfected with the DNA+CRISPR maintained expression of GFP 11 days post transfection while only 0.3% of cells transfected with DNA-CRISPR maintained expression of GFP 11 days post transfection.

FIG. 8 shows the percentage of cells expressing GFP (R2) 6 days post transfection by electroporation (or control no electroporation (−EP)) with plasmid GFP DNA (DNA-CRISPR) or with plasmid GFP DNA and the gRNA/Cas9 CRISPR complex targeting integration into the AAVS1 site (DNA+CRISPR). As shown in FIG. 8, 2.3% of cells transfected with the DNA+CRISPR maintained expression of GFP 6 days post transfection while 0% of cells transfected with DNA-CRISPR maintained expression of GFP 6 days post transfection.

FIG. 10A-B: Example donor DNA oligo with sequence modification region (uppercase and not shaded) and homologous region (lower case and shaded). FIG. 10A shows an example where a stop codon is inserted as an addition into a target genomic DNA. FIG. 10B shown an example where a single base is changed in the target genomic DNA.

FIG. 11: Example of targeted transgene integration: Depicted is an example in which the donor DNA is a double-stranded plasmid (only one strand of sequence is depicted for simplicity) with a sequence modification region of a 2000 bp transgene X and a homologous region, which is depicted as a sequence in lower cases and shaded. The plasmid may also contain additional plasmid sequences such a markers, origins of replication, and the like.

FIG. 13A-C: Targeted Integration of SA-2A-eGFP-PolyA in AAVS1 Site of K562 by mRNA-CRISPR and Donor Plasmid DNA (Without Selection): Shown is an analysis of the viability (A), GFP expression (B), and mean fluorescent intensity (C) of cells transfected with donor plasmid DNA (SA-2A-eGFP-PolyA) and (+) or (−) the CRISPR system, which targets the integration to the AAVS1 site of K562 cells. Only cells transfected with the donor DNA and CRISPR system exhibited stable GFP expression and mean fluorescence intensity at extended periods post transfection.

DESCRIPTION OF ILLUSTRATIVE EMBODIMENTS

Figure 1A:
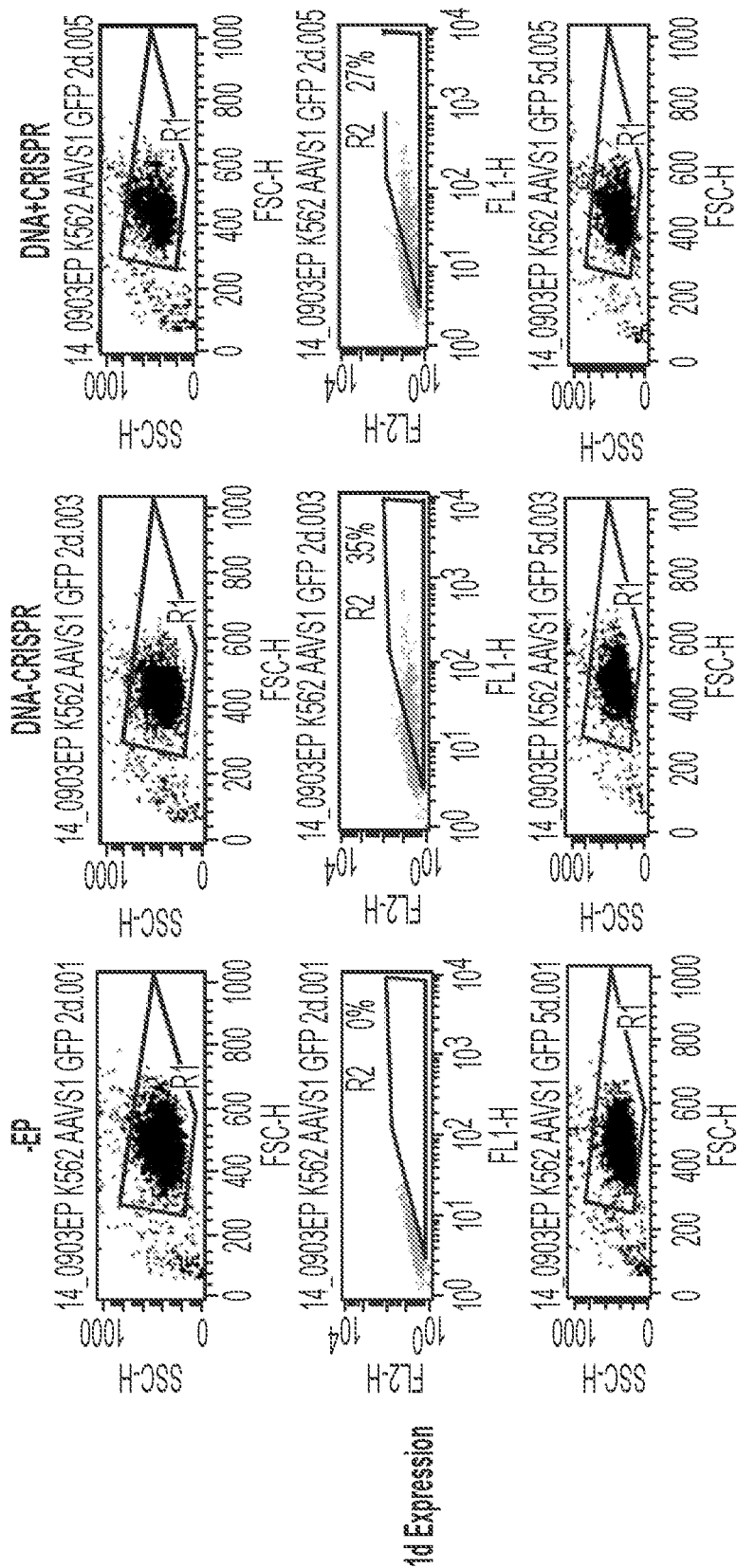
FIGS. 1A-1B: Targeted Integration of GFP in K562 by mRNA-CRISPR (gRNA/Cas9-AAVS1) and Plasmid GFP DNA.

Compositions and methods concern the sequence modification of an endogenous target genomic DNA sequence. Certain aspects relate to a method for site-specific sequence modification of a target genomic DNA region in cells comprising: contacting the cells with an activating composition; transfecting the cells with a transfection composition comprising (a) donor DNA and (b) a DNA digesting agent. The donor DNA comprises two regions. One region is a homologous region comprising nucleic acid sequence homologous to the target genomic DNA region and the other region is a sequence modification region. In the above-described method, the genomic DNA sequence is modified specifically at the target genomic DNA region.

Applicants found that adding an activation step prior to cell transfection overcame the toxicity associated with the delivery of plasmid DNA in traditional genome engineering approaches. One additional advantage to this method is the lack of random integration of transgene sequences. Random integration of target sequences may cause undesired effects due to the inability to control the integration site. These undesired effects include the inactivation of host genes, silencing or lack of adequate expression of the transgene, and the requirement for extensive screening procedures to determine the integration site of the transgene. It is contemplated that this method can be used as a unique gene therapy approach for cells which exhibit toxicity to plasmid DNA. Such cells include primary cells, stem cells, primary T cells, hematopoietic progenitor cells, and other cells known in the art and described herein as difficult-to-transfect cells.

Nucleic Acids

B. Donor DNA

Embodiments concern the sequence modification of target genomic DNA sequences by transfecting cells with a composition comprising donor DNA and a DNA digesting agent.

The term "endogenous genomic DNA" refers to the chromosomal DNA of the cell. The term "target genomic DNA sequence" refers to an endogenous genomic DNA site in which a DNA sequence modification is directed to. The DNA sequence modification may be one that changes one or more bases of the target genomic DNA sequence at one specific site or multiple specific sites. A change may include changing 1, 2, 3, 4, 5, 10, 15, 20, 25, 30, 35, 40 or more base pairs of the target genomic DNA sequence to a different 1, 2, 3, 4, 5, 10, 15, 20, 25, 30, 35, 40 or more base pairs. A deletion may be a deletion of 1, 2, 3, 4, 5, 10, 15, 20, 25, 30, 40, 50, 75, 100, 150, 200, 300, 400, or 500 base pairs. An addition may be the addition of 1, 2, 3, 4, 5, 10, 15, 20, 25, 30, 35, 40 or more base pairs. A sequence modification may be classified as a change and deletion, a change and addition, etc. . . . if the sequence modification alters the target genomic DNA in multiple ways. In one embodiment, the sequence modification is a stop codon. In a further embodiment, the DNA sequence modification is one or more stop codons. In further embodiments, the DNA sequence modification is 1, 2, 3, 4, 5, or 10 stop codons. When the sequence modification is a stop codon, efficiency and/or reliability of gene editing may be increased.

When the sequence modification is the integration of a transgene, the transgene may be the length of a typical gene sequence or the typical length of the coding region of a gene. In some embodiments, the transgene in the sequence modification region is 100-10000 nucleic acids in length. In further embodiments, the transgene is 500-5000 nucleic acids in length. In some embodiments, the transgene is 1000-3000 or 1000-5000 nucleic acids in length.

The DNA sequence modification may also be the site-specific integration of a transgene. The term transgene refers to a gene or genetic material that is transferred by way of genetic engineering into a host genome. The transgene may be expression of a therapeutic gene that is mutated or deficient in the host. The transgene may also comprise a marker such as GFP or a cell surface marker that allows for the tracking of transfected cells in vivo or in vitro.

The donor DNA may be plasmid DNA, a linearized DNA fragment, or an oligo. Plasmid DNA refers to a circular piece of DNA. The plasmid may contain one or more transgene. For example, the plasmid may encode for a DNA digesting agent that site-specifically makes a break in the endogenous genomic DNA and a transgene that integrates into the genomic DNA at or near the breakage point.

The term "oligo" or "oligonucleotide" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine. In some embodiments, the term oligo is used to define a nucleic acid having 150 bases or less. In some embodiments, the term oligo is used to define a nucleic acid having 100 or 50 or 25 bases or less.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules.

Unless otherwise specified or required, any embodiment of this invention that is a polynucleotide encompasses both the double-stranded form and each of two complementary single-stranded forms known or predicted to make up the double-stranded form.

Biologically equivalent polynucleotides are those having the specified percent homology and encoding a polypeptide having the same or similar biological activity.

In certain embodiments, the homologous region of the donor DNA is 100% homologous. In further embodiments, the homologous region of the donor DNA is 85, 90, 95, or 99% homologous.

In certain embodiments, the donor DNA comprises at least about 10, 12, 14, 16, 18, 20, 22, 24, 26, 28, 30, 32, 34, 36, 38, 40, 42, 44, 46, 48, 50, 100, 200, 300, 400, 500, 600, 700, 800, 1000, 1200, 1400, or 1600 (or any range derivable therein) of nucleic acids of sequence that is homologous to the target genomic DNA sequence. In some embodiments, the donor DNA comprises at least about 20 nucleic acids of sequence that are identical to the genomic DNA sequence. In this context, the term "identical sequence" refers to sequence that exactly matches the sequence of the genomic DNA. The identical sequence may be in a region that is on the 5' end of the DNA sequence modification and in a region that is on the 3' end of a DNA sequence modification. By way of illustrative example, when the donor DNA comprises at least 20 nucleic acids of homologous sequences, the donor DNA may comprise, for example, 10 nucleic acids of homologous sequence on each side of the sequence modification. Similarly, donor DNA comprising 10 nucleic acids of homologous sequences may comprise, for example, 5 nucleic acids of complimentary sequence on each side of the sequence modification. In some embodiments, the homologous region comprises 1600 nucleic acids that are homologous to the target genomic sequence. In some embodiments, the donor DNA comprises 800 nucleic acids of homologous region at the 5' end of the sequence modification region 800 nucleic acids of homologous region at the 3' end of the sequence modification region.

When the donor DNA is a single-stranded DNA oligo, it may be from about 10, 20, 25, 30, 35, 40, 50, 60, 70, 80, 90, 100, 150, 200, 250, 300, 350, 400, 450, 500, 550, or 600 nucleic acids to about 50, 75, 100, 125, or 150 nucleic acids in length, or any derivable range thereof. In certain embodiments, the oligo is more than 20 nucleic acids, or more than 21, 22, 23, 24, 25, 30, or 40 nucleic acids. In specific embodiments, the oligo is from about 30 to 150 nucleic acids, from about 25 to about 150 nucleic acids, from about 25 to about 150 nucleic acids, from about 25 to about 100 nucleic acids, or from about 40 to about 100 nucleic acids.

The concentration of the donor DNA during the transfection procedure may be the final concentration of the donor DNA in the transfection composition and/or transfection sample container. The donor DNA concentration may be from about 10, 20, 30, 50, 75, 100, 150, 200, 250, 300 to about 350, 400, 500, 1000, 1500, 2000, 3000, 4000, or 5000 μg/mL or any range derivable therein. In certain embodiments, the concentration of the donor DNA is at least 30 μg/mL. In further embodiments, the concentration of the donor DNA is at least 10, 15, 20, 25, 30, 35, 40, 45, 50, 55, 60, 65, 70, 75, 80, 85, 90, 95, 100, 150, or 200 μg/mL.

C. DNA Digesting Agent

The present invention provides methods for modifying a target genomic DNA sequence by transfecting the cells by transfection with donor DNA and a DNA digesting agent. The term "DNA digesting agent" refers to an agent that is capable of cleaving bonds (i.e. phosphodiester bonds)

between the nucleotide subunits of nucleic acids. In a specific embodiment, the DNA digesting agent is encoded on RNA. In other embodiments, the DNA digesting agent is a protein, an enzyme, or a small molecule mimic that has enzymatic activity. In some embodiments, the DNA digesting agent is encoded on DNA. In a specific embodiment, the DNA digesting agent is encoded on plasmid DNA. In some embodiments, the DNA digesting agent and the donor DNA are encoded on the same plasmid.

In one embodiment, the DNA digesting agent is a transposase. For example, a synthetic DNA transposon (e.g. "Sleeping Beauty" transposon system) designed to introduce precisely defined DNA sequences into the chromosome of vertebrate animals can be used. The Sleeping Beauty transposon system is composed of a Sleeping Beauty (SB) transposase and a transposon that was designed to insert specific sequences of DNA into genomes of vertebrate animals. DNA transposons translocate from one DNA site to another in a simple, cut-and-paste manner. Transposition is a precise process in which a defined DNA segment is excised from one DNA molecule and moved to another site in the same or different DNA molecule or genome.

As do all other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. All of the DNA transposons identified in the human genome and other mammalian genomes are non-autonomous because even though they contain transposase genes, the genes are non-functional and unable to generate a transposase that can mobilize the transposon.

In a further embodiment, the DNA digesting agent is an integrase. For example, The phiC31 integrase is a sequence-specific recombinase encoded within the genome of the bacteriophage phiC31. The phiC31 integrase mediates recombination between two 34 base pair sequences termed attachment sites (att), one found in the phage and the other in the bacterial host. This serine integrase has been show to function efficiently in many different cell types including mammalian cells. In the presence of phiC31 integrase, an attB-containing donor plasmid can be unidirectional integrated into a target genome through recombination at sites with sequence similarity to the native attP site (termed pseudo-attP sites). phiC31 integrase can integrate a plasmid of any size, as a single copy, and requires no cofactors. The integrated transgenes are stably expressed and heritable.

In a specific embodiment, the DNA digesting agent is a nuclease. Nucleases are enzymes that hydrolyze nucleic acids. Nucleases may be classified as endonucleases or exonucleases. An endonuclease is any of a group enzymes that catalyze the hydrolysis of bonds between nucleic acids in the interior of a DNA or RNA molecule. An exonuclease is any of a group of enzymes that catalyze the hydrolysis of single nucleotides from the end of a DNA or RNA chain. Nucleases may also be classified based on whether they specifically digest DNA or RNA. A nuclease that specifically catalyzes the hydrolysis of DNA may be referred to as a deoxyribonuclease or DNase, whereas a nuclease that specifically catalyses the hydrolysis of RNA may be referred to as a ribonuclease or an RNase. Some nucleases are specific to either single-stranded or double-stranded nucleic acid sequences. Some enzymes have both exonuclease and endonuclease properties. In addition, some enzymes are able to digest both DNA and RNA sequences. The term "nuclease" is used herein to generally refer to any enzyme that hydrolyzes nucleic acid sequences.

Optimal reaction conditions vary among the different nucleases. The factors that should be considered include temperature, pH, enzyme cofactors, salt composition, ionic strength, and stabilizers. Suppliers of commercially available nucleases (e.g., Promega Corp.; New England Biolabs, Inc.) provide information as to the optimal conditions for each enzyme. Most nucleases are used between pH 7.2 and pH 8.5 as measured at the temperature of incubation. In addition, most nucleases show maximum activity at 37° C.; however, a few enzymes require higher or lower temperatures for optimal activity (e.g., Taq I, 65° C.; Sma I, 25° C.). DNA concentration can also be a factor as a high DNA concentration can reduce enzyme activity, and DNA concentrations that are too dilute can fall below the $K_m$ of the enzyme and also affect enzyme activity.

Non-limiting examples of nucleases include, DNase I, Benzonase, Exonuclease I, Exonuclease III, Mung Bean Nuclease, Nuclease BAL 31, RNase I, Si Nuclease, Lambda Exonuclease, RecJ, and T7 exonuclease. DNase I is an endonuclease that nonspecifically cleaves DNA to release di-, tri- and oligonucleotide products with 5'-phosphorylated and 3'-hydroxylated ends. DNase I acts on single- and double-stranded DNA, chromatin, and RNA:DNA hybrids. Exonuclease I catalyzes the removal of nucleotides from single-stranded DNA in the 3' to 5' direction. Exonuclease III catalyzes the stepwise removal of mononucleotides from 3'-hydroxyl termini of duplex DNA. Exonuclease III also acts at nicks in duplex DNA to produce single-strand gaps. Single-stranded DNA is resistant to Exonuclease III. Mung Bean Nuclease degrades single-stranded extensions from the ends of DNA. Mung Bean Nuclease is also an RNA endonuclease. Nuclease BAL 31 degrades both 3' and 5' termini of duplex DNA. Nuclease BAL 31 is also a highly specific single-stranded endonuclease that cleaves at nicks, gaps, and single-stranded regions of duplex DNA and RNA. RNase I is a single strand specific RNA endonuclease that will cleave at all RNA dinucleotide. Si Nuclease degrades single-stranded DNA and RNA endonucleolytically to yield 5'-phosphoryl-terminated products. Double-stranded nucleic acids (DNA:DNA, DNA:RNA or RNA:RNA) are resistant to S1 nuclease degradation except with extremely high concentrations of enzyme. Lambda Exonuclease catalyzes the removal of 5' mononucleotides from duplex DNA. Its preferred substrate is 5'-phosphorylated double stranded DNA, although Lambda Exonuclease will also degrade single-stranded and non-phosphorylated substrates at a greatly reduced rate. Lambda Exonuclease is unable to initiate DNA digestion at nicks or gaps, RecJ is a single-stranded DNA specific exonuclease that catalyzes the removal of deoxy-nucleotide monophosphates from DNA in the 5' to 3' direction. T7 exonuclease catalyzes the removal of 5' mononucleotides from duplex DNA. T7 Exonuclease catalyzes nucleotide removal from the 5' termini or at gaps and nicks of double-stranded DNA.

Restriction endonucleases are another example of nucleases that may be used in connection with the methods of the present invention. Non-limiting examples of restriction endonucleases and their recognition sequences are provided in Table 1.

TABLE 1

Recognition Sequences for Restriction Endonucleases.

| ENZYME | RECOGNITION SEQUENCE | SEQ ID NO. |
|---|---|---|
| AatII | GACGTC | |
| Acc65 I | GGTACC | |
| Acc I | GTMKAC | |
| Aci I | CCGC | |
| Acl I | AACGTT | |
| Afe I | AGCGCT | |
| Afl II | CTTAAG | |
| Afl III | ACRYGT | |
| Age I | ACCGGT | |
| Ahd I | GACNNNNNGTC | 1 |
| Alu I | AGCT | |
| Alw I | GGATC | |
| AlwN I | CAGNNNCTG | |
| Apa I | GGGCCC | |
| ApaL I | GTGCAC | |
| Apo I | RAATTY | |
| Asc I | GGCGCGCC | |
| Ase I | ATTAAT | |
| Ava I | CYCGRG | |
| Ava II | GGWCC | |
| Avr II | CCTAGG | |
| Bae I | NACNNNNGTAPyCN | 2 |
| BamH I | GGATCC | |
| Ban I | GGYRCC | |
| Ban II | GRGCYC | |
| Bbs I | GAAGAC | |
| Bbv I | GCAGC | |
| BbvC I | CCTCAGC | |
| Bcg I | CGANNNNNNTGC | 3 |
| BciV I | GTATCC | |
| Bcl I | TGATCA | |
| Bfa I | CTAG | |
| Bgl I | GCCNNNNNGGC | 4 |
| Bgl II | AGATCT | |

TABLE 1-continued

Recognition Sequences for Restriction Endonucleases.

| ENZYME | RECOGNITION SEQUENCE | SEQ ID NO. |
|---|---|---|
| Blp I | GCTNAGC | |
| Bmr I | ACTGGG | |
| Bpm I | CTGGAG | |
| BsaA I | YACGTR | |
| BsaB I | GATNNNNATC | 5 |
| BsaH I | GRCGYC | |
| Bsa I | GGTCTC | |
| BsaJ I | CCNNGG | |
| BsaW I | WCCGGW | |
| BseR I | GAGGAG | |
| Bsg I | GTGCAG | |
| BsiE I | CGRYCG | |
| BsiHKA I | GWGCWC | |
| BsiW I | CGTACG | |
| Bsl I | CCNNNNNNNGG | 6 |
| BsmA I | GTCTC | |
| BsmB I | CGTCTC | |
| BsmF I | GGGAC | |
| Bsm I | GAATGC | |
| BsoB I | CYCGRG | |
| Bsp1286 I | GDGCHC | |
| BspD I | ATCGAT | |
| BspE I | TCCGGA | |
| BspH I | TCATGA | |
| BspM I | ACCTGC | |
| BsrB I | CCGCTC | |
| BsrD I | GCAATG | |
| BsrF I | RCCGGY | |
| BsrG I | TGTACA | |
| Bsr I | ACTGG | |
| BssH II | GCGCGC | |
| BssK I | CCNGG | |
| Bst4C I | ACNGT | |
| BssS I | CACGAG | |
| BstAP I | GCANNNNNTGC | 7 |
| BstB I | TTCGAA | |
| BstE II | GGTNACC | |

TABLE 1-continued

Recognition Sequences for Restriction Endonucleases.

| ENZYME | RECOGNITION SEQUENCE | SEQ ID NO. |
|---|---|---|
| BstF5 I | GGATGNN | |
| BstN I | CCWGG | |
| BstU I | CGCG | |
| BstX I | CCANNNNNNTGG | 8 |
| BstY I | RGATCY | |
| BstZ17 I | GTATAC | |
| Bsu36 I | CCTNAGG | |
| Btg I | CCPuPyGG | |
| Btr I | CACGTG | |
| Cac8 I | GCNNGC | |
| Cla I | ATCGAT | |
| Dde I | CTNAG | |
| Dpn I | GATC | |
| Dpn II | GATC | |
| Dra I | TTTAAA | |
| Dra III | CACNNNGTG | |
| Drd I | GACNNNNNNGTC | 9 |
| Eae I | YGGCCR | |
| Eag I | CGGCCG | |
| Ear I | CTCTTC | |
| Eci I | GGCGGA | |
| EcoN I | CCTNNNNNAGG | 10 |
| EcoO109 I | RGGNCCY | |
| EcoR I | GAATTC | |
| EcoR V | GATATC | |
| Fau I | CCCGCNNNN | |
| Fnu4H I | GCNGC | |
| Fok I | GGATG | |
| Fse I | GGCCGGCC | |
| Fsp I | TGCGCA | |
| Hae II | RGCGCY | |
| Hae III | GGCC | |
| Hga I | GACGC | |
| Hha I | GCGC | |
| Hinc II | GTYRAC | |
| Hind III | AAGCTT | |
| Hinf I | GANTC | |

TABLE 1-continued

Recognition Sequences for Restriction Endonucleases.

| ENZYME | RECOGNITION SEQUENCE | SEQ ID NO. |
|---|---|---|
| HinP1 I | GCGC | |
| Hpa I | GTTAAC | |
| Hpa II | CCGG | |
| Hph I | GGTGA | |
| Kas I | GGCGCC | |
| Kpn I | GGTACC | |
| Mbo I | GATC | |
| Mbo II | GAAGA | |
| Mfe I | CAATTG | |
| Mlu I | ACGCGT | |
| Mly I | GAGTCNNNNN | 11 |
| Mnl I | CCTC | |
| Msc I | TGGCCA | |
| Mse I | TTAA | |
| Msl I | CAYNNNNRTG | 12 |
| MspAl I | CMGCKG | |
| Msp I | CCGG | |
| Mwo I | GCNNNNNNNGC | 13 |
| Nae I | GCCGGC | |
| Nar I | GGCGCC | |
| Nci I | CCSGG | |
| Nco I | CCATGG | |
| Nde I | CATATG | |
| NgoMI V | GCCGGC | |
| Nhe I | GCTAGC | |
| Nla III | CATG | |
| Nla IV | GGNNCC | |
| Not I | GCGGCCGC | |
| Nru I | TCGCGA | |
| Nsi I | ATGCAT | |
| Nsp I | RCATGY | |
| Pac I | TTAATTAA | |
| PaeR7 I | CTCGAG | |
| Pci I | ACATGT | |
| PflF I | GACNNNGTC | |
| PflM I | CCANNNNNTGG | 14 |
| PleI | GAGTC | |

TABLE 1-continued

Recognition Sequences for Restriction Endonucleases.

| ENZYME | RECOGNITION SEQUENCE | SEQ ID NO. |
| --- | --- | --- |
| Pme I | GTTTAAAC | |
| Pml I | CACGTG | |
| PpuM I | RGGWCCY | |
| PshA I | GACNNNNGTC | 15 |
| Psi I | TTATAA | |
| PspG I | CCWGG | |
| PspOM I | GGGCCC | |
| Pst I | CTGCAG | |
| Pvu I | CGATCG | |
| Pvu II | CAGCTG | |
| Rsa I | GTAC | |
| Rsr II | CGGWCCG | |
| Sac I | GAGCTC | |
| Sac II | CCGCGG | |
| Sal I | GTCGAC | |
| Sap I | GCTCTTC | |
| Sau3A I | GATC | |
| Sau96 I | GGNCC | |
| Sbf I | CCTGCAGG | |
| Sca I | AGTACT | |
| ScrF I | CCNGG | |
| SexA I | ACCWGGT | |
| SfaN I | GCATC | |
| Sfc I | CTRYAG | |
| Sfi I | GGCCNNNNNGGCC | 16 |
| Sfo I | GGCGCC | |
| SgrA I | CRCCGGYG | |
| Sma I | CCCGGG | |
| Sml I | CTYRAG | |
| SnaB I | TACGTA | |
| Spe I | ACTAGT | |
| Sph I | GCATGC | |
| Ssp I | AATATT | |
| Stu I | AGGCCT | |
| Sty I | CCWWGG | |
| Swa I | ATTTAAAT | |
| Taq I | TCGA | |
| Tfi I | GAWTC | |
| Tli I | CTCGAG | |
| Tse I | GCWGC | |
| Tsp45 I | GTSAC | |
| Tsp509 I | AATT | |
| TspR I | CAGTG | |
| Tth111 I | GACNNNGTC | |
| Xba I | TCTAGA | |
| Xcm I | CCANNNNNNNNNTGG | 17 |
| Xho I | CTCGAG | |
| Xma I | CCCGGG | |
| Xmn I | GAANNNNTTC | 18 |

Where
R = A or G, K = G or T, S = G or C, Y = C or T, M = A or C, W = A or T, B = not A (C, G or T), H = not G (A, C or T), D = not C (A, G or T), V = not T (A, C or G), and N = any nucleotide.

Those of ordinary skill in the art will be able to select an appropriate nuclease depending on the characteristics of the target genomic sequence and donor DNA. In one embodiment, the nuclease is a site-specific nuclease. In a related embodiment, the nuclease has a recognition sequence of at least 8, at least 10, at least 12, at least 14, at least 16, at least 18, at least 20, or at least 25 base pairs.

In one embodiment, the site-specific nuclease is a Cas nuclease. In a related embodiment, the Cas nuclease is Cas9. In a further embodiment, the nuclease is cas9 and the composition further comprises a guide RNA. Another example of a sequence-specific nuclease system that can be used with the methods and compositions described herein includes the Cas9/CRISPR system (Wiedenheft, B. et al. Nature 482, 331-338 (2012); Jinek, M. et al. Science 337, 816-821 (2012); Mali, P. et al. Science 339, 823-826 (2013); Cong, L. et al. Science 339, 819-823 (2013)). The Cas9/CRISPR (Clustered Regularly interspaced Short Palindromic Repeats) system exploits RNA-guided DNA-binding and sequence-specific cleavage of target DNA. The guide RNA/Cas9 combination confers site specificity to the nuclease. A guide RNA (gRNA) contains about 20 nucleotides that are complementary to a target genomic DNA sequence upstream of a genomic PAM (protospacer adjacent motifs) site (NNG) and a constant RNA scaffold region. The Cas (CRISPR-associated)9 protein binds to the gRNA and the target DNA to which the gRNA binds and introduces a double-strand break in a defined location upstream of the PAM site. Cas9 harbors two independent nuclease domains homologous to HNH and RuvC endonucleases, and by mutating either of the two domains, the Cas9 protein can be converted to a nickase that introduces single-strand breaks (Cong, L. et al. Science 339, 819-823 (2013)). It is specifically contemplated that the inventive methods and compositions can be used with the single- or double-strand-inducing version of Cas9, as well as with other RNA-guided DNA nucleases, such as other bacterial Cas9-like systems. The sequence-specific nuclease of the methods and compositions described herein can be engineered, chimeric, or isolated from an organism. The sequence-specific nuclease can be introduced into the cell in form of an RNA encoding the sequence-specific nuclease, such as an mRNA.

In one embodiment, the DNA digesting agent is a site-specific nuclease such as a zinc finger nuclease. Zinc finger nucleases generally comprise a DNA binding domain (i.e., zinc finger) and a cutting domain (i.e., nuclease). Zinc finger binding domains may be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:41 1-416; Zhang et al. (2000) J. Biol. Chem. 275(43):33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453,242 may be used to design a zinc finger binding domain to target a preselected sequence.

Alternative methods, such as rational design using a nondegenerate recognition code table may also be used to design a zinc finger binding domain to target a specific sequence (Sera et al. (2002) Biochemistry 41:7074-7081). Publically available web-based tools for identifying potential target sites in DNA sequences and designing zinc finger binding domains may be found at http://www.zincfinger-tools.org and http://bindr.gdcb.iastate.edu/ZiFiT/, respectively (Mandell et al. (2006) Nuc. Acid Res. 34:W516-W523; Sander et al. (2007) Nuc. Acid Res. 35:W599-W605).

A zinc finger binding domain may be designed to recognize and bind a DNA sequence ranging from about 3 nucleotides to about 21 nucleotides in length, or preferably from about 9 to about 18 nucleotides in length. In general, the zinc finger binding domains comprise at least three zinc finger recognition regions (i.e., zinc fingers). In one embodiment, the zinc finger binding domain may comprise four zinc finger recognition regions. In another embodiment, the zinc finger binding domain may comprise five zinc finger recognition regions. In still another embodiment, the zinc finger binding domain may comprise six zinc finger recognition regions. A zinc finger binding domain may be designed to bind to any suitable target DNA sequence. See for example, U.S. Pat. Nos. 6,607,882; 6,534,261 and 6,453, 242, the disclosures of which are incorporated by reference herein in their entireties.

Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237, each of which is incorporated by reference herein in its entirety. In addition, enhancement of binding specificity for zinc finger binding domains has been described, for example, in WO 02/077227.

Zinc finger binding domains and methods for design and construction of fusion proteins (and polynucleotides encoding same) are known to those of skill in the art and are described in detail in U.S. Patent Application Publication Nos. 20050064474 and 20060188987, each incorporated by reference herein in its entirety. Zinc finger recognition regions and/or multi-fingered zinc finger proteins may be linked together using suitable linker sequences, including for example, linkers of five or more amino acids in length. See, U.S. Pat. Nos. 6,479,626; 6,903,185; and 7,153,949, the disclosures of which are incorporated by reference herein in their entireties, for non-limiting examples of linker sequences of six or more amino acids in length. The zinc finger binding domain described herein may include a combination of suitable linkers between the individual zinc fingers of the protein.

In some embodiments, the zinc finger nuclease may further comprise a nuclear localization signal or sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh et al. (1996) Current Biology 6:1025-1027.

A zinc finger nuclease also includes a cleavage domain. The cleavage domain portion of the zinc finger nuclease may be obtained from any endonuclease or exonuclease. Non-limiting examples of endonucleases from which a cleavage domain may be derived include, but are not limited to, restriction endonucleases and homing endonucleases. See, for example, 2002-2003 Catalog, New England Biolabs, Beverly, Mass.; and Belfort et al. (1997) Nucleic Acids Res. 25:3379-3388 or www.neb.com. Additional enzymes that cleave DNA are known (e.g., 51 Nuclease; mung bean nuclease; pancreatic DNase I; micrococcal nuclease; yeast HO endonuclease). See also Linn et al. (eds.) Nucleases, Cold Spring Harbor Laboratory Press, 1993. One or more of these enzymes (or functional fragments thereof) may be used as a source of cleavage domains.

A cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease may comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

When two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs may intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fokl catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982. Thus, a zinc finger nuclease may comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

In another embodiment, the targeting endonuclease may be a meganuclease. Meganucleases are endodeoxyribonucleases characterized by a large recognition site, i.e., the recognition site generally ranges from about 12 base pairs to about 40 base pairs. As a consequence of this requirement, the recognition site generally occurs only once in any given genome. Naturally-occurring meganucleases recognize 15-40 base-pair cleavage sites and are commonly grouped into four families: the LAGLIDADG family, the GIY-YIG family, the His-Cyst box family and the HNH family. Meganucleases can be targeted to specific chromosomal sequence by modifying their recognition sequence using techniques well known to those skilled in the art.

In a further embodiment, the targeting endonuclease may be a transcription activator-like effector (TALE) nuclease. TALEs are transcription factors from the plant pathogen *Xanthomonas* that can be readily engineered to bind new DNA targets. TALEs or truncated versions thereof may be linked to the catalytic domain of endonucleases such as Fokl to create targeting endonuclease called TALE nucleases or TALENs.

In still another embodiment, the targeting endonuclease may be a site-specific nuclease. In particular, the site-specific nuclease may be a "rare-cutter" endonuclease whose recognition sequence occurs rarely in a genome. Preferably, the recognition sequence of the site-specific nuclease occurs only once in a genome.

In yet another embodiment, the targeting endonuclease may be an artificial targeted DNA double strand break inducing agent (also called an artificial restriction DNA cutter). For example, the artificial targeted DNA double strand break inducing agent may comprise a metal/chelator complex that cleaves DNA and at least one oligonucleotide that is complementary to the targeted cleavage site. The artificial targeted DNA double strand break inducing agent, therefore, does not contain any protein, The metal of the metal/chelator complex may be cerium, cadmium, cobalt, chromium, copper, iron, magnesium, manganese, zinc, and the like. The chelator of the metal/chelator complex may be EDTA, EGTA, BAPTA, and so forth. In a preferred embodiment, the metal/chelator complex may be Ce(IV)/EGTA. In another preferred embodiment, the artificial targeted DNA double strand break inducing agent may comprise a complex of Ce(IV)/EGTA and two strands of pseudo-complementary peptide nucleic acids (PNAs) (Katada et al., Current Gene Therapy, 201 1, 1 1 (1):38-45).

In a further embodiment, the nuclease may be a homing nuclease. Homing endonucleases include 1-5'cel, 1-Ceul, 1-Pspl, Vl-Sce, 1-SceTV, I-Csml, 1-Panl, 1-Scell, 1-Ppol, 1-Scelll, 1-Crel, 1-Tevl, 1-Tev and I-7evIII. Their recognition sequences are known. See also U.S. Pat. No. 5,420,032; U.S. Pat. No. 6,833,252; Belfort e a/. (1997) Nucleic Acids Res. 25:3379-3388; Ou on et al. (1989) Gene 82: 115-118; Perler et al. (1994) Nucleic Acids Res. 22, 1 125-1 127; Jasin (1996) Trends Genet. 12:224-228; Gimble et al. (1996) J. Mol. Biol. 263: 163-180; Argast et al. (1998) J Mol. Biol. 280:345-353 and the New England Biolabs catalogue.

In certain embodiments, the nuclease comprises an engineered (non-naturally occurring) homing endonuclease (meganuclease). The recognition sequences of homing endonucieases and meganucleases such as 1-Scel, 1-Ceul, VI-Pspl, Vl-Sce, I-ScelN, 1-Csml, 1-Panl, 1-Scell, 1-Ppol, 1-Scelll, 1-Crel, 1-Tevl, 1-Tevll and I-7evIII are known. See also U.S. Pat. No. 5,420,032; U.S. Pat. No. 6,833,252; Belfort et al. (1997) Nucleic Acids Res. 25:3379-3388; Dujon of a/. (1989) Gene 82: 115-118; Perler et al. (1994) Nucleic Acids Res. 22, 1125-1127; Jasin (1996) Trends Genet. 12:224-228; Gimble et al. (1996) J. Mol. Biol. 263: 163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In one embodiment, the DNA digesting agent is a site-specific nuclease of the group or selected from the group consisting of omega, zinc finger, TALE, and CRISPR/Cas9.

D. Markers

In certain embodiments of the invention, cells containing a genomic DNA sequence modification or cells that have been transfected with a composition of the present invention may be identified in vitro or in vivo by including a marker in the composition. The marker may be on the same plasmid or linearized DNA as the donor DNA or the marker may be on a separate piece of DNA. Such markers would confer an identifiable change to the cell permitting easy identification of cells that have been transfected with the composition. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker or an antibiotic resistance gene/marker.

Usually the inclusion of a drug selection marker aids in the cloning and identification of transformants, for example, genes that confer resistance to neomycin, puromycin, hygromycin, DHFR, GPT, zeocin, G418, phleomycin, blasticidin, and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. Further examples of selectable and screenable markers are well known to one of skill in the art. In certain embodiments, the marker is a fluorescent marker, an enzymatic marker, a luminescent marker, a photoactivatable marker, a photoconvertible marker, or a colorimetric marker. Flourescent markers include, for example, GFP and variants such as YFP, RFP etc., and other fluorescent proteins such as DsRed, mPlum, mCherry, YPet, Emerald, CyPet, T-Sapphire, and Venus. Photoactivatable markers include, for example, KFP, PA-mRFP, and Dronpa. Photoconvertible markers include, for example, mEosFP, KikGR, and PS-CFP2. Luminescent proteins include, for example, Neptune, FP595, and phialidin. Non-limiting examples of screening markers include The marker used in the invention may be encoded on an RNA or DNA. In a specific embodiment, the marker is encoded on plasmid DNA. In some embodiments, the marker and donor DNA are on the same plasmid.

In certain aspects, after electroporation cells that have internalized the electroporated compositions are selected for by negative selection. In other aspects, after electroporation cells that have internalized the electroporated constructs are selected for by positive selection. In some aspects selection involves exposing the cells to concentrations of a selection agent that would compromise the viability of a cell that did not express a selection resistance gene or take up a selection resistance gene during electroporation. In some aspects selection involves exposing the cells to a conditionally lethal concentration of the selection agent. In certain aspects the selection agent or compound is an antibiotic. In other aspects the selection agent is G418 (also known as geneticin and G418 sulfate), puromycin, zeocin, hygromycin, phleomycin or blasticidin, either alone or in combination. In certain aspects the concentration of selection agent is in the range of 0.1 µg/L to 0.5 µg/L, 0.5 µg/L to 1 µg/L, 1 µg/L to 2 µg/L, 2 µg/L to 5 µg/L, 5 µg/L to 10 µg/L, 10 µg/L to 100 µg/L, 100 µg/L to 500 µg/L, 0.1 mg/L to 0.5 mg/L, 0.5 mg/L to 1 mg/L, 1 mg/L to 2 mg/L, 2 mg/L to 5 mg/L, 5 mg/L to 10 mg/L, 10 mg/L to 100 mg/L, 100 mg/L to 500 mg/L, 0.1 g/L to 0.5 g/L, 0.5 g/L to 1 g/L, 1 g/L to 2 g/L, 2 g/L to 5 g/L, 5 g/L to 10 g/L, 10 g/L to 100 g/L, or 100 g/L to 500 g/L or any range derivable therein. In certain aspects the concentration of selection agent is (y)g/L, where 'y' can be any value including but not limited to 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100 or any range derivable therein. In some embodiments the selection agent is present in the culture media at a conditionally lethal concentration of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 g/L or any range derivable therein.

In certain embodiments, the nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably.

E. Vectors

Polypeptides such as the donor DNA, for example, may be encoded by a nucleic acid molecule in the composition. In certain embodiments, the nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody.

The term "expression vector" refers to a vector containing a nucleic acid sequence coding for at least part of a gene product capable of being transcribed or stably integrate into a host cell's genome and subsequently be transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein. It is contemplated that expression vectors that express a marker may be useful in the invention. In other embodiments, the marker is encoded on an mRNA and not in an expression vector.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

The particular promoter that is employed to control the expression of a peptide or protein encoding polynucleotide is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In certain specific embodiments, the composition transfected into the cell by electroporation is non-viral (i.e. does not contain any viral components). It is contemplated that non-viral methods will reduce toxicity and/or improve the safety of the method. It is contemplated that the combination of the use of small single-stranded DNA oligos and DNA digesting agents provided as RNA provide an advantage of decreased cytotoxicity and increased efficiency of genomic DNA sequence modification.

F. Nucleic Acid Sequence Modifications

In the context of this disclosure, the term "unmodified donor DNA" refers generally to an oligomer or polymer of ribonucleic acid (RNA) or deoxyribonucleic acid (DNA). In some embodiments a nucleic acid molecule comprises unmodified DNA. This term includes DNA composed of naturally occurring nucleobases, sugars and covalent internucleoside linkages. The term "DNA analog" refers to DNA that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases. The term "oligonucleotide" can be used to refer to unmodified oligonucleotides or oligonucleotide analogs.

Specific examples of nucleic acid molecules include nucleic acid molecules containing modified, i.e., non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases. In a specific embodiment, the modification comprises a methyl group.

Nucleic acid molecules can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Modifications to nucleic acid molecules can include modifications wherein one or both terminal nucleotides is modified.

One suitable phosphorus-containing modified internucleoside linkage is the phosphorothioate internucleoside linkage. A number of other modified oligonucleotide backbones (internucleoside linkages) are known in the art and may be useful in the context of this embodiment.

Representative U.S. patents that teach the preparation of phosphorus-containing internucleoside linkages include, but are not limited to, U.S. Pat. Nos. 3,687,808; 4,469,863; 4,476,301; 5,023,243, 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 5,625,050, 5,489,677, and 5,602,240 each of which is herein incorporated by reference.

Modified DNA backbones (internucleoside linkages) that do not include a phosphorus atom therein have internucleoside linkages that are formed by short chain alkyl or cycloalkyl internucleoside linkages, mixed heteroatom and alkyl or cycloalkyl internucleoside linkages, or one or more short chain heteroatomic or heterocyclic internucleoside linkages.

These include those having amide backbones; and others, including those having mixed N, O, S and CH2 component parts.

Representative U.S. patents that teach the preparation of the above non-phosphorous-containing oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

DNA compounds can also include mimetics. The term mimetic as it is applied to DNA is intended to include DNA compounds wherein only the furanose ring or both the furanose ring and the internucleotide linkage are replaced with novel groups, replacement of only the furanose ring with for example a morpholino ring, is also referred to in the art as being a sugar surrogate. The heterocyclic base moiety or a modified heterocyclic base moiety is maintained for hybridization with an appropriate target nucleic acid.

DNA mimetics can include compounds such as peptide nucleic acids (PNA) and cyclohexenyl nucleic acids (known as CeNA, see Wang et al., J. Am. Chem. Soc., 2000, 122, 8595-8602). Representative U.S. patents that teach the preparation of oligonucleotide mimetics include, but are not limited to, U.S. Pat. Nos. 5,539,082; 5,714,331; and 5,719,262, each of which is herein incorporated by reference. Another class of mimetic is referred to as phosphonomonoester nucleic acid and incorporates a phosphorus group in the backbone. This class of mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Another mimetic has been reported wherein the furanosyl ring has been replaced by a cyclobutyl moiety.

Nucleic acid molecules can also contain one or more modified or substituted sugar moieties. The base moieties are maintained for hybridization with an appropriate nucleic acid target compound. Sugar modifications can impart nuclease stability, binding affinity or some other beneficial biological property to the oligomeric compounds.

Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. A large number of sugar modifications are known in the art, sugars modified at the 2' position and those which have a bridge between any 2 atoms of the sugar (such that the sugar is bicyclic) are particularly useful in this embodiment. Examples of sugar modifications useful in this embodiment include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted C1 to C10 alkyl or C2 to C10 alkenyl and alkynyl. Particularly suitable are: 2-methoxyethoxy (also known as 2'-O-methoxyethyl, 2'-MOE, or 2'-OCH2CH2OCH3), 2'-O-methyl (2'-O—CH3), 2'-fluoro (2'-F), or bicyclic sugar modified nucleosides having a bridging group connecting the 4' carbon atom to the 2' carbon atom wherein example bridge groups include —CH2-O—, —(CH2)2-O— or —CH2-N(R3)-O wherein R3 is H or C1-C12 alkyl.

One modification that imparts increased nuclease resistance and a very high binding affinity to nucleotides is the 2'-MOE side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

2'-Sugar substituent groups may be in the arabino (up) position or ribo (down) position. One 2'-arabino modification is 2'-F. Similar modifications can also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative sugar substituents groups are disclosed in U.S. Pat. No. 6,172,209 entitled "Capped 2'-Oxyethoxy Oligonucleotides," hereby incorporated by reference in its entirety.

Representative cyclic sugar substituent groups are disclosed in U.S. Pat. No. 6,271,358 entitled "RNA Targeted 2'-Oligomeric compounds that are Conformationally Preorganized," hereby incorporated by reference in its entirety.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Nucleic acid molecules can also contain one or more nucleobase (often referred to in the art simply as "base") modifications or substitutions which are structurally distinguishable from, yet functionally interchangeable with, naturally occurring or synthetic unmodified nucleobases. Such nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds. These include 5-substituted pyrimidines, 6-azapyrimidines and N-2, N-6 and O-6 substituted purines, including 2 aminopropyladenine, 5-propynyluracil and 5-propynylcytosine.

Additional modifications to nucleic acid molecules are disclosed in U.S. Patent Publication 2009/0221685, which is hereby incorporated by reference. Also disclosed herein are additional suitable conjugates to the nucleic acid molecules.

II. CELL CULTURE

A. Host Cells

As used herein, the terms "cell," "cell line," and "cell culture" may be used interchangeably. All of these terms also include both freshly isolated cells and ex vivo cultured, activated or expanded cells. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

In certain embodiments transfection can be carried out on any prokaryotic or eukaryotic cell. In some aspects electroporation involves transfection of a human cell. In other aspects electroporation involves transfection of an animal cell. In certain aspects transfection involves transfection of a cell line or a hybrid cell type. In some aspects the cell or cells being transfected are cancer cells, tumor cells or immortalized cells. In some instances tumor, cancer, immortalized cells or cell lines are induced and in other instances tumor, cancer, immortalized cells or cell lines enter their respective state or condition naturally. In certain aspects the cells or cell lines can be A549, B-cells, B16, BHK-21, C2C12, C6, CaCo-2, CAP/, CAP-T, CHO, CHO2, CHO-DG44, CHO-K1, COS-1, Cos-7, CV-1, Dendritic cells, DLD-1, Embryonic Stem (ES) Cell or derivative, H1299, HEK, 293, 293T, 293FT, Hep G2, Hematopoietic Stem Cells, HOS, Huh-7, Induced Pluripotent Stem (iPS) Cell or derivative, Jurkat, K562, L5278Y, LNCaP, MCF7, MDA-MB-231, MDCK, Mesenchymal Cells, Min-6, Monocytic cell, Neuro2a, NIH 3T3, NIH3T3L1, K562, NK-cells, NSO, Panc-1, PC12, PC-3, Peripheral blood cells, Plasma cells, Primary Fibroblasts, RBL, Renca, RLE, SF21, SF9, SH-SY5Y, SK-MES-1, SK-N-SH, SL3, SW403, Stimulus-triggered Acquisition of Pluripotency (STAP) cell or derivate SW403, T-cells, THP-1, Tumor cells, U2OS, U937, peripheral blood lymphocytes, expanded T cells, hematopoietic stem cells, or Vero cells. In specific embodiments, the cells are peripheral blood lymphocytes, expanded T cells, natural killer cells (NK cells), stem cells, hematopoietic stem cells, or primary cells. In a specific embodiment, the cells are hematopoietic stem cells. In a further specific embodiment, the cells are peripheral blood lymphocytes.

In certain embodiments, the cell is one that is known in the art to be difficult to transfect. Such cells are known in the art and include, for example, primary cells, insect cells, SF9 cells, Jurkat cells, CHO cells, stem cells, slowly dividing cells, T cells, and non-dividing cells. In some embodiments, the cells are T cells. In some embodiments, the cells are primary cells. In some embodiments, the cells are stem cells. In some embodiments the cells are hematopoietic stem cells including myeloid and lymphoid progenitor cells. In some embodiments, the cells are mesenchymal stem cells. In some embodiments, the cell is a germ cell such as an egg cell or sperm cell. In some embodiments, the cell is a fertilized embryo. In some embodiments, the cell is a human fertilized embryo.

In some embodiments, cells may subjected to limiting dilution methods to enable the expansion of clonal populations of cells. The methods of limiting dilution cloning are well known to those of skill in the art. Such methods have been described, for example for hybridomas but can be applied to any cell. Such methods are described in (Cloning hybridoma cells by limiting dilution, Journal of tissue culture methods, 1985, Volume 9, Issue 3, pp 175-177, by Joan C. Rener, Bruce L. Brown, and Roland M. Nardone) which is incorporated by reference herein.

In some embodiments cells are cultured before transfection or after transrection. In other embodiments, cells are cultured during the selection phase after transfection. In yet other embodiments, cells are cultured during the maintenance and clonal selection and initial expansion phase. In still other embodiments, cells are cultured during the screening phase. In other embodiments, cells are cultured during the large scale production phase. Methods of culturing suspension and adherent cells are well-known to those skilled in the art. In some embodiments, cells are cultured in suspension, using commercially available cell-culture vessels and cell culture media. Examples of commercially available culturing vessels that may be used in some embodiments including ADME/TOX Plates, Cell Chamber Slides and Coverslips, Cell Counting Equipment, Cell Culture Surfaces, Corning HYPERFlask Cell Culture Vessels, Coated Cultureware, Nalgene Cryoware, Culture Chamber, Culture Dishes, Glass Culture Flasks, Plastic Culture Flasks, 3D Culture Formats, Culture Multiwell Plates, Culture Plate Inserts, Glass Culture Tubes, Plastic Culture Tubes, Stackable Cell Culture Vessels, Hypoxic Culture Chamber, Petri dish and flask carriers, Quickfit culture vessels, Scale-Up Cell Culture using Roller Bottles, Spinner Flasks, 3D Cell Culture, or cell culture bags.

In other embodiments, media may be formulated using components well-known to those skilled in the art. Formulations and methods of culturing cells are described in detail in the following references: Short Protocols in Cell Biology J. Bonifacino, et al., ed., John Wiley & Sons, 2003, 826 pp; Live Cell Imaging: A Laboratory Manual D. Spector & R. Goldman, ed., Cold Spring Harbor Laboratory Press, 2004, 450 pp.; Stem Cells Handbook S. Sell, ed., Humana Press, 2003, 528 pp.; Animal Cell Culture: Essential Methods, John M. Davis, John Wiley & Sons, Mar. 16, 2011; Basic Cell Culture Protocols, Cheryl D. Helgason, Cindy Miller, Humana Press, 2005; Human Cell Culture Protocols, Series: Methods in Molecular Biology, Vol. 806, Mitry, Ragai R.; Hughes, Robin D. (Eds.), 3rd ed. 2012, XIV, 435 p. 89, Humana Press; Cancer Cell Culture: Method and Protocols, Cheryl D. Helgason, Cindy Miller, Humana Press, 2005; Human Cell Culture Protocols, Series: Methods in Molecular Biology, Vol. 806, Mitry, Ragai R.; Hughes, Robin D. (Eds.), 3rd ed. 2012, XIV, 435 p. 89, Humana Press; Cancer Cell Culture: Method and Protocols, Simon P. Langdon, Springer, 2004; Molecular Cell Biology. 4th edition., Lodish H, Berk A, Zipursky S L, et al., New York: W. H. Freeman; 2000, Section 6.2Growth of Animal Cells in Culture, all of which are incorporated herein by reference.

In some embodiments, during the screening and expansion phase and/or during the large scale production phase (also referred to as fed-batch & comparison), expanded electroporated cells that result from selection or screening may comprise modified genomic DNA sequence.

B. Activating Composition

Methods described herein relate to contacting the cells with an activating composition prior to transfection of the cells. Cells may be activated according to methods known in the art and/or described herein. For example, T cells may be activated according to the following:

| | T cell subsets | | | | | |
|---|---|---|---|---|---|---|
| | Th1 | Th1/Th2 | Th1 | Th17 | Treg | Th2/Th9 |
| Activated by | Anti-CD3/CD28; PMA; pervanadate | Anti-CD3/CD28; PMA; pervandadate | IFN-α | IL6; IL-21 | IL-2; IL-7; IL-15 | IL-4 |

Kits for activation of T cells are also commercially available. Example kits include anti-Biotin Particles (e.g. MACSiBead or DYNABEADS®)) and biotinylated antibodies against human CD2, CD3, and CD28. Anti-Biotin Particles loaded with the biotinylated antibodies are used to mimic antigen-presenting cells and activate resting T cells from PBMCs as well as purified T cells. T cell expansion is achieved by culturing and reactivation at day 14 of culture.

T cells may also be activated by mitogens such as ConA, PHA, and PWM, for example.

III. THERAPEUTIC AND DRUG DISCOVERY APPLICATIONS

In certain embodiments, the cells and cell lines produced by methods described herein are ones that, upon modification of the genomic DNA, provide a therapeutic effect. Primary cells may be isolated, modified by methods described herein, and used ex vivo for reintroduction into the subject to be treated. Suitable primary cells include peripheral blood mononuclear cells (PBMC), peripheral blood lmyphocytes (PBLs) and other blood cell subsets such as, but not limited to, CD4+ T cells or CD8+ T cells. Other suitable primary cells include progenitor cells such as myeloid or lymphoid progenitor cells. Suitable cells also include stem cells such as, by way of example, embryonic stem cells, induced pluripotent stem cells, hematopoietic stem cells, neuronal stem cells, mesenchymal stem cells, muscle stem cells and skin stem cells. For example, iPSCs can be derived ex vivo from a patient afflicted with a known genetic mutation associated, and this mutation can be modified to a wild-type allele using methods described herein. The modified iPSC can then be differentiated into dopaminergic neurons and reimplanted into the patient. In another ex vivo therapeutic application, hematopoietic stem cells can be isolated from a patient afflicted with a known genetic mutation, which can then be modified to correct the genetic mutation. The HSCs can then be administered back to the patient for a therapeutic effect or can be differentiated in culture into a more mature hematopoietic cell prior to administration to the patient.

In some embodiments, the modified genomic DNA sequence and/or the donor DNA comprises a disease-associated gene. In some embodiments, the sequence modification region comprises a disease-associated gene. Disease-associated genes are known in the art. It is contemplated that a disease associated gene is one that is disclosed on the world wide web at genecards.org/cgi-bin/listdiseasecards.pl?type=full&no_limit=1. The complete list of genes, as well as their associated disease is herein incorporated by reference in its entirety.

In one embodiment, the method comprises modifying genomic DNA in hematopoietic stem cells (a.k.a. hemocytoblasts) or in myeloid progenitor cells.

Another example in which the disclosed method may be used therapeutically is the site-specific integration of chimeric antigen receptor (CAR). The term "chimeric antigen receptor" or "CAR" refers to engineered receptors, which graft an arbitrary specificity onto an immune effector cell. These receptors are used to graft the specificity of a monoclonal antibody onto a T cell. The receptors are called chimeric because they are composed of parts from different sources. The most common form of these molecules are fusions of single-chain variable fragments (scFv) derived from monoclonal antibodies, fused to CD3-zeta transmembrane and endodomain; CD28 or 41BB intracellular domains, or combinations thereof. Such molecules result in the transmission of a signal in response to recognition by the scFv of its target. An example of such a construct is 14g2a-Zeta, which is a fusion of a scFv derived from hybridoma 14g2a (which recognizes disialoganglioside GD2). When T cells express this molecule, they recognize and kill target cells that express GD2 (e.g. neuroblastoma cells). To target malignant B cells, investigators have redirected the specificity of T cells using a chimeric immunoreceptor specific for the B-lineage molecule, CD19. The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows the scFv to orient in different directions to enable antigen binding. The transmembrane domain is a typical hydrophobic alpha helix usually derived from the original molecule of the signalling endodomain which protrudes into the cell and transmits the desired signal. CARs are proteins that allow the T cells to recognize a specific protein (antigen) on tumor cells. CARs are engineered receptors, which graft an arbitrary specificity onto an immune effector cell. Typically, these receptors are used to graft the specificity of a monoclonal antibody onto a T cell.

Artificial T cell receptors are under investigation as a therapy for cancer, using a technique called adoptive cell transfer. T cells are removed from a patient and modified so that they express receptors specific to the particular form of cancer. The T cells, which can then recognize and kill the cancer cells, are reintroduced into the patient. Modification of T-cells sourced from donors other than the patient are also under investigation.

Figure 16A:
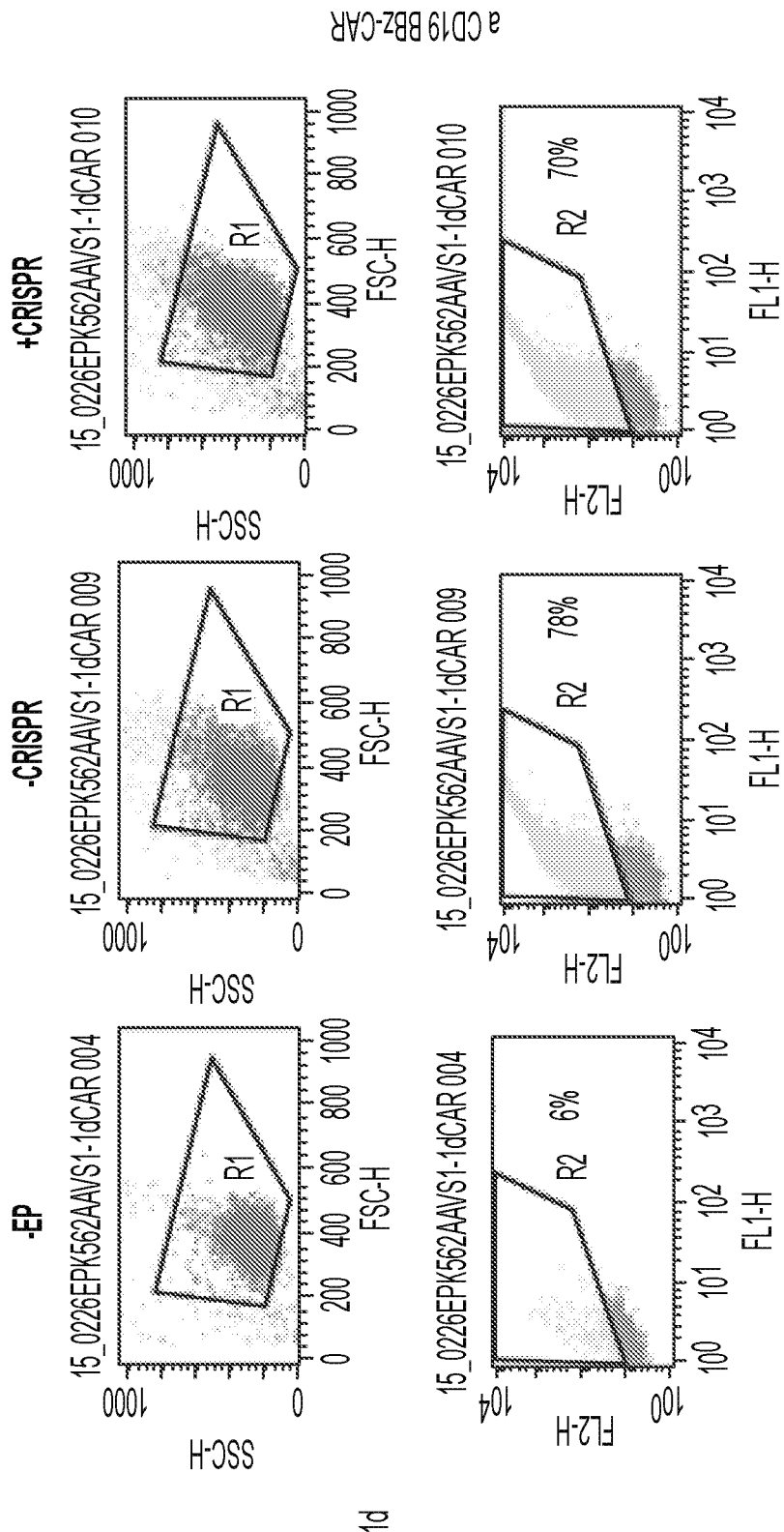
FIGS. 16A-16B: Targeted Integration of PGK-CAR-aCD19BBz-PolyA in AAVS1 Site of K562 by mRNA-CRISPR and Donor Plasmid DNA (Without Selection). Shown is FACS analysis K562 cells transfected with PGK-CAR-aCD19BBz-PolyA and with (+CRISPR) or without (−CRISPR) mRNA-CRISPR system that targets the transgene to the AAVS1 site. FACS analysis was done on cells at one and eight days post transfection. As shown in this figure, only cells transfected with the donor plasmid DNA and the CRISPR system showed a significant amount of GFP expression (44%) at eight days post transfection.
Figure 16B:
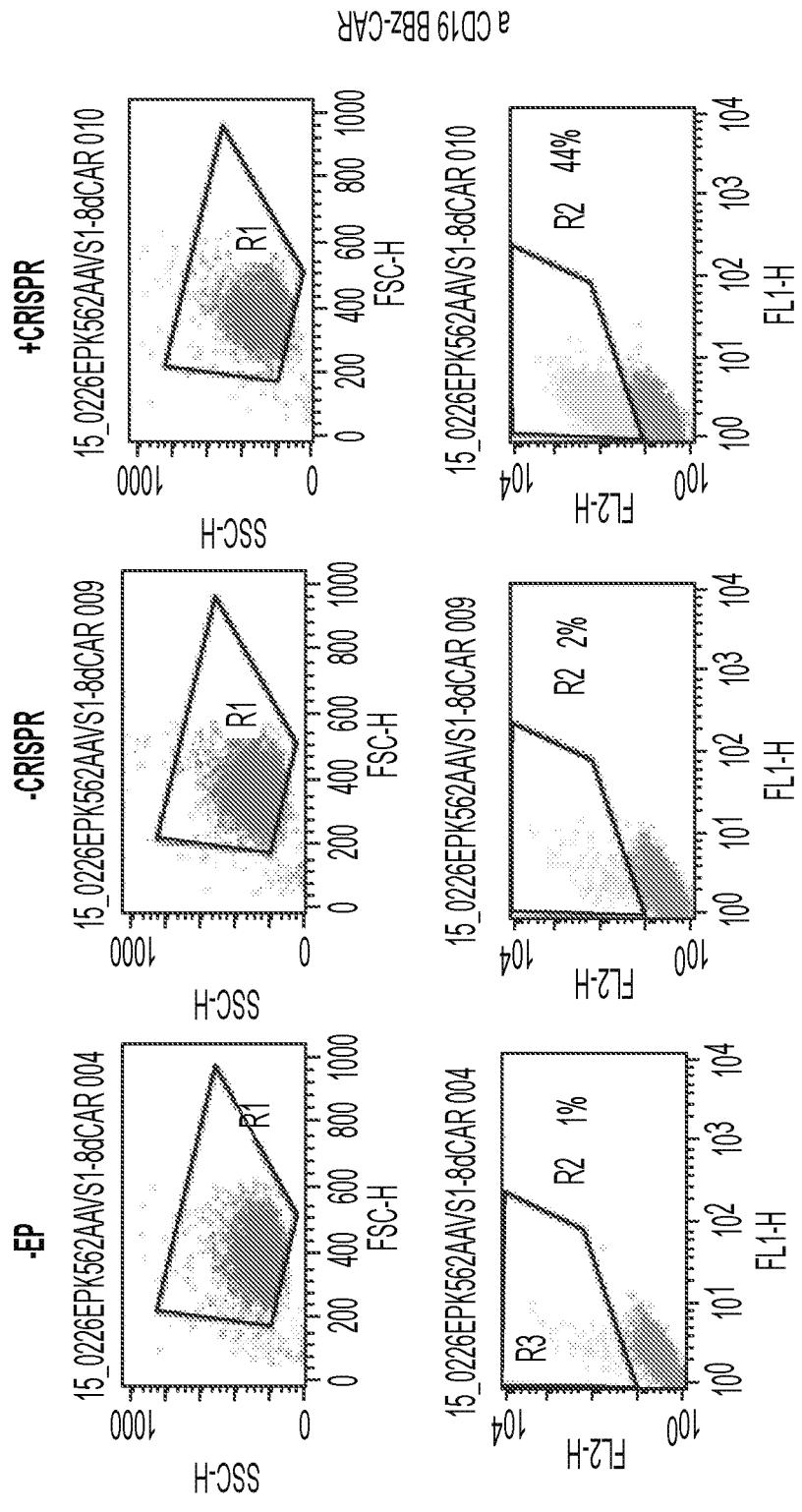

These engineered CAR T cells may be expanded in vitro, and the expanded population of CAR T cells can then infused into the patient. After the infusion, the T cells multiply in the patient's body and, with guidance from their engineered receptor, recognize and kill cancer cells that harbor the antigen on their surfaces. Current therapeutic methods involve the introduction of CAR by viral infection. However, there are always safety concerns when using viral infection in therapeutic methods. Therefore, the methods described herein are non-viral approaches to gene therapy and genome engineering. Previously, it was not possible to transfect immunological cells with plasmid DNA, since doing so led to toxicity of the cells. Applicant's found that an activation step prior to cell transfection overcame the viability issue and allowed for long pieces of DNA (and/or high concentrations) to be transfected into cells while maintaining a high level of viability. Using methods described herein, the CAR can be integrated into a specific site of immunological cells. In some embodiments, the cells are autologous immune cells. The long-term expression of the CAR in T or natural killer (NK) cells can be used for leukemia treatment or treatment of tumors associated with certain antigens. A non-selection or selection may be used on cells with the site-specific integration of the CAR. For the selection approach, a selectable marker may be integrated at the same site and be on the same plasmid as the CAR or the selectable marker may integrate at another site-specific location. For the non-selection approach, it is contemplated that the presence of antigen (tumor) will serve as a natural selection pressure, so that the CAR-positive cell population will be further stimulated and expanded in vivo, whereas the CAR-negative cells will be depleted naturally, since no activation exists. The T or NK cells for therapeutic purposes can be obtained through apheresis with or without purification. The cells may then be activated, transfected, and injected back into the patient as described in the methods of the disclosure. As shown in FIG. 16, data described herein demonstrate the successful site-specific integration of the CAR into K562 cells.

A further example of how the disclosed methods may be used therapeutically is in expression of the CFTR (cystic fibrosis transmembrane conductance regulator) transgene in epithelial cells of a patient that has cystic fibrosis due to loss of CFTR function. Gene therapy has been explored as a potential cure for cystic fibrosis. Ideally, gene therapy places a normal copy of the CFTR gene into affected cells. Transferring the normal CFTR gene into the affected epithelium cells would result in the production of functional CFTR in all target cells, without adverse reactions or an inflammation response. Studies have shown that to prevent the lung manifestations of cystic fibrosis, only 5-10% the normal amount of CFTR gene expression is needed. Multiple approaches have been tested for gene transfer, such as liposomes and viral vectors in animal models and clinical trials. However, both methods were found to be relatively inefficient treatment options. The main reason is that very few cells take up the vector and express the gene, so the treatment has little effect. It is contemplated that functional CTFR transgene can be site-specifically integrated into epithelial cells or intestinal stem cell organoids which have been activated prior to transfection of the donor DNA. The cells can then be transplanted into the airway of the patient, where they will fulfill the normal function of the CTFR gene.

In a further example, the methods described herein can be used to treat patients with hemophilia. Patients with Hemophilia are not able to induce blood clots and suffer from external and internal bleeding that can be life threatening. Site-specific targeted genomic integration can be performed using Factor VIII or Factor IX transgene as the donor DNA. Primary liver, muscle or blood vessel cells or progenitor liver muscle or blood vessel cells may be isolated from the patient or a donor host. The cells can then be activated and, following activation of the cells, the cells may then be transplanted into the patient for transgene expression of the integrated Factor VIII or Factor IX.

In a further example, targeted transgene integration can be used for cell line development. Applicants have demonstrated in the Examples that expression of a transgene in a cell using the methods described herein results in almost 40% expression of the transgene, which is indicative of the high efficiency of this method. Therefore, this method may replace the traditional method of randomized integration and colony selection. The methods described herein may be used for cell line optimization for protein secretion by integrating transgene with an external promoter for expressing various cytokines or antibodies for therapeutic or preclinical use.

In certain aspects, the methods described herein relate to an improved method for ex vivo therapy. A population of cells may be isolated from a subject, the cells may then be activated by methods known in the art and/or described herein, and the genomic DNA of the cells may be modified in a manner that corrects a defect or site-specifically integrates a target gene. The population of cells may then be transplanted into a subject for therapeutic use. In certain instances, the population of cells isolated may comprise a subset of cells sensitive to certain in vitro manipulations such as traditional transfection and/or electroporation methods, for example, or the subset of cells may be resistant to traditional transfection and/or electroporation methods or genomic DNA manipulation. It is contemplated that modifying the genomic DNA with methods described herein will result in a greater efficiency of the sequence modification in such populations.

One aspect of the disclosure relates to a method for site-specific sequence modification of a target genomic DNA region in cells isolated from a subject comprising: isolating cells from a subject; activating the cells with an activation composition; transfecting the cells with a transfection composition comprising (a) donor DNA and (b) a DNA digesting agent; wherein the donor DNA comprises: (i) a homologous region comprising nucleic acid sequence homologous to the target genomic DNA region; and (ii) a sequence modification region; and wherein the genomic DNA sequence is modified specifically at the target genomic DNA region.

Additionally, cells and cell lines produced by the methods used herein may be useful for drug development and/or reverse genetic studies. Such cells and animals may reveal phenotypes associated with a particular mutation or with its sequence modification, and may be used to screen drugs that will interact either specifically with the mutation(s) or mutant proteins in question, or that are useful for treatment of the disease in an afflicted animal. These cell lines can also provide tools to investigate the effects of specific mutations since a cell line and its corresponding "modified" cell line represent "genetically identical" controls and thus provides a powerful tool for repair of disease-specific mutations, drug screening and discovery, and disease mechanism research. It is further contemplated that this technology can provide a scientifically superior alternative to current gene-knockdown techniques such as RNAi and shRNAs, for example. In one example, a the DNA sequence modification is a stop codon that is introduced into a gene of interest to study a developmental or disease mechanism or for a therapeutic application.

The compositions of the disclosure may be used for in vivo, in vitro, or ex vivo administration. For example, the compositions of the disclosure may be useful as cancer vaccines.

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present disclosure, the compositions may be administered either in vitro, ex vivo, or in vivo. In certain in vitro embodiments, autologous T cells are incubated with compositions of this disclosure. The cells can then be used for in vitro analysis, or alternatively for ex vivo administration.

Method aspects of the disclosure also relate to a methods for vaccinating a subject and/or for treating certain cancers by a method comprising: contacting cells with an activating composition; transfecting the cells with a transfection composition comprising (a) donor DNA and (b) a DNA digesting agent; wherein the donor DNA comprises: (i) a homologous region comprising nucleic acid sequence homologous to the target genomic DNA region; and (ii) a chimeric antigen receptor (CAR); and wherein the genomic DNA sequence is modified specifically at the target genomic DNA region to integrate the CAR; and administering the cells to the patient. In some embodiments, the immune cell is autologous. In some embodiments, the immune cell has been contacted with an antigen. In some embodiments, the antigen is an antigen expressed by the subject's cancer cells. In some embodiments, the antigen is cell free. The term "cell free" refers to a composition that does not have any cellular components. In some embodiments, the antigen is an extract from the patient's tumor. In some embodiments, the antigen is a polypeptide. In some embodiments, the antigen comprises one or more of tumor cell lysate, apoptotic tumor cell, tumor-associated antigen, and tumor-derived mRNA.

In some embodiments, the immune cell is an antigen presenting cells. Examples of the antigen-presenting cells include dendritic cells, macrophages, B cells, and tumor cells (false antigen-presenting cells) in which a T cell stimulation factor (e.g., B7 or 4-1 BBL) and the like is forcibly expressed by, for example, gene transfer. In some embodiments, the antigen presenting cell is a dendritic cell.

The route of administration of the immune cell may be, for example, intratumoral, intracutaneous, subcutaneous, intravenous, intralymphatic, and intraperitoneal administrations. In some embodiments, the administration is intratumoral or intralymphatic. In some embodiments, the immune cells are administered directly into a cancer tissue or a lymph node.

In some embodiments, the immune cell is a T cell. The T cells may be ones that have been contacted with an antigen or with antigen-presenting cells. For example, APCs may be cultured with tumor antigen specific to the patient's cancer to differentiate them, into, for example, CD8-positive cytotoxic T lymphocytes (CTLs) or CD4-positive helper T cells. The T cells thus established may be administered to an individual with cancer.

The origin of the naive T cells is not specifically limited and it may be derived from, for example, peripheral blood of a vertebrate animal. The naive T cell used may be CD8-positive cells or CD4-positive cells isolated from a PBMC fraction. In some embodiments, the naive T cells are CD8-positive cells or CD4-positive cells mixed with other cells and components without being isolated from the PBMC fraction in terms of the efficiency of inducing CTLs. For example, when cells of a PBMC fraction are cultured in a medium supplemented with serum and tumor antigen, the PBMCs differentiate into dendritic cell precursors. The dendritic cell precursors then bind to the peptide and differentiate into dendritic cells as the antigen-presenting cells presenting this peptide/tumor antigen. The antigen-presenting cells stimulate the CD8-positive T cells in the PBMCs to differentiate them into CTLs. Thus, the CTLs capable of recognizing the added peptide can be obtained. The CTLs thus obtained may be isolated and used as the cancer vaccine as they are. Alternatively, they may be cultured further in the presence of interleukin such as IL-2, the antigen-presenting cell, and tumor antigen before used as the cancer vaccine. The route of their administration is not specifically limited and examples include intracutaneous, subcutaneous, intravenous, and intratumoral administrations.

IV. TRANSFECTION

Transfection is the process of deliberately introducing nucleic acids into cells. In certain embodiments, the transfection is non-viral, which indicates that the sequences used in the plasmid background are non-viral, and the DNA does not enter the cell through viral mechanisms. Transfection of animal cells typically involves opening transient pores or "holes" in the cell membrane to allow the uptake of material. Transfection can be carried out using methods known in the art and described below.

Non-Chemical Methods of Transfection

2. Electroporation

Certain embodiments involve the use of electroporation to facilitate the entry of one or more nucleic acid molecules into host cells.

As used herein, "electroporation" or "electroloading" refers to application of an electrical current or electrical field to a cell to facilitate entry of a nucleic acid molecule into the cell. One of skill in the art would understand that any method and technique of electroporation is contemplated by the present invention.

In certain embodiments of the invention, electroloading may be carried out as described in U.S. Pat. No. 5,612,207 (specifically incorporated herein by reference), U.S. Pat. No. 5,720,921 (specifically incorporated herein by reference), U.S. Pat. No. 6,074,605 (specifically incorporated herein by reference); U.S. Pat. No. 6,090,617 (specifically incorporated herein by reference); U.S. Pat. No. 6,485,961 (specifically incorporated herein by reference); U.S. Pat. No. 7,029,916 (specifically incorporated herein by reference), U.S. Pat. No. 7,141,425 (specifically incorporated herein by reference), U.S. Pat. No. 7,186,559 (specifically incorporated herein by reference), U.S. Pat. No. 7,771,984 (specifically incorporated herein by reference), and U.S. publication number 2011/0065171 (specifically incorporated herein by reference).

Other methods and devices for electroloading that may be used in the context of the present invention are also described in, for example, published PCT Application Nos. WO 03/018751 and WO 2004/031353; U.S. patent application Ser. Nos. 10/781,440, 10/080,272, and 10/675,592; and U.S. Pat. Nos. 6,773,669, 6,090,617, 6,617,154, all of which are incorporated by reference.

In certain embodiments of the invention, electroporation may be carried out as described in U.S. patent application Ser. No. 10/225,446, filed Aug. 21, 2002, the entire disclosure of which is specifically incorporated herein by reference.

In further embodiments of the invention, flow electroporation is performed using MaxCyte STX®, MaxCyte VLX®, or MaxCyte GT® flow electroporation instrumentation. In specific embodiments, static or flow electroporation is used with parameters described throughout the disclosure.

The claimed methods of transfecting cells by electroporation, preferably flow electroporation, is capable of achieving transfection efficiencies of greater than 40%, greater than 50% and greater than 60%, 70%, 80% or 90% (or any range derivable therein). Transfection efficiency can be measured either by the percentage of the cells that express the product of the gene or the secretion level of the product express by the gene. The cells maintain a high viability during and after the electroporation process. Viability is routinely more than 50% or greater. Viability or electroporated cells can be at most or at least about 5%, 10%, 15%, 20%, 25%, 30%, 35%, 40%, 45%, 50%, 55%, 60%, 65%, 70%, 75%, 80%, 85%, 90% or 95% (or any range derivable therein). of the viability of the starting, unelectroporated population or an electroporated population transfected with a control construct.

In some embodiments the current methods use a flow electroporation apparatus for electrical stimulation of suspensions of particles, comprising a flow electroporation cell assembly having one or more inlet flow portals, one or more outlet flow portals, and one or more flow channels, the flow channels being comprised of two or more walls, with the flow channels further being configured to receive and transiently contain a continuous flow of particles in suspension from the inlet flow portals; and paired electrodes disposed in relation to the flow channels such that each electrode forms at least one wall of the flow channels, the electrodes further comprising placing the electrodes in electrical communication with a source of electrical energy, whereby suspensions of particles flowing through the channels may be subjected to an electrical field formed between the electrodes.

In some embodiments the current methods use flow electroporation to overcome the limitation of sample size. With this method, a cell suspension is passed across parallel bar electrodes that are contained in a flow cell that is preferably disposable.

In further embodiments, the flow or static electroporation methods described herein are employed to overcome thermal degradation of the sample. It is to be understood that different configurations of cells can be used in the current methods. During electroporation, the cells are subjected to electrical pulses with predetermined characteristics. For example, the specific settings for preparation of sample cells are: voltage, 750V; pulse width, 650 μsec; time between pulses, 100 μsec; 2 biphasic pulses in a burst; time between bursts, 12 sec; flow rate, 0.05 mL/sec. The molecule or molecules of interest can then diffuse into the cell following concentration and/or electrical gradients. The present invention is optionally capable of subjecting the cells to a range of electric field strengths.

Another advantage of the current flow electroporation methods is the speed at which a large population of cells can be transfected. For example, a population of lymphocytes can be transfected by electroporation by electroporating the sample in less than 5 hours, preferably less than 4 hours and most preferable in less than 3 hours and most preferably in less than 2 hours. The time of electroporation is the time that the sample is processed by the flow electroporation process. In certain embodiments, 1E10 cells are transfected in 30 minutes or less using flow electroporation. In further embodiments, 2E11 cells may be transfected in 30 minutes, or 60 minutes or less using flow electroporation.

For flow electroporation, the process is initiated by attaching the flow cell with solutions and cell suspensions in the containers with the necessary fluids and samples. Priming solution (saline) and cell suspension are introduced by providing the required commands to the electroporation system, which controls operation of the pump and pinch valves. As the cells transit the flow path between electrodes, electric pulses of the chosen voltage, duration, and frequency are applied. Product and waste fluids are collected in the designated containers.

The user inputs the desired voltage and other parameters into the flow electroporation system of the present invention. As noted above, a range of settings is optionally available. The computer communicates to the electronics in the tower to charge the capacitor bank to the desired voltage. Appropriate switches then manipulate the voltage before it is delivered to the flow path to create the electric field (the switches provide alternating pulses or bursts to minimize electrode wear brought on by prolonged exposure to the electric field). The voltage is delivered according to the duration and frequency parameters set into the flow electroporation system of the present invention by the operator. The flow electroporation system of the present invention is now described in detail.

The flow electroporation process can be initiated by, for example, placing an electroporation chamber in fluid communication with solutions and cell suspensions in containers (e.g., via tubing), which may be carried out in an aseptic or sterile environment. A cell suspension and/or other reagents may be introduced to the electroporation chamber using one or more pumps, vacuums, valves, other mechanical devices that change the air pressure or volume inside the electroporation chamber and combinations thereof, which can cause the cell suspension and/or other reagents to flow into the electroporation chamber at a desired time and at the desired rate. If a portion of the cell suspension and/or other reagents is positioned in the electroporation chamber, electric pulses of a desired voltage, duration, and/or interval are applied the cell suspension and/or other reagents. After electroporation, the processed cell suspension and/or other reagents can be removed from the electroporation chamber using one or more pumps, vacuums, valves, other electrical, mechanical, pneumatic, or microfluidic devices that change the displacement, pressure or volume inside the electroporation chamber, and combinations thereof. In certain embodiments, gravity or manual transfer may be used to move sample or processed sample into or out of an electroporation chamber. If desired, a new cell suspension and/or other reagents can be introduced into the electroporation chamber. An electroporated sample can be collected separately from a sample that has not yet been electroporated. The preceding series of events can be coordinated temporally by a computer coupled to, for example, electronic circuitry (e.g., that provides the electrical pulse), pumps, vacuums, valves, combinations thereof, and other components that effect and control the flow of a sample into and out of the electroporation chamber. As an example, the electroporation process can be implemented by a computer, including by an operator through a graphic user interface on a monitor and/or a keyboard. Examples of suitable valves include pinch valves, butterfly valves, and/or ball valves. Examples of suitable pumps include centrifugal or positive displacement pumps.

As an example, a flow electroporation device can comprise at least two electrodes separated by a spacer, where the spacer and the at least two electrodes define a chamber. In some embodiments, the electroporation chamber can further comprise a least three ports traversing the spacer, where a first port is for sample flow into the chamber, a second port is for processed sample flow out of the chamber, and a third port is for non-sample fluid flow into or out of the chamber. In some embodiments, the non-sample fluid flows out of the chamber when a sample flows into the chamber, and the non-sample fluid flows into the chamber when processed sample flows out of the chamber. As another example, a flow electroporation device can comprise an electroporation chamber having a top and bottom portion comprising at least two parallel electrodes, the chamber being formed between the two electrodes and having two chamber ports in the bottom portion of the electroporation chamber and two chamber ports in the top portion of the electroporation chamber. Such a device can further comprise at least one sample container in fluid communication with the electroporation chamber through a first chamber port in the bottom portion of the chamber, and the electroporation chamber can be in fluid communication with the sample container through a second chamber port in the top portion of the chamber, forming a first fluid path. Further, at least one product container can be in fluid communication with the electroporation chamber through third chamber port in the bottom portion of the chamber, and the electroporation chamber can be in fluid communication with the product container through a fourth chamber port in the top portion of the chamber, forming a second fluid path. In some embodiments, a single port electroporation chamber may be used. In other embodiments, various other suitable combinations of electrodes, spacers, ports, and containers can be used. The electroporation chamber can comprise an internal volume of about 1-10 mL; however, in other embodiments, the electroporation chamber can comprise a lesser internal volume (e.g., 0.75 mL, 0.5 mL, 0.25 mL, or less) or a greater internal volume (e.g., 15 mL, 20 mL, 25 mL, or greater). In some embodiments, the electroporation chamber and associated components can be disposable (e.g., Medical Grade Class VI materials), such as PVC bags, PVC tubing, connectors, silicone pump tubing, and the like.

Any number of containers (e.g., 1, 2, 3, 4, 5, 6, or more) can be in fluid communication with the electroporation chamber. The containers may be a collapsible, expandable, or fixed volume containers. For example, a first container (e.g., a sample source or sample container) can comprise a cell suspension and may or may not include a substance that will pass into cells in the cell suspension during electroporation. If the substance is not included, a second container comprising this substance can be included such that the substance can be mixed inline before entry into the electroporation chamber or in the electroporation chamber. In an additional configuration, another container may be attached, which can hold fluid that will be discarded. One or more additional containers can be used as the processed sample or product container. The processed sample or product container will hold cells or other products produced from the electroporation process. Further, one or more additional containers can comprise various non-sample fluids or gases that can be used to separate the sample into discrete volumes or unit volumes. The non-sample fluid or gas container can be in fluid communication with the electroporation chamber through a third and/or fourth port. The non-sample fluid or gas container may be incorporated into the processed sample container or the sample container (e.g., the non-sample fluid container can comprise a portion of the processed sample container or the sample container); and thus, the non-sample fluid or gas can be transferred from the processed sample container to another container (which may include the sample container) during the processing of the sample. The non-sample fluid or gas container may be incorporated into the chamber, as long as the compression of the non-sample fluid or gas does not affect electroporation. Further aspects of the invention may include other containers that are coupled to the sample container and may supply reagents or other samples to the chamber.

In further embodiments, the electroporation device is static electroporation and does not involve a flow of cells, but instead involves a suspension of cells in a single chamber. When such device is employed, the parameters described for flow electroporation may be used to limit thermal degradation, improve cell viability, improve efficiency of sequence modification incorporation, improve transfection efficiency and the like. Such parameters include, for example, the flow electroporation parameters described throughout the application and thermal resistance of the chamber, spacing of electrodes, ratio of combined electrode surface in contact with buffer to the distance between the electrodes, and electric field.

In certain aspects the density of cells during electroporation is a controlled variable. The cell density of cells during electroporation may vary or be varied according to, but not limited to, cell type, desired electroporation efficiency or desired viability of resultant electroporated cells. In certain aspects the cell density is constant throughout electroporation. In other aspects cell density is varied during the electroporation process. In certain aspects cell density before electroporation may be in the range of $1\times10^4$ cells/mL to $(y)\times10^4$, where y can be 2, 3, 4, 5, 6, 7, 8, 9, or 10. In other aspects the cell density before electroporation may be in the range of $1\times10^5$ cells/mL to $(y)\times10^5$, where y is 2, 3, 4, 5, 6, 7, 8, 9, or 10 (or any range derivable therein). In yet other aspects the cell density before electroporation may be in the range of $1\times10e6$ cells/mL to $(y)\times10^6$, where y can be 2, 3, 4, 5, 6, 7, 8, 9, or 10. In certain aspects cell density before electroporation may be in the range of $1\times10^7$ cells/mL to $(y)\times10^7$, where y can be 2, 3, 4, 5, 6, 7, 8, 9, or 10 or any range derivable therein. In yet other aspects the cell density before electroporation may be in the range of $1\times10^7$ cells/mL to $1\times10^8$ cells/mL, $1\times10^8$ cells/mL to $1\times10^9$ cells/mL, $1\times10^9$ cells/mL to $1\times10^{10}$ cells/mL, $1\times10^{10}$ cells/mL to $1\times10^{11}$ cells/mL, or $1\times10^{11}$ cells/mL to $1\times10^{12}$ cells/mL. In certain aspects the cell density before electroporation may be $(y)\times10^6$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 or any range derivable therein. In certain aspects the cell density before electroporation may be $(y)\times10^{10}$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100, 200, 300, 400, 500, 600, 700, 800, 900, or 1000 (or any range derivable therein).

In certain aspects the density of cells during electroporation is a controlled variable. The cell density of cells during electroporation may vary or be varied according to, but not limited to, cell type, desired electroporation efficiency or desired viability of resultant electroporated cells. In certain aspects the cell density is constant throughout electroporation. In other aspects cell density is varied during the electroporation process. In certain aspects cell density during electroporation may be in the range of $1\times10^4$ cells/mL to $(y)\times10^4$, where y can be 2, 3, 4, 5, 6, 7, 8, 9, or 10 (or any range derivable therein). In other aspects the cell density during electroporation may be in the range of $1\times10^5$ cells/mL to $(y)\times10^5$, where y is 2, 3, 4, 5, 6, 7, 8, 9, or 10 (or any range derivable therein). In yet other aspects the cell density during electroporation may be in the range of $1\times10^6$ cells/mL to $(y)\times10^6$, where y can be 2, 3, 4, 5, 6, 7, 8, 9, or 10 (or any range derivable therein). In certain aspects cell density during electroporation may be in the range of $1\times10^7$ cells/mL to $(y)\times10^7$, where y can be 2, 3, 4, 5, 6, 7, 8, 9, or 10 (or any range derivable therein). In yet other aspects the cell density during electroporation may be in the range of $1\times10^7$ cells/mL to $1\times10^8$ cells/mL, $1\times10^8$ cells/mL to $1\times10^9$ cells/mL, $1\times10^9$ cells/mL to $1\times10^{10}$ cells/mL, $1\times10^{10}$ cells/mL to $1\times10^{11}$ cells/mL, or $1\times10^{11}$ cells/mL to $1\times10^{12}$ cells/mL. In certain aspects the cell density during electroporation may be $(y)\times10^6$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 (or any range derivable therein). In certain aspects the cell density during electroporation may be $(y)\times10^{10}$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100, 200, 300, 400, 500, 600, 700, 800, 900, or 1000 (or any range derivable therein).

In certain aspects cell density after electroporation may be in the range of $1\times10^4$ cells/mL to $(y)\times10^4$, where y can be 2, 3, 4, 5, 6, 7, 8, 9, or 10 (or any range derivable therein). In other aspects the cell density after electroporation may be in the range of $1\times10^5$ cells/mL to $(y)\times10^5$, where y is 2, 3, 4, 5, 6, 7, 8, 9, or 10 (or any range derivable therein). In yet other aspects the cell density after electroporation may be in the range of $1\times10^6$ cells/mL to $(y)\times10^6$, where y can be 2, 3, 4, 5, 6, 7, 8, 9, or 10 (or any range derivable therein). In certain aspects cell density after electroporation may be in the range of $1\times10^7$ cells/mL to $(y)\times10^7$, where y can be 2, 3, 4, 5, 6, 7, 8, 9, or 10 (or any range derivable therein). In yet other aspects the cell density after electroporation may be in the range of $1\times10^7$ cells/mL to $1\times10^8$ cells/mL, $1\times10^8$ cells/mL to $1\times10^9$ cells/mL, $1\times10^9$ cells/mL to $1\times10^{10}$ cells/mL, $1\times10^{10}$ cells/mL to $1\times10^{11}$ cells/mL, or $1\times10^{11}$ cells/mL to $1\times10^{12}$ cells/mL (or any range derivable therein). In certain aspects the cell density after electroporation may be $(y)\times10e6$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 (or any range derivable therein). In certain aspects the cell density after electroporation may be $(y)\times10^{10}$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100, 200, 300, 400, 500, 600, 700, 800, 900, or 1000 (or any range derivable therein).

In certain embodiments electroporation can be carried out on any prokaryotic or eukaryotic cell. In some aspects electroporation involves electroporation of a human cell. In other aspects electroporation involves electroporation of an animal cell. In certain aspects electroporation involves electroporation of a cell line or a hybrid cell type. In some aspects the cell or cells being electroporated are cancer cells, tumor cells or immortalized cells. In some instances tumor, cancer, immortalized cells or cell lines are induced and in other instances tumor, cancer, immortalized cells or cell lines enter their respective state or condition naturally. In certain aspects the cells or cell lines electroporated can be A549, B-cells, B16, BHK-21, C2C12, C6, CaCo-2, CAP/, CAP-T, CHO, CHO2, CHO-DG44, CHO-K1, CHO-DUXB11 COS-1, Cos-7, CV-1, Dendritic cells, DLD-1, Embryonic Stem (ES) Cell or derivative, H1299, HEK, 293, 293FT, Hep G2, Hematopoietic Stem Cells, HOS, Huh-7, Induced Pluripotent Stem (iPS) Cell or derivative, Jurkat, K562, L5278Y, LNCaP, MCF7, MDA-MB-231, MDCK, Mesenchymal Cells, Min-6, Monocytic cell, Neuro2a, NIH 3T3, NIH3T3L1, NK-cells, NSO, Panc-1, PC12, PC-3, Peripheral blood cells, Plasma cells, Primary Fibroblasts, RBL, Renca, RLE, SF21, SF9, SH-SY5Y, SK-MES-1, SK-N-SH, SL3, SW403, Stimulus-triggered Acquisition of Pluripotency (STAP) cell or derivate SW403, T-cells, THP-1, Tumor cells, U2OS, U937, or Vero cells.

In certain embodiments, the cell is one that is known in the art to be difficult to transfect. Such cells are known in the art and include, for example, primary cells, insect cells, SF9 cells, Jurkat cells, CHO cells, stem cells, slowly dividing cells, and non-dividing cells.

In some embodiments, the cell is a hematopoietic stem or progenitor cell. Due to the significant medical potential of hematopoietic stem and progenitor cells, substantial work has been done to try to improve methods for the differentiation of hematopoietic progenitor cells from embryonic stem cells. In the human adult, hematopoietic stem cells present primarily in bone marrow produce heterogeneous populations of actively dividing hematopoietic (CD34+) progenitor cells that differentiate into all the cells of the blood system. In an adult human, hematopoietic progenitors proliferate and differentiate resulting in the generation of hundreds of billions of mature blood cells daily. Hematopoietic progenitor cells are also present in cord blood. In vitro, human embryonic stem cells may be differentiated into hematopoietic progenitor cells. Hematopoietic progenitor cells may also be expanded or enriched from a sample of peripheral blood. The hematopoietic cells can be of human origin, murine origin or any other mammalian species.

In some instances certain number of cells can be electroporated in a certain amount of time. Given the flexibility, consistency and reproducibility of the described platform up to or more than about $(y)\times10^4$, $(y)\times10^5$, $(y)\times10^6$, $(y)\times10^7$, $(y)\times10^8$, $(y)\times10^9$, $(y)\times10^{10}$, $(y)\times10^{11}$, $(y)\times10^{12}$, $(y)\times10^{13}$, $(y)\times10^{14}$, or $(y)\times10^{15}$ cells (or any range derivable therein) can be electroporated, where y can be any of 1, 2, 3, 4, 5, 6, 7, 8, or 9 (or any range derivable therein). in less than 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 seconds (or any range derivable therein). In other instances, up to or more than about $(y)\times10^4$, $(y)\times10^5$, $(y)\times10^6$, $(y)\times10^7$, $(y)\times10^8$, $(y)\times10^9$, $(y)\times10^{10}$, $(y)\times10^{11}$, $(y)\times10^{12}$, $(y)\times10^{13}$, $(y)\times10^{14}$, or $(y)\times10^{15}$ cells (or any range derivable therein) can be electroporated, where y can be any of 1, 2, 3, 4, 5, 6, 7, 8, or 9 (or any range derivable therein), in less than 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100. 110, or 120 minutes (or any range derivable therein). In yet other aspects, up to or more than about $(y)\times10^4$, $(y)\times10^5$, $(y)\times10^6$, $(y)\times10^7$, $(y)\times10^8$, $(y)\times10^9$, $(y)\times10^{10}$, $(y)\times10^{11}$, $(y)\times10^{12}$, $(y)\times10^{13}$, $(y)\times10^{14}$, or $(y)\times10^{15}$ cells (or any range derivable therein) can be electroporated, where y can be any of 1, 2, 3, 4, 5, 6, 7, 8, or 9 (or any range derivable therein). in less than 1, 2, 3, 4, 5, 6, 7, 8, 9, 10, 11, 12, 13, 14, 15, 16, 17, 18, 19, 20, 21, 22, 23, or 24 hours (or any range derivable therein).

The expression '$(y)\times10e$' is understood to mean, a variable 'y' that can take on any numerical value, multiplied by 10 that is raised to an exponent value, e. For example, $(y)\times10^4$, where y is 2, is understood to mean $2\times10^4$, which is equivalent to $2\times10,000$, equal to 20,000. $(y)\times10e4$ can also be written as $(y)*10e4$ or $(y)\times10^4$ or $(y)*10^4$.

Volumes of cells or media may vary depending on the amount of cells to be electroporated, the number of cells to be screened, the type of cells to be screened, the type of protein to be produced, amount of protein desired, cell viability, and certain cell characteristics related to desirable cell concentrations. Examples of volumes that can be used in methods and compositions include, but are not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 ml or L (or any range derivable therein), and any range derivable therein. Containers that may hold such volumes are contemplated for use in embodiments described herein. Such containers include, but are not limited to, cell culture dishes, petri dishes, flasks, biobags, biocontainers, bioreactors, or vats. Containers for large scale volumes are particularly contemplated, such as those capable of holding greater than 10 L or more. In certain embodiments, volumes of 100 L or more are used.

It is specifically contemplated that electroporation of cells by methods described herein provide benefits of increased efficiency and/or reduced toxicity. Such measurements may be made by measuring the amount of cells that incorporated the genomic DNA sequence modification, measuring the amount of cells that express the marker, and/or measuring the viability of the cells after electroporation.

In some embodiments, the efficiency of the sequence modification is greater than about 2, 3, 4, 5, 6, 7, 8, 9, 10, 15, 20, 25, 30, 35, 40, 45, or 50%. The efficiency of the sequence modification can be measured by determining the number of cells with the sequence modification and dividing by the total number of cells. Incorporation of the genome DNA sequence modification can be determined by methods known in the art such as direct genomic DNA sequencing, differential restriction digestion (if the sequence modification adds, removes, or changes a restriction enzyme site), gel electrophoresis, capillary array electrophoresis, MALDI-TOF MS, dynamic allele-specific hybridization, molecular beacons, restriction fragment length polymorphism, primer extension, temperature gradient gel electrophoresis, and the like.

In other embodiments, the cell viability after electroporation is at least 20, 25, 30, 35, 40, 45, 50, 55, 60, 65, 70, 75, 80, or 85%. Cell viability can be measured by methods known in the art. For example, cells can be counted before and after electroporation by a cell counter apparatus. In other embodiments, apoptosis is measured. It is believed that introduction of large amounts of nucleic acids may induce apoptosis. It is contemplated that methods described herein will lead to less apoptosis than other methods in the art. In certain embodiments, the amount of cells exhibiting apoptosis after electroporation is less than 50, 45, 40, 35, 30, 25, 20, 15, 10, or 5%. Apoptosis refers to the specific process of programmed cell death and can be measured by methods known in the art. For example, apoptosis may be measured by Annexin V assays, activated caspase 3/7 detection assays, and Vybrant® Apoptosis Assay (Life Technologies).

In further embodiments, the percentage of cells that express the nucleic acid encoding the marker is greater than about 10, 15, 20, 25, 30, 35, 40, 45, 50, 55, 60, 65, 70, 75, 80, 85, or 90%.

When a specific embodiment of the disclosure includes a range or specific value, as described herein, it is specifically contemplated that ranges and specific values (i.e. concentrations, lengths of nucleic acids, and percentages) may be excluded in embodiments of the invention. It is also contemplated that, when the disclosure includes a list of elements (e.g. cell types), embodiments of the invention may specifically exclude one or more elements in the list.

3. Other Non-Chemical Methods

Cell squeezing is a transfection method which enables delivery of molecules into cells by a gentle squeezing of the cell membrane. It is a high throughput vector-free microfluidic platform for intracellular delivery. It does not rely on exogenous materials or electrical fields.

Sonoporation uses high-intensity ultrasound to induce pore formation in cell membranes. This pore formation is attributed mainly to the cavitation of gas bubbles interacting with nearby cell membranes since is enhanced by the addition of ultrasound contrast agent, a source of cavitation nuclei.

Optical transfection is a method where a tiny (~1 µm diameter) hole is transiently generated in the plasma membrane of a cell using a highly focused laser. In this technique, one cell at a time is treated, making it particularly useful for single cell analysis.

Hydrodynamic delivery in mice and rats, but to a lesser extent in larger animals, DNA most often in plasmids, including transposons, can be delivered to the liver using hydrodynamic injection that involves infusion of a relatively large volume in the blood in less than 10 seconds; nearly all of the DNA is expressed in the liver by this procedure.

B. Chemical-Based Transfection Methods

Chemical-based transfection can be divided into several kinds: cyclodextrin, polymers, liposomes, or nanoparticles (with or without chemical or viral functionalization).

One of the cheapest methods uses calcium phosphate. HEPES-buffered saline solution (HeBS) containing phosphate ions is combined with a calcium chloride solution containing the DNA to be transfected. When the two are combined, a fine precipitate of the positively charged calcium and the negatively charged phosphate will form, binding the DNA to be transfected on its surface. The suspension of the precipitate is then added to the cells to be transfected (usually a cell culture grown in a monolayer). By a process not entirely understood, the cells take up some of the precipitate, and with it, the DNA.

Other methods use highly branched organic compounds, so-called dendrimers, to bind the DNA and get it into the cell.

A very efficient method is the inclusion of the DNA to be transfected in liposomes, i.e. small, membrane-bounded bodies that are in some ways similar to the structure of a cell and can actually fuse with the cell membrane, releasing the DNA into the cell. For eukaryotic cells, transfection is better achieved using cationic liposomes (or mixtures), because the cells are more sensitive.

Another method is the use of cationic polymers such as DEAE-dextran or polyethylenimine. The negatively charged DNA binds to the polycation and the complex is taken up by the cell via endocytosis.

C. Particle-Based Methods

A direct approach to transfection is the gene gun, where the DNA is coupled to a nanoparticle of an inert solid (commonly gold) which is then "shot" directly into the target cell's nucleus.

Magnetofection, or Magnet assisted transfection is a transfection method, which uses magnetic force to deliver DNA into target cells. Nucleic acids are first associated with magnetic nanoparticles. Then, application of magnetic force drives the nucleic acid particle complexes towards and into the target cells, where the cargo is released.

Impalefection is carried out by impaling cells by elongated nanostructures and arrays of such nanostructures such as carbon nanofibers or silicon nanowires which have been functionalized with plasmid DNA.

Another particle-based method of transfection is known as particle bombardment. The nucleic acid is delivered through membrane penetration at a high velocity, usually connected to microprojectiles.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Targeted Integration of Transgene in Genomic DNA with the Help of Specific Nuclease and Plasmid Donor DNA Because of the therapeutic potential, there is high demand for efficient-targeted integration of transgene in cellular genomic DNA. In addition to the therapeutic potential, efficient, targeted integration of transgene has applicability for protein production (e.g. antibody production). For targeted integration of a transgene, the transgene is typically delivered on a large piece of DNA or a plasmid, which may have toxicity in certain cells, such as primary cells, stem cells, hematopoietic cells, or immune cells. Therefore, for targeted integration of transgenes to be therapeutically relevant, the method must provide high integration efficiency and specificity in the target genomic DNA of therapeutically relevant cells.

It was hypothesized that cells, such as hematopoietic cells or immune cells, may have different sensitivities to transfection with plasmid DNA during the process of activation. It was contemplated that there may be a time window in which expanded hematopoietic cells may exhibit increased tolerance and decreased toxicity to plasmid DNA transfection.

To test this hypothesis, targeted integration was performed in K562 cells and human T cells. A guide RNA (gRNA) Cas9 were used. The gRNA template was made by PCR amplification with primers conjugated with T7 promoter. The primers used were: SM285.AAVS1.g2.F: ttaatacgactcactataGGGGCCACTAGGGACAGGAT (SEQ ID NO:19) and SM212.sgRNA.R: aaaagcaccgactcggtgcc (SEQ ID NO:20). The Cas9 template was obtained by endonuclease-linearization (XhoI 1) of the Cas9 plasmid. mRNA was then made by mMESSAGE mMACHINE T7 ULTRA Kit (Available commercially from Ambion). The donor DNA used was plasmid DNA comprising GFP.

A. Targeted Integration of GFP Transgene into K562

Figure 1B:
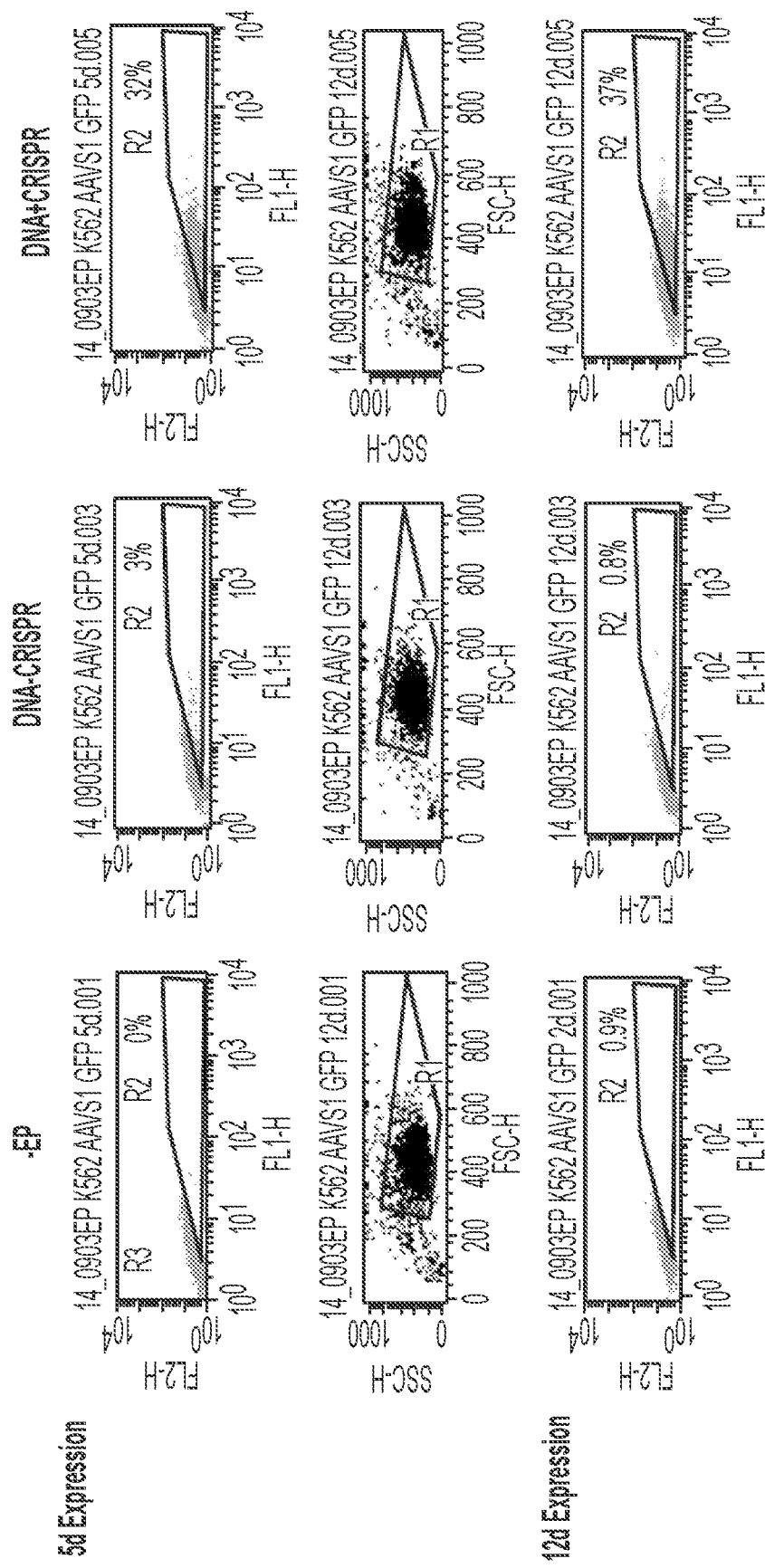
Figure 14:
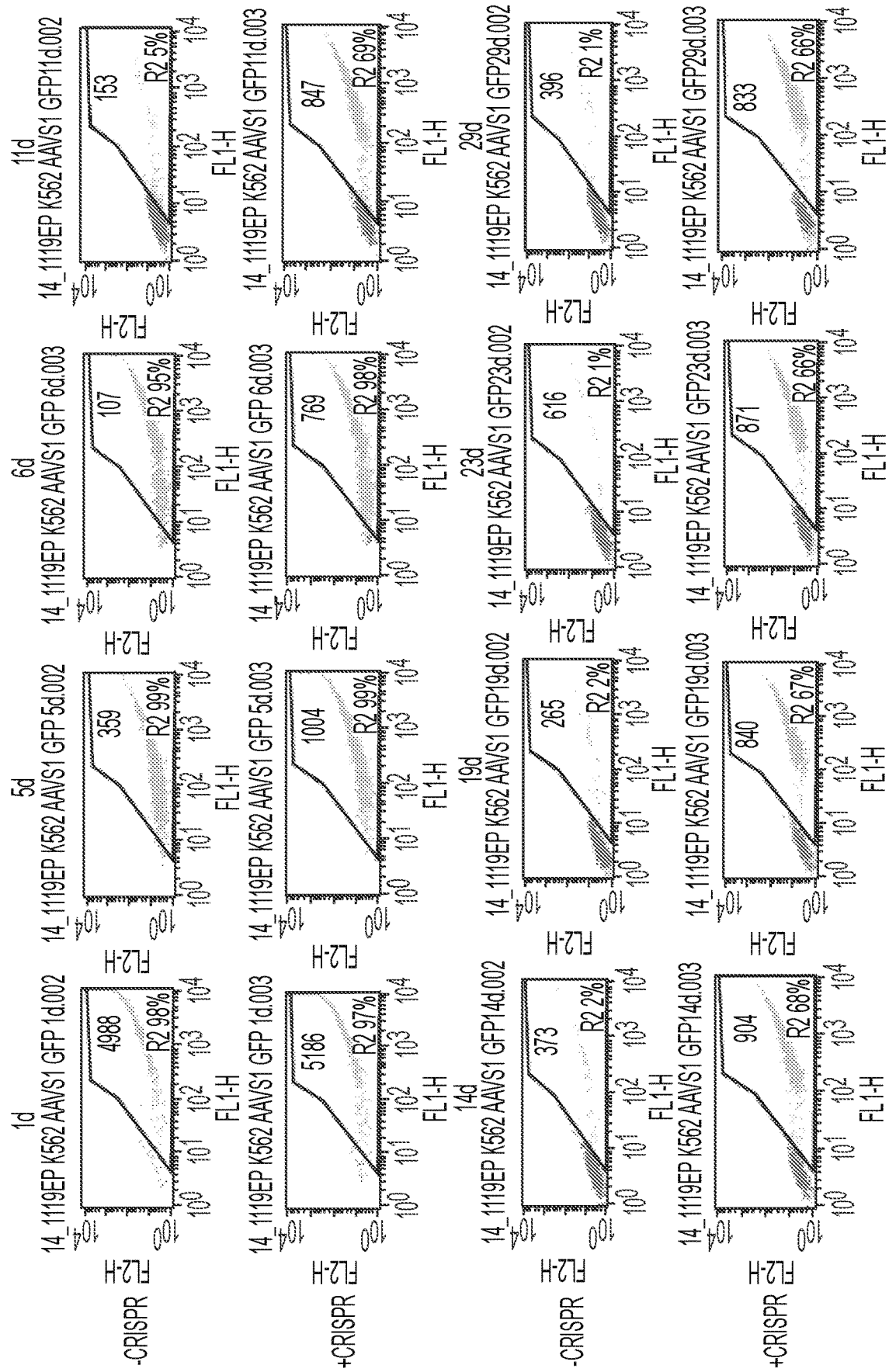
FIG. 14: Targeted Integration of PGK-eGFP-PolyA in AAVS1 Site of K562 by mRNA-CRISPR and Donor Plasmid DNA (Without Selection): Shown is FACS analysis of K562 cells transfected with PGK-eGFP-PolyA and with (+CRISPR, second and fourth rows) or without (−CRISPR, first and third rows) mRNA-CRISPR system. FACS analysis was done on the cells at one, five, six, eleven, fourteen, nineteen, twenty-three, and twenty-nine days post transfection. As shown in this figure, only cells transfected with the donor plasmid DNA and the CRISPR system showed stable GFP expression beyond six or eleven days post transfection.

FIG. 1 shows that GFP is expressed in 27%, 32%, and 37% of cells at 1, 5, and 12 days post transfection by electroporation. As expected, no significant GFP expression was seen in cells which had not undergone electroporation (−EP), but 35% of cells expressed GFP in transfection that did not include the guide RNA and Cas9, which confer targeted integration. However, this expression was transient and so significant amount of GFP expression was seen at the subsequent tested time-points of 5 and 12 days. Only cells transfected with the CRISPR system retained a significant level of GFP expression past the 1 day time-point (FIG. 1). This was further confirmed in an additional experiment, in which the PGK-eGFP-PolyA plasmid was targeted into the AAVS1 site of K562 cells using the CRISPR system. As shown in FIG. 14, targeted integration (+CRISPR) allows for the stable expression of GFP at time-points of least 29 days post-transfection (FIG. 14, second and fourth rows).

The transfected K562 cells were tested for viability, expression, and mean fluorescent intensity (FIG. 13A-C). Plasmid transfected into K562 cells did not show any reduction in cell viability (FIG. 13A). As shown in FIGS. 13B-13C, only K562 cells transfected with the CRISP system retained a significant amount of GFP expression beyond 5 days post transfection. This is expected, since the co-transfection of the transgene with the CRISPR system allows for stable, site-specific integration of the transgene. The expression of the transgene remains in these cells without selective pressure.

In summary, the plasmid DNA did not induce significant cytotoxicity of K562 cells and efficient targeted integration was seen (30-40%) without selection of the cells.

B. Targeted Integration of GFP Transgene into Fibroblasts

Figure 12A:
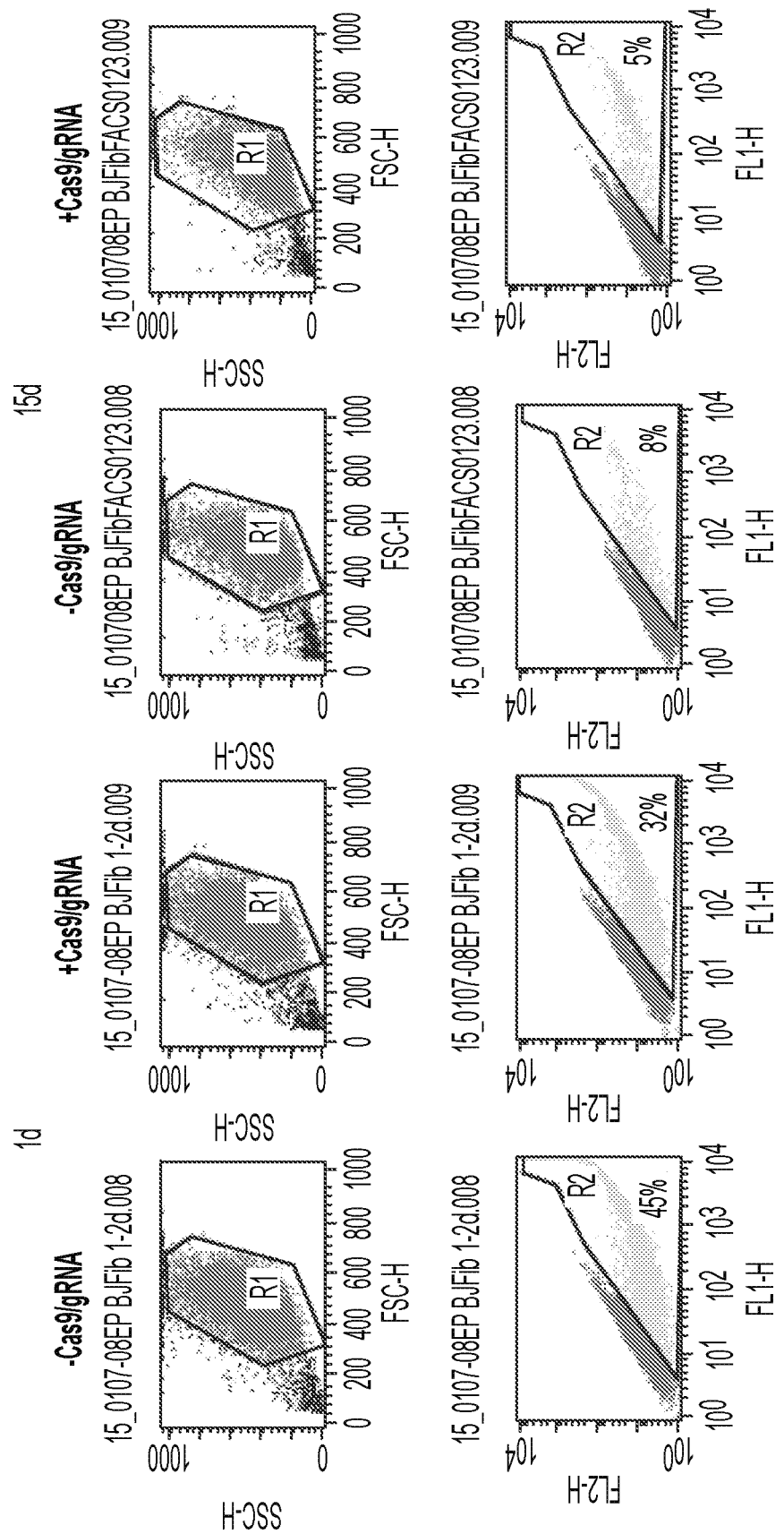
FIGS. 12A-12B: Targeted Integration of PGK-eGFP-PolyA in AAVS1 Site of Human Primary Fibroblast by mRNA-CRISPR and Donor Plasmid DNA (Without Selection): Shown is FACS analysis of human primary fibroblasts transfected with PGK-eGFP-PolyA and with (+Cas9/gRNA) or without (−Cas9/gRNA) mRNA-CRISPR system. As shown in this figure, only cells transfected with the donor plasmid DNA and the CRISPR system showed stable GFP expression beyond 15 days post transfection (compare row 4, first plot to second plot for expression of GFP 23 days post transfection and row 4, third plot to fourth plot for expression of GFP 26 days post transfection).
Figure 12B:
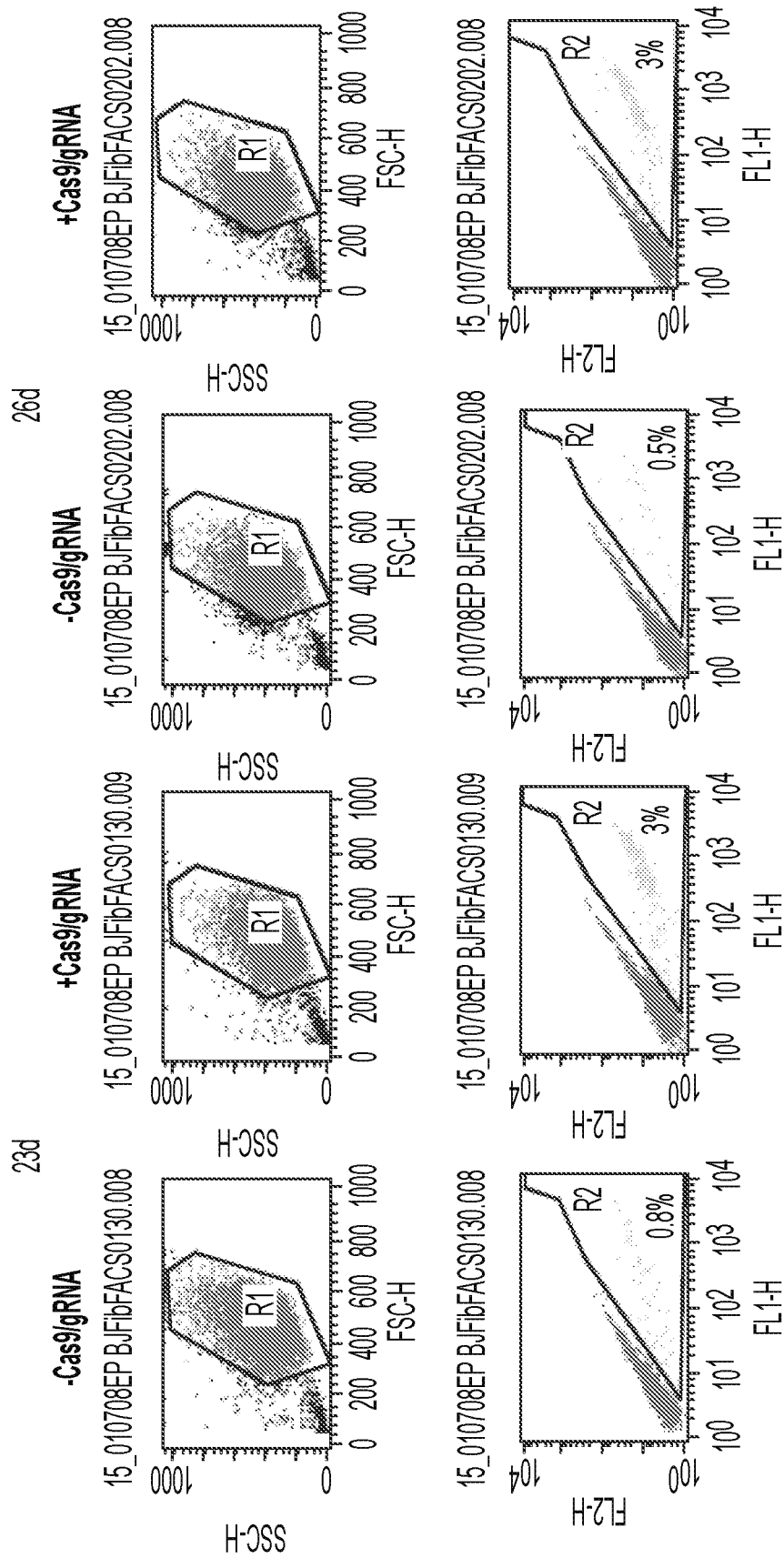

To test whether targeted integration of a GFP transgene (PGK-eGFP-PolyA) could be integrated into fibroblasts, human fibroblasts were electroporated with GFP plasmid DNA (PGK-eGFP-PolyA) with (+CasO/gRNA) or without (−Cas9/gRNA) the CRISPR system. A comparable level of GFP expression was seen in the two experiments up to 15 days post transfection, but only cells transfected with the CRISPR system retained significant GFP expression at 23 and 26 days post transfection (FIG. 12).

C. Targeted Integration of GFP Transgene into Human T Cells

Figure 2A:
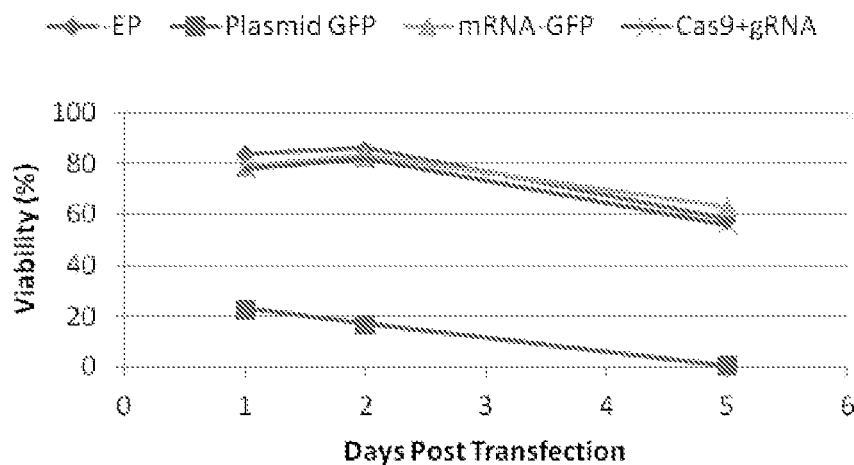
FIG. 2A-C: DNA Plasmid induced significant cytotoxicity of T cells expanded for 10 days prior to electroporation. Shows the viability (FIG. 2A), proliferation (FIG. 2B), and GFP Expression (FIG. 2C) of non-transfected control cells (−EP) or cells transfected by electroporation with plasmid GFP DNA, mRNA-GFP, or Cas9/gRNA.
Figure 2B:
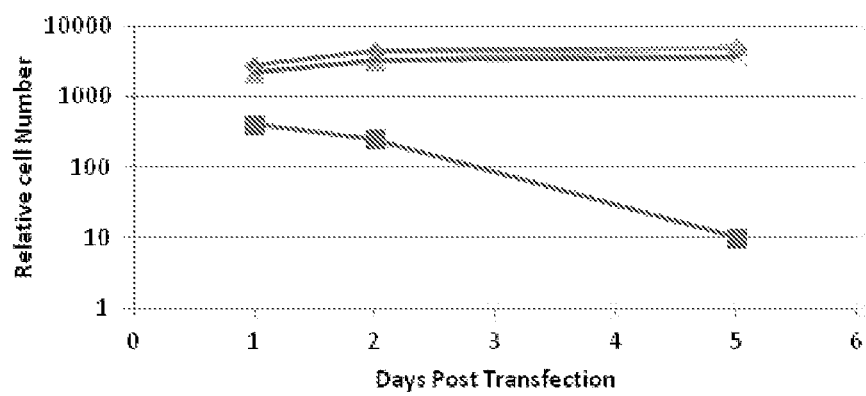
Figure 2C:
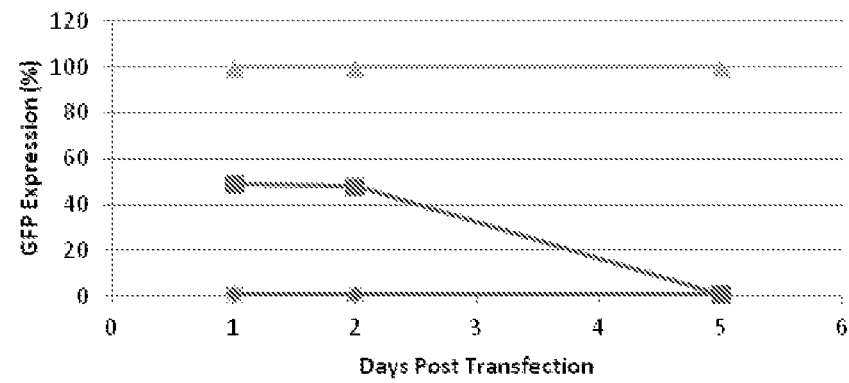

As shown in FIG. 2A-C, human T cells exhibited reduced viability (FIG. 2A), reduced proliferation (FIG. 2B), and reduced GFP expression (FIG. 2C) after transfection with plasmid DNA. However, these negative effects were overcome in cells transfected with mRNA-GFP, suggesting that the plasmid DNA was a source of toxicity.

Figure 3A:
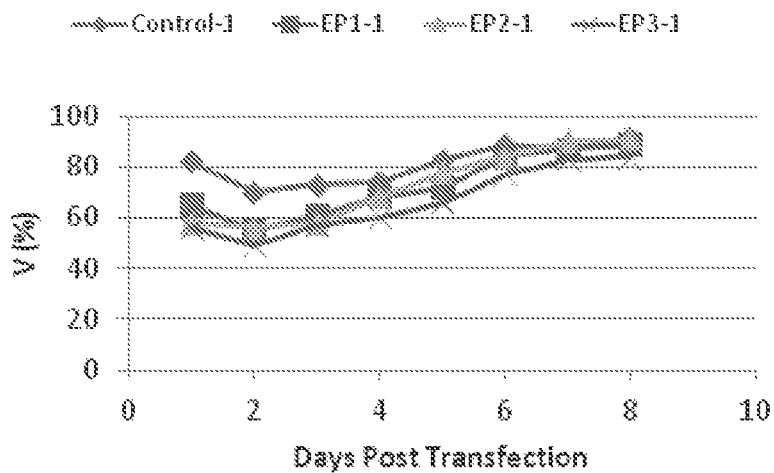
FIG. 3A-C: Transfection window of expanded T cells after activation. T cells were activated by DYNABEADS® Human T-Activator CD3/CD28 (available commercially from Life Technologies) and were then transfected by electroporation with plasmid DNA at either one day, two days, or three days after activation. The figures show the viability of the cells transfected at one day (FIG. 3A), two days (FIG. 3B), and three days (FIG. 3C) post activation.
Figure 3B:
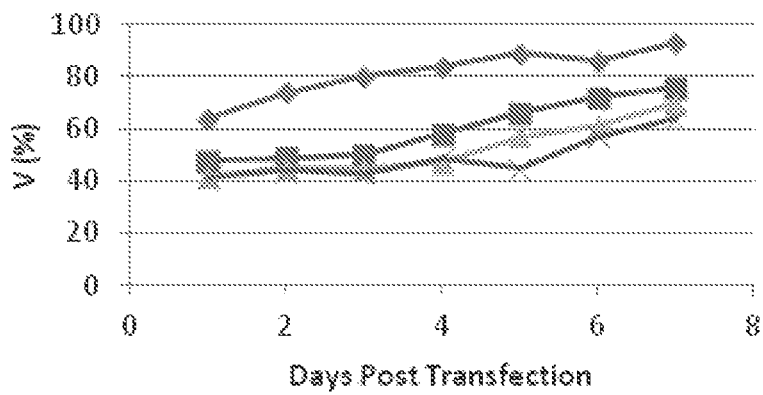
Figure 3C:
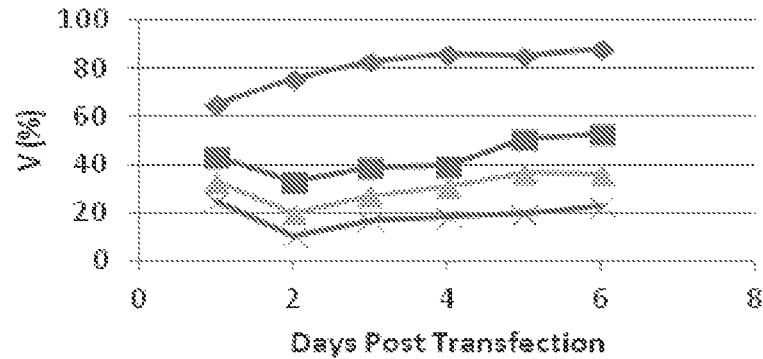
Figure 4A:
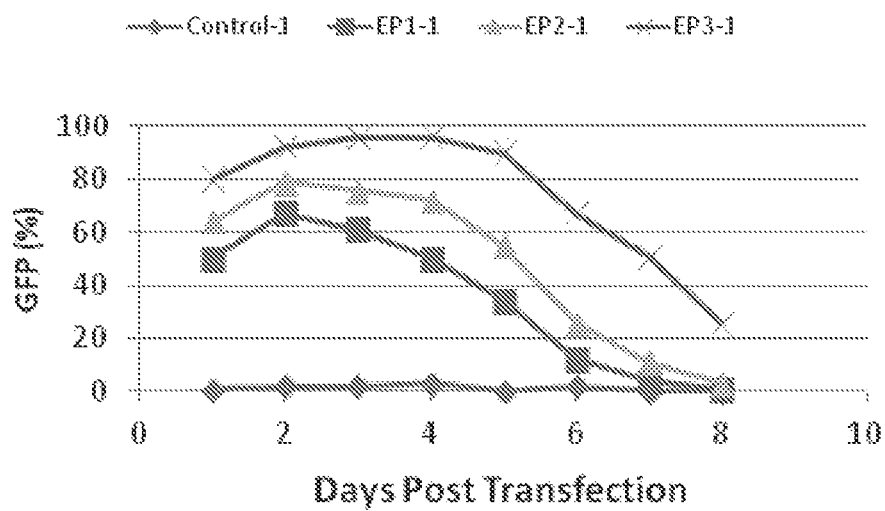
FIG. 4A-C: Transfection window of expanded T cells after activation. T cells were activated by DYNABEADS® Human T-Activator CD3/CD28 and were then transfected by electroporation with plasmid DNA at either one day, two days, or three days after activation. The figures show the percentage of cells expressing GFP after transfection at one day (FIG. 4A), two days (FIG. 4B), and three days (FIG. 4C) post activation.
Figure 4B:
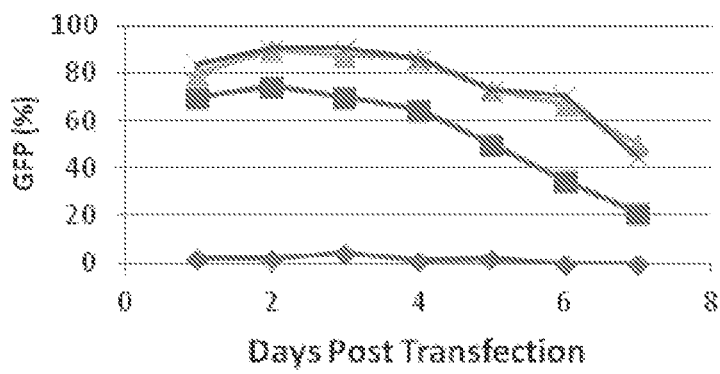
Figure 4C:
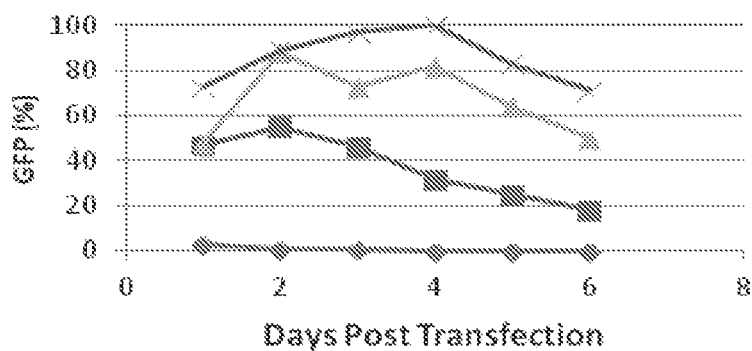
Figure 5A:
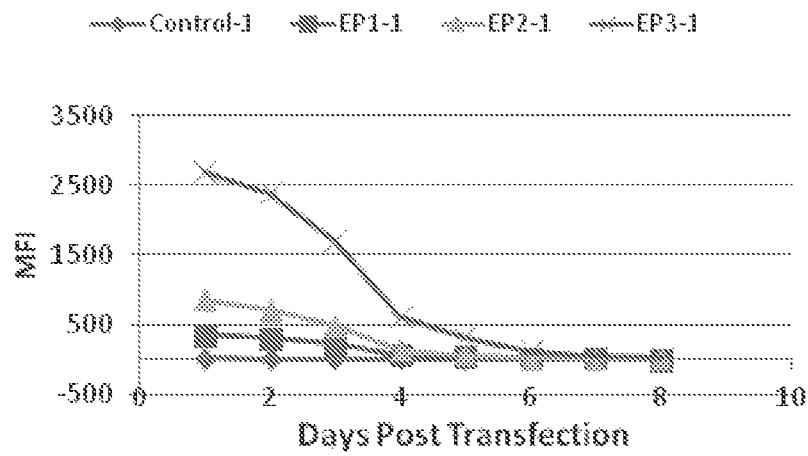
FIG. 5A-C: T cells were activated by DYNABEADS® Human T-Activator CD3/CD28 and were then transfected by electroporation with plasmid DNA at either one day, two days, or three days after activation. The figures show the mean fluorescent intensity (MFI) of transfected cells at one day (FIG. 5A), two days (FIG. 5B), and three days (FIG. 5C) post activation.
Figure 5B:
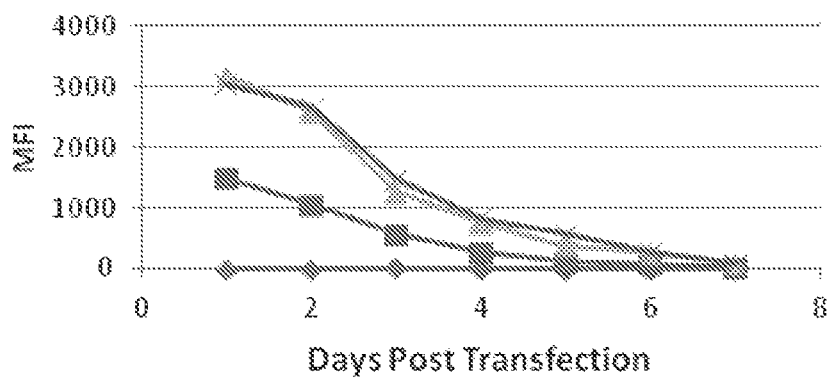
Figure 5C:
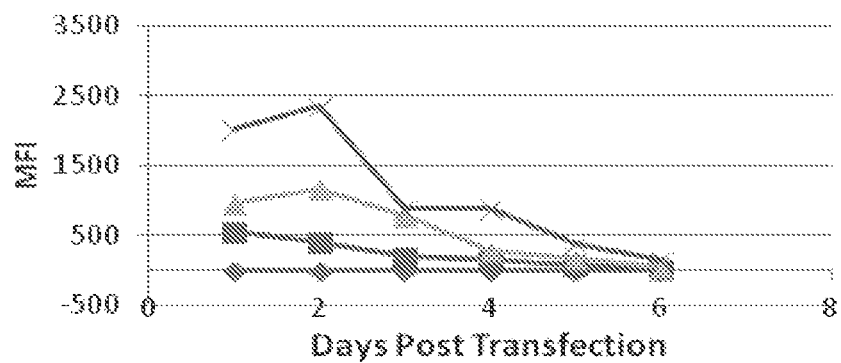

It was then tested whether cells transfected with plasmid DNA at different time points after activation of the cells affected the viability of the cells. T cells electroporated 1 day after activation by DYNABEADS® Human T-Activator CD3/CD28 (available commercially from Life Technologies) exhibited no significant reduction in viability compared to control (FIG. 3A). Transfection at 2 days post activation resulted in a decrease in cell viability (FIG. 3B) compared to one day post activation, but the cell viability was still over 40% in each tested sample. At three days, there is a further reduction of cell viability (FIG. 3C). These data indicate that activation of the cells reduces toxicity associated with plasmid DNA transfection. When the same cells were tested for GFP expression (FIG. 4A-C) and mean fluorescent intensity (MFI, FIG. 5A-C), the highest level of GFP expression was seen when cells were transfected two days post activation (FIG. 4B and FIG. 5B).

Figure 6A:
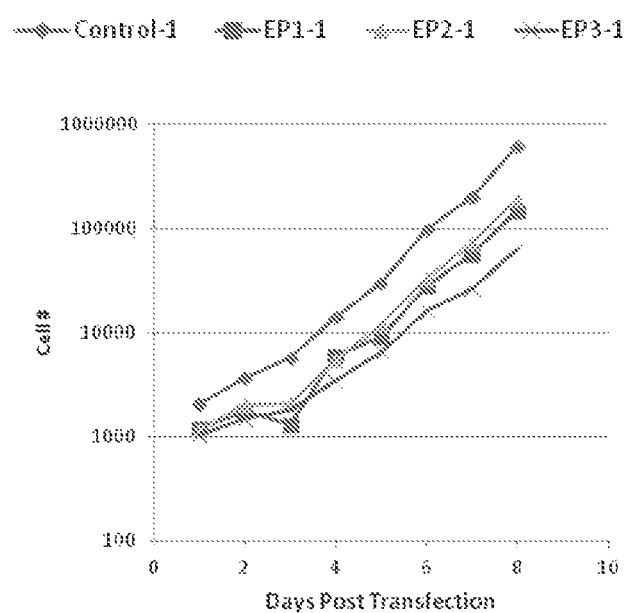
FIG. 6A-C: Transfection window of expanded T cells after activation. T cells were activated by DYNABEADS® Human T-Activator CD3/CD28 and were then transfected by electroporation with plasmid DNA at either one day, two days, or three days after activation. The figures show the proliferation of cells after transfection (results are from three independent transfection experiments and one control experiment with no plasmid DNA) at one day (FIG. 6A), two days (FIG. 6B), and three days (FIG. 6C) post activation.
Figures 6B, 6C:
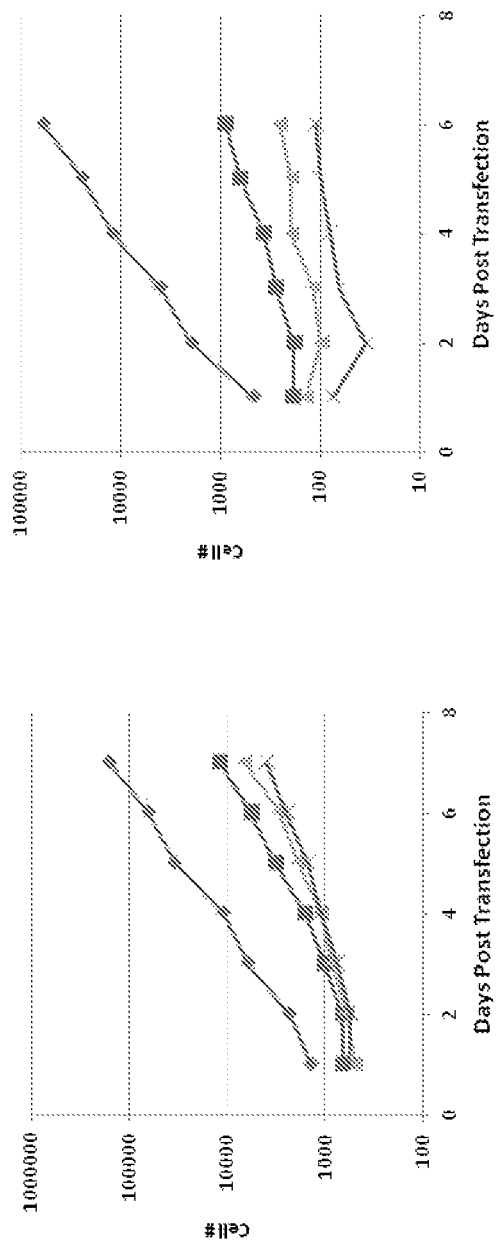

The transfection window was further studied in expanded T cells. T cells were activated as described previously and were electroporated at either one day, two days or three days post activation. FIG. 6A-C shows the proliferation of the cells electroporated at the different time points. Cells electroporated at one day post activation exhibited the most cell proliferation (FIG. 6A), and cells electroporated at three days post activation exhibited the least amount of cell proliferation. These data demonstrate that activation of the cells, prior to transfection, allows for better tolerance of the plasmid DNA.

Figure 7A:
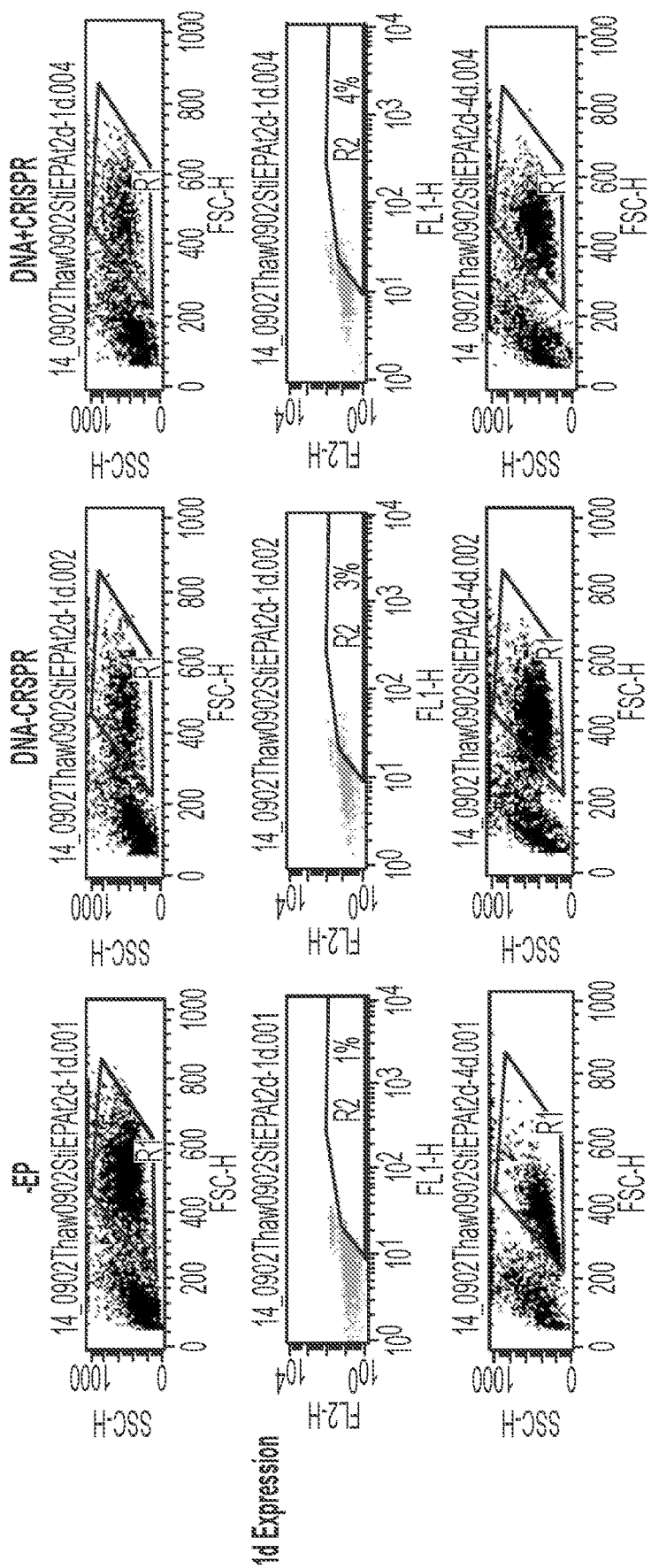
FIGS. 7A-7B: Targeted Integration of GFP in Expanded T cells by mRNA-CRISPR (gRNA/Cas9-AAVS1) and Plasmid GFP DNA. Expanded T cells were activated according to methods previous described and electroporated two days following activation.
Figure 7B:
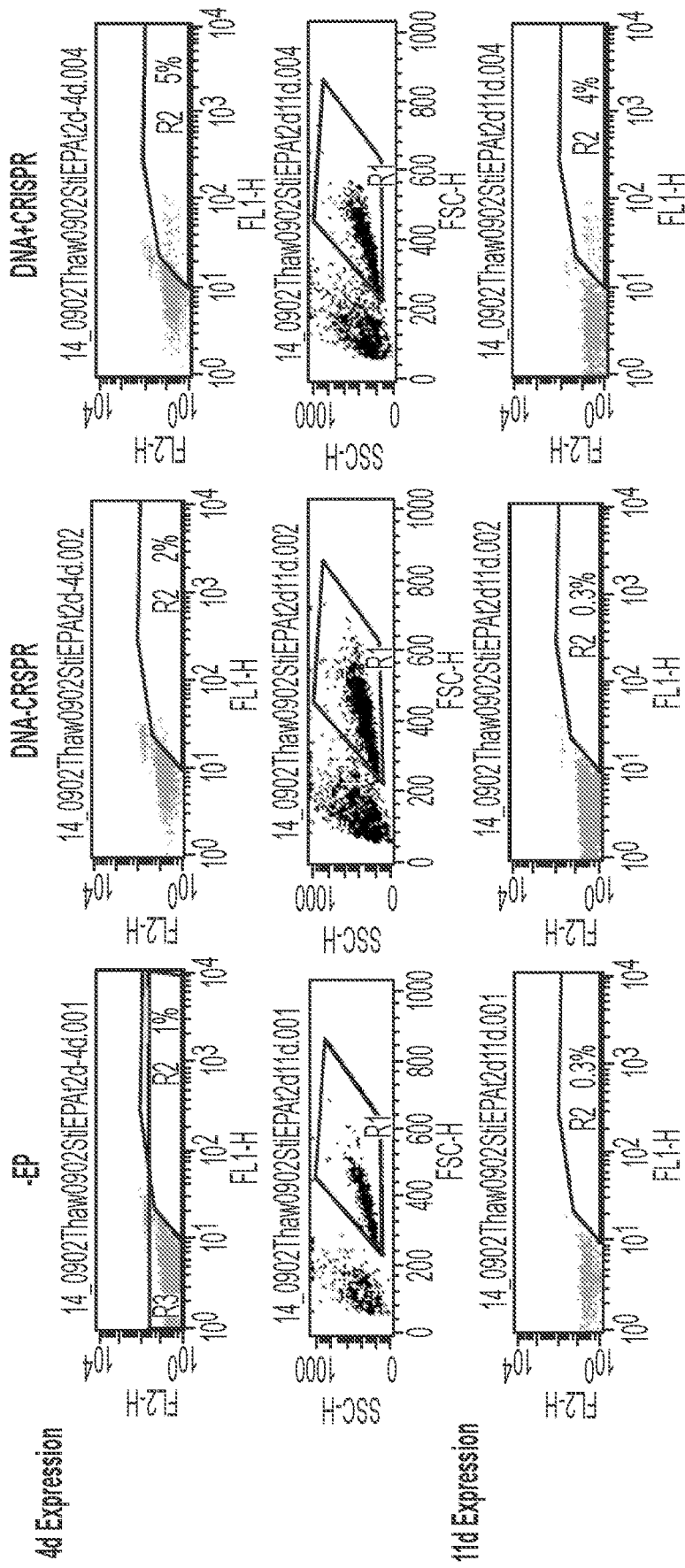
Figure 8:
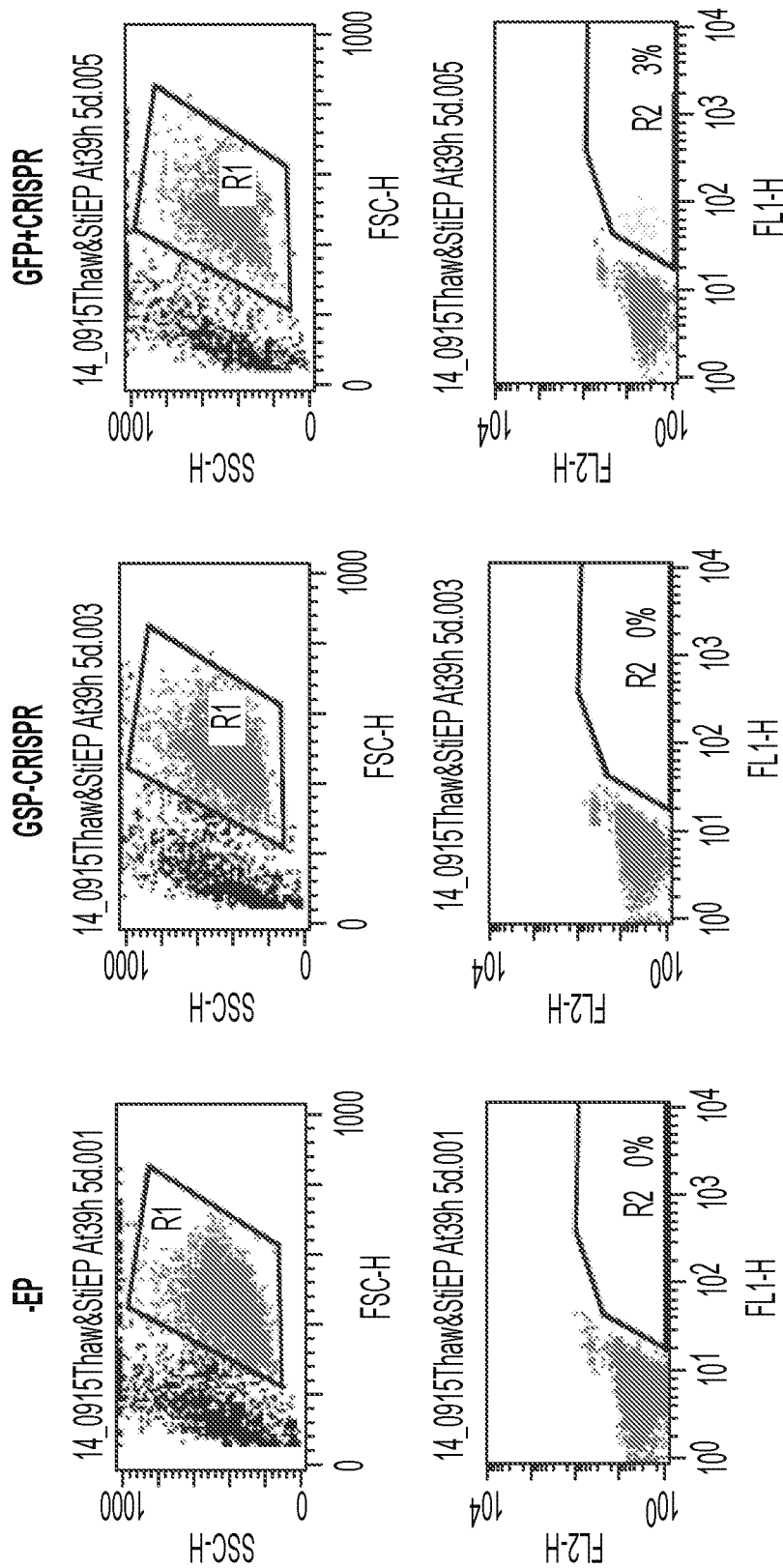
FIG. 8: Targeted Integration of GFP in Expanded T cells by mRNA-CRISPR (gRNA/Cas9-AAVS1) and Plasmid GFP DNA. Expanded T cells were activated according to methods previous described and electroporated two days following activation.

It was next tested whether targeted integration of a transgene could be performed by electroporation of T cells after activation. Expanded T cells were activated as previously described and then electroporated with 100 µg/ml of GFP plasmid DNA at two days post activation. As shown in FIG. 7, the no-electroporation control (−EP) exhibited a low level of background fluorescence. 3% of cells transfected with GFP plasmid DNA but not the CRISPR system (gRNA/Cas9) that allows for site-specific integration at the AAVS1 site exhibited GFP fluorescence one day after transfection. However, the expression of GFP in these cells was transient and decreased at four days post transfection to 2% and to 0.3% at eleven days post transfection. In contrast, cells with the CRISPR system maintained GFP expression at eleven days post transfection. 4, 5, and 4% of these cells exhibited GFP expression at one, four, and eleven days, respectively, post transfection. This experiment was repeated, and the results confirmed that cells transfected with GFP plasmid DNA and the CRISPR complex maintained GFP expression (2.3% of cells) 6 days after transfection, while cells transfected with GFP plasmid DNA alone did not express GFP 6 days after transfection (FIG. 8).

Figure 9A:
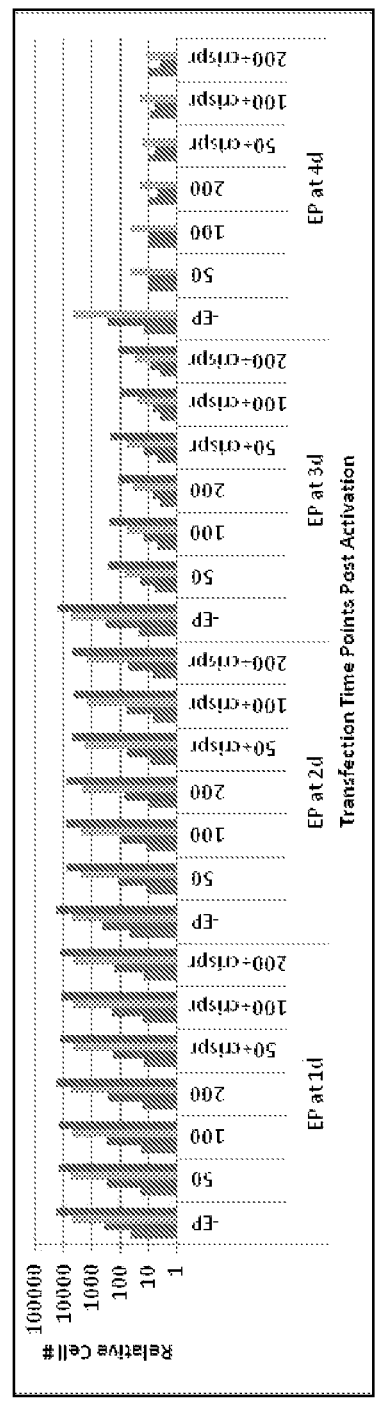
FIG. 9A-D: Targeted integration of GFP in expanded T cells by mRNA-CRISPR (gRNA/Cas9) targeting the AAVS1 site and GFP plasmid DNA (donor DNA). Cells were activated as previously described and transfected at one, two, three, and four days post-activation. 50, 100, or 200 µg/ml of GFP plasmid DNA was used as indicated for these experiments. The proliferation (FIG. 9A), percentage of GFP-expressing cells (FIG. 9B), relative number of integrated events (FIG. 9C), and cell viability (FIG. 9D) was measured for the transfected cells at three, six, ten, and fourteen days post activation. The relative number of integrated events is calculated as cell number multiplied by the percentage of GFP-positive cells.
Figure 9B:
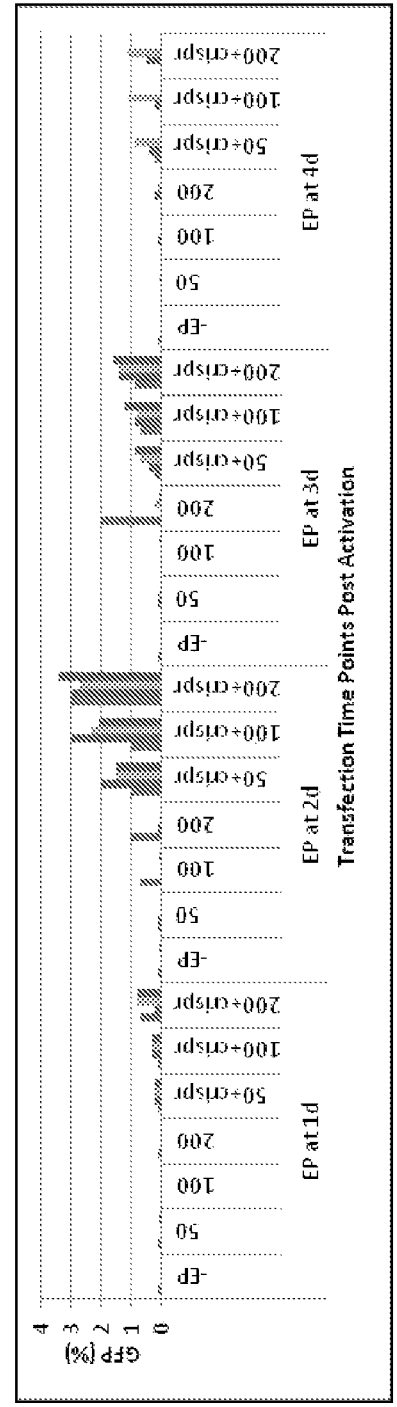
Figure 9C:
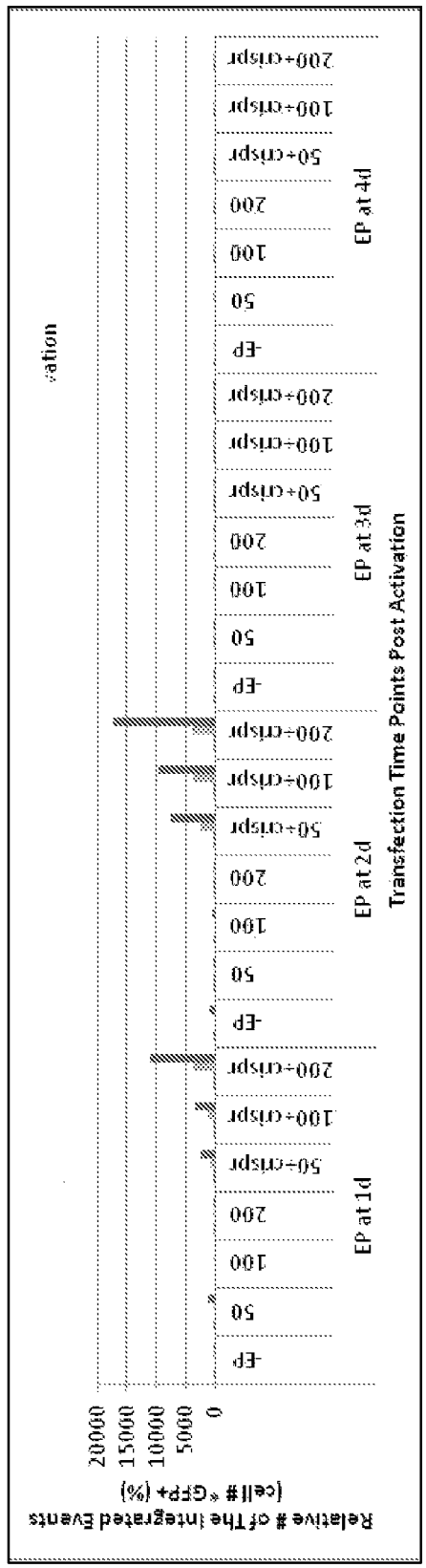
Figure 9D:
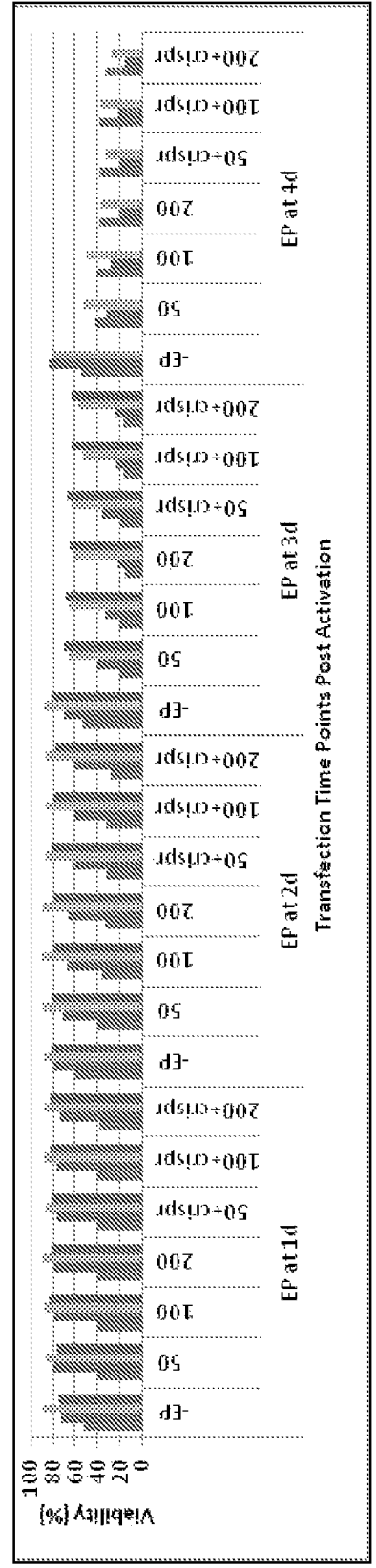
Figure 11:
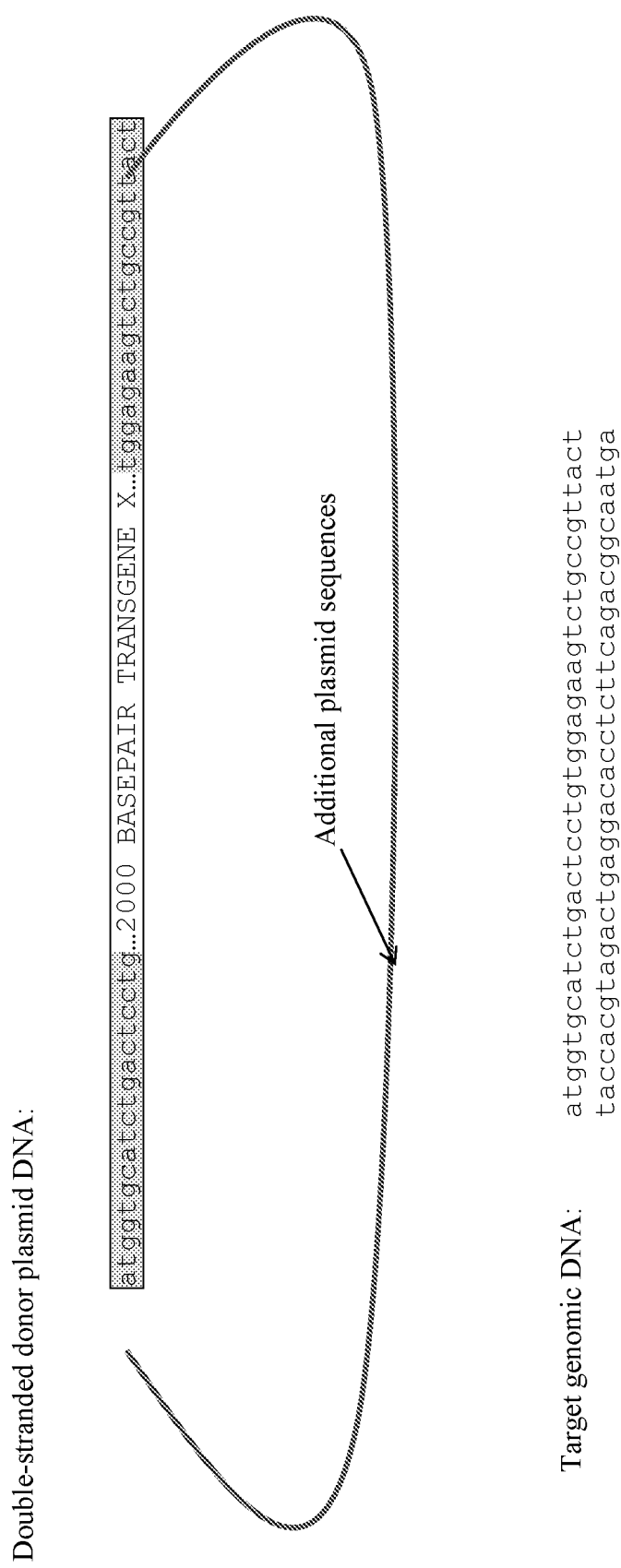

FIG. 9A-D shows the results of cells transfected either one, two, three, or four days post activation of the cells. FIG. 9A shows the proliferation of the cells transfected with either 50, 100, or 200 µg/ml plasmid DNA without the CRISPR system or 50, 100, or 200 µg/ml plasmid DNA with the CRISPR system. As shown in FIG. 9A, cell proliferation declined when the cells were transfected at 3 or more days post-transfection. Furthermore, the proliferation did not appear to be dependent on DNA concentration. FIG. 9D shows the viability of the cells. As shown in FIG. 9D, cell viability also declined when the cells were transfected at 3 or more days post-transfection, and the viability did not appear to be dependent on DNA concentration. FIG. 9B shows that the highest percentage of GFP-expressing cells was obtained when cells were transfected two days post activation. FIG. 9C shows that the relative number of integrated events (calculated as cell number×percentage of GFP-positive cells) was highest when cells were transfected two-days post activation.

Figure 15:
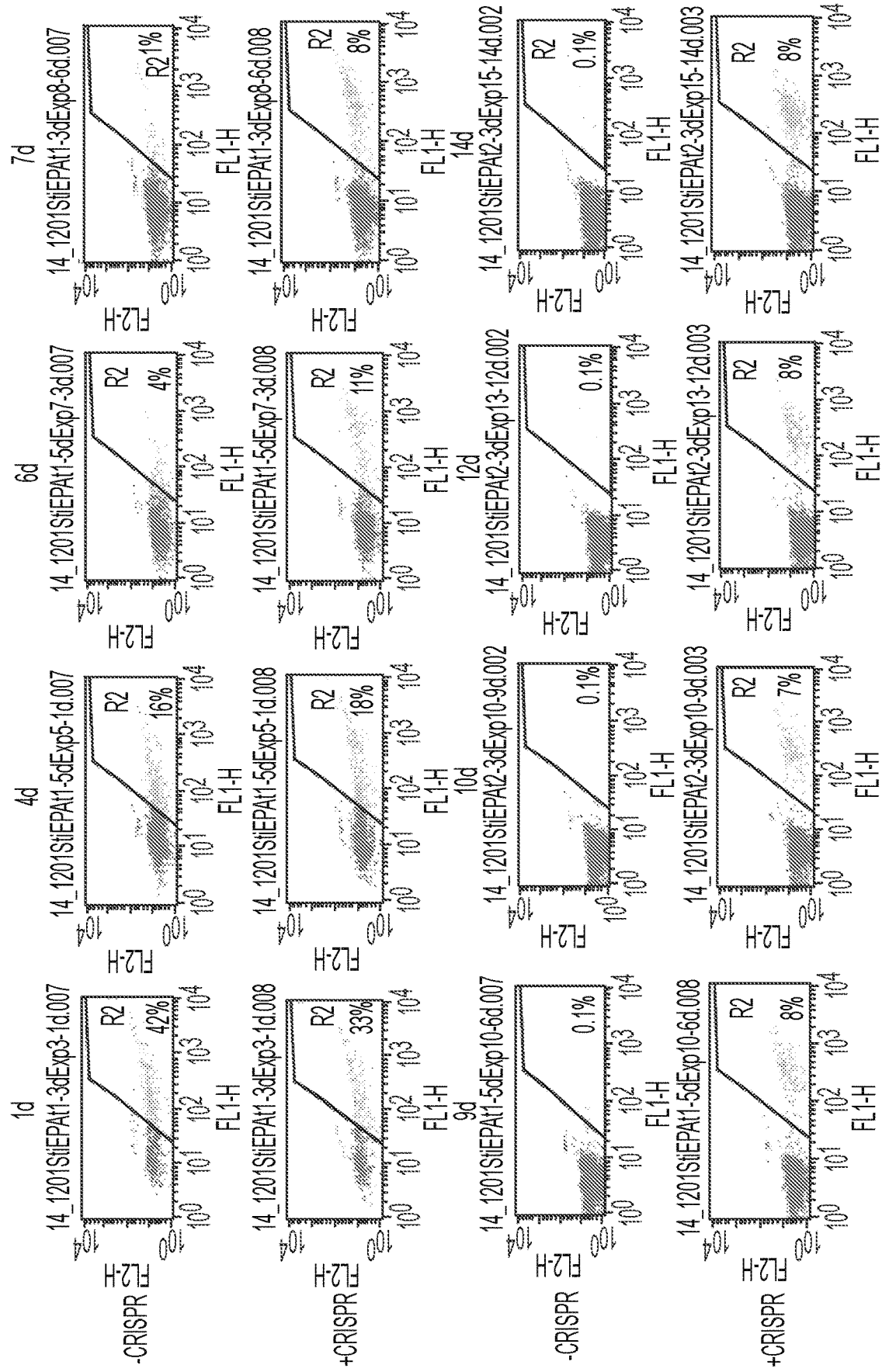
FIG. 15: Targeted Integration of PGK-eGFP-PolyA in AAVS1 Site of Expanded T Cells by mRNA-CRISPR and Donor Plasmid DNA (NoSelection; EP at 2d post Activation, 100 ug/ml plasmid DNA): Shown is FACS analysis of human expanded T cells transfected with PGK-eGFP-PolyA and with (+CRISPR, second and fourth rows) or without (−CRISPR, first and third rows) mRNA-CRISPR system. The cells were electroporated two days after activation of the cells (as described previously), and FACS analysis was done on cells at one, four, six, seven, nine, ten, twelve, and fourteen days post transfection. As shown in this figure, only cells transfected with the donor plasmid DNA and the CRISPR system showed stable GFP expression beyond four or six days post transfection.

These experiments were further confirmed by FACS analysis of expanded T cells activated as described previously and electroporated two days after activation with 100 µg/mL plasmid DNA and −CRISPR (FIG. 15, first and third rows) or +CRISPR (FIG. 15, second and fourth rows). As shown in FIG. 15, only cells transfected with CRISPR exhibited stable transgene expression beyond the 4 or 6-day time-point.

In conclusion, activation of T cells prior to transfection with plasmid DNA overcame the toxicity and efficiency loss associated with plasmid DNA in these cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An in vitro method for site-specific transgene insertion into a target genomic DNA region in isolated mammalian T cells, comprising:
   (i) contacting the T cells with an activating composition comprising anti-CD3 and anti-CD28 antibodies to produce activated T cells; and
   (ii) transfecting the activated T cells by electroporation two days post activation with a non-viral transfection composition comprising (a) a donor plasmid DNA, (b) a mRNA encoding a Cas9 DNA digesting agent and (c) a guide RNA;
   wherein the donor plasmid DNA comprises: a homologous region comprising nucleic acid sequence homologous to the target genomic DNA region; and a transgene of 500-5000 nucleic acids in length; and
   wherein the genomic DNA sequence is modified specifically at the target genomic DNA region; wherein the method provides stable transgene expression six days after transfection without selection medium.

2. The method of claim 1, wherein the donor plasmid DNA is a single-stranded.

3. The method of claim 1, wherein the isolated mammalian cells are human cells.

4. The method of claim 1, wherein the isolated mammalian cells are primary cells.

5. The method of claim 1, wherein the transgene comprises a chimeric antigen receptor (CAR).

6. The method of claim 1, wherein the transgene is 1000-5000 nucleic acids in length.

7. The method of claim 1, wherein the concentration of the donor plasmid DNA in the transfection composition is from about 50 µg/ml to about 500 µg/ml.

* * * * *